United States Patent
Bot et al.

(10) Patent No.: US 11,779,601 B2
(45) Date of Patent: Oct. 10, 2023

(54) DIAGNOSTIC METHODS FOR T CELL THERAPY

(71) Applicants: Kite Pharma, Inc., Santa Monica, CA (US); United States of America, as represented by the Secretary, Department of Health and Human Services, Rockville, MD (US)

(72) Inventors: Adrian Bot, Santa Monica, CA (US); Jeffrey S. Wiezorek, Santa Monica, CA (US); William Go, Santa Monica, CA (US); Rajul Jain, Santa Monica, CA (US); James N. Kochenderfer, Bethesda, MD (US); Steven A. Rosenberg, Bethesda, MD (US)

(73) Assignees: Kite Pharma, Inc., Santa Monica, CA (US); The United States of America as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 15/577,672

(22) PCT Filed: May 27, 2016

(86) PCT No.: PCT/US2016/034885
§ 371 (c)(1),
(2) Date: Nov. 28, 2017

(87) PCT Pub. No.: WO2016/191755
PCT Pub. Date: Dec. 1, 2016

(65) Prior Publication Data
US 2018/0344767 A1 Dec. 6, 2018

Related U.S. Application Data

(60) Provisional application No. 62/262,111, filed on Dec. 2, 2015, provisional application No. 62/167,738, filed on May 28, 2015.

(51) Int. Cl.
| | |
|---|---|
| *A61K 35/17* | (2015.01) |
| *C12N 5/0783* | (2010.01) |
| *C07K 14/52* | (2006.01) |
| *G01N 33/68* | (2006.01) |
| *A61P 35/00* | (2006.01) |
| *C07K 14/00* | (2006.01) |
| *C12N 15/00* | (2006.01) |
| *A61K 31/095* | (2006.01) |
| *A61K 31/445* | (2006.01) |
| *A61K 31/52* | (2006.01) |
| *A61K 31/665* | (2006.01) |
| *A61K 45/06* | (2006.01) |
| *C12N 15/85* | (2006.01) |

(52) U.S. Cl.
CPC ............ *A61K 35/17* (2013.01); *A61K 31/095* (2013.01); *A61K 31/445* (2013.01); *A61K 31/52* (2013.01); *A61K 31/665* (2013.01); *A61K 45/06* (2013.01); *A61P 35/00* (2018.01); *C07K 14/00* (2013.01); *C07K 14/52* (2013.01); *C12N 5/0636* (2013.01); *C12N 15/00* (2013.01); *C12N 15/85* (2013.01); *G01N 33/6869* (2013.01); *A61K 2300/00* (2013.01); *C12N 2510/00* (2013.01); *G01N 2333/5418* (2013.01); *G01N 2333/5443* (2013.01)

(58) Field of Classification Search
CPC ...... A61K 31/664; A61K 31/52; A61K 35/17; A61K 45/06; A61K 31/445; A61K 31/665; A61K 31/095
See application file for complete search history.

(56) References Cited

U.S. PATENT DOCUMENTS

| | | | |
|---|---|---|---|
| 5,595,756 A | * | 1/1997 | Bally .................. A61K 9/1272 264/4.1 |
| 5,728,388 A | | 3/1998 | Terman |
| 9,402,865 B2 | | 8/2016 | Powell et al. |
| 9,499,629 B2 | | 11/2016 | June et al. |
| 9,855,298 B2 | | 1/2018 | Bot et al. |

(Continued)

FOREIGN PATENT DOCUMENTS

| | | |
|---|---|---|
| CL | 2017-3005 | 5/2015 |
| CL | 201703005 | 11/2017 |

(Continued)

OTHER PUBLICATIONS

Melenhorst et al. Cytopenia and leukocyte recovery shape cytokine fluctuations after myeloablative allogeneic hematopoietic stem cell transplantation. Hematologica, 2012; 97(6):867-873 (Year: 2012).*

(Continued)

*Primary Examiner* — Vanessa L. Ford
*Assistant Examiner* — Sandra Dillahunt
(74) *Attorney, Agent, or Firm* — Arrigo, Lee, Guttman & Mouta-Bellum, LLP; Carla Mouta-Bellum

(57) ABSTRACT

The invention provides methods of increasing the efficacy of a T cell therapy in a patient in need thereof. The invention includes methods of identifying a patient who would respond well to a T cell therapy or conditioning a patient prior to a T cell therapy so that the patient responds well to a T cell therapy. The conditioning involves administering one or more preconditioning agents prior to a T cell therapy and identifying biomarker cytokines prior to administering a T cell therapy.

13 Claims, 24 Drawing Sheets

(56) References Cited

U.S. PATENT DOCUMENTS

| | | | |
|---|---|---|---|
| 10,322,146 | B2 | 6/2019 | Bot et al. |
| 2002/0006409 | A1 | 1/2002 | Wood |
| 2003/0031652 | A1 | 2/2003 | Hering et al. |
| 2011/0052547 | A1 | 3/2011 | Fowler et al. |
| 2013/0195800 | A1 | 8/2013 | Roeth et al. |
| 2013/0287748 | A1 | 10/2013 | June et al. |
| 2014/0050708 | A1 | 2/2014 | Powell et al. |
| 2014/0099309 | A1 | 4/2014 | Powell et al. |
| 2014/0154228 | A1 | 6/2014 | Volk et al. |
| 2014/0227237 | A1 | 8/2014 | June et al. |
| 2014/0377334 | A1 | 12/2014 | Irvine et al. |
| 2015/0093822 | A1 | 4/2015 | June et al. |
| 2015/0132290 | A1 | 5/2015 | Fuchs et al. |
| 2016/0346326 | A1 | 12/2016 | Bot et al. |
| 2017/0281766 | A1 | 10/2017 | Wiltzius et al. |
| 2017/0368101 | A1 | 12/2017 | Bot et al. |
| 2018/0344767 | A1 | 12/2018 | Bot et al. |

FOREIGN PATENT DOCUMENTS

| | | |
|---|---|---|
| CL | 2017-3006 | 5/2018 |
| CL | 2017003005 A1 | 5/2018 |
| CN | 104394877 A | 3/2015 |
| JP | 2014-507118 A | 3/2014 |
| JP | 2014-509841 A | 4/2014 |
| JP | 6917903 | 7/2021 |
| KR | 102349677 B | 1/2022 |
| OA | 18685 | 3/2019 |
| WO | 2004/021995 A2 | 3/2004 |
| WO | 2008081035 A1 | 7/2008 |
| WO | 2011119773 A1 | 9/2011 |
| WO | 2013169386 A1 | 11/2013 |
| WO | 2015069770 A1 | 5/2015 |
| WO | 2016/191756 A1 | 12/2016 |
| WO | 2016191755 A1 | 12/2016 |
| WO | 2016191756 A1 | 12/2016 |

OTHER PUBLICATIONS

National Cancer Institute. CAR T Cell Receptor Immunotherapy for Patients With B-cell Lymphoma. Available from: https://clinicaltrials.gov/ct2/show/NCT00924326. NLM identifier. NCT 00924326. First posted June (Year: 2009).*
National Cancer Institute. CAR T Cell Receptor Immunotherapy for Patients With B-cell Lymphoma. Available from: https://clinicaltrials.gov/ct2/show/NCT00924326. NLM identifier. NCT 00924326. First posted Jun. 2009.*
Salit et al. Dose-Adjusted EPOCH-Rituximab Combined With Fludarabine Provides an Effective Bridge to ReducedIntensity Allogeneic Hematopoietic Stem-Cell Transplantation in Patients With Lymphoid Malignancies. J Clin Oncol 30:830-836 (Year: 2012).*
Moschella et al. Cyclophosphamide Induces a Type I Interferon-Associated Sterile Inflammatory Response Signature in Cancer Patients' Blood Cells: Implications for Cancer Chemoimmunotherapy. Clin Cancer Res, 2013; 19(15); 4249-61 (Year: 2013).*
Park et al. Blood 2012; 120:1797 (Year: 2012).*
Bracci et al. Clinical Cancer Therapy, 2007; 13(2):644-653 (Year: 2007).*
Lu et al. Journal of Immunology, 2015, 194(4): 2011-2021 (Year: 2015).*
Heppner et al. Cancer Metastasis Review 2:5-23; 1983 (Year: 1983).*
Jain RK. Scientific American, Jul. 1994, 58-65 (Year: 1994).*
National Cancer Institute. CAR T Cell Receptor Immunotherapy for Patients With B-cell Lymphoma. Available from: https://clinicaltrials.gov/ct2/show/NCT00924326. NLM identifier. NCT 00924326. First posted Jun. 18, 2009. (Year: 2009).*
Rosenberg et al., "Personalized Cell Transfer Immunotherapy for B-Cell Malignancies and Solid Cancers," Molecular Therapy, 19(11):1928-1931 (Nov. 2011).

Huang et al., "Synergistic effect of adoptive T-cell therapy and intratumoral interferon y-inducible protein—transgene expression in treatment of established tumors," Cellular Immunology, 271:12-22 (2002).
Kochenderfer et al., "B-cell depletion and remissions of malignancy along with cytokine-associated toxicity in a clinical trial of anti-CD19 chimeric-antigen-receptor-transduced T cells," Blood, 119:2709-2720 (2012).
Kochenderfer et al., "Chemotherapy-Refractory Diffuse Large B-Cells Lymphoma and Indolent B-Cell Malignancies Can Be Effectively Treated with Autologous T Cells Expressing an Anti-CD19 Chimeric Antigen Receptor," Journal of Clinical Oncology, 33(6):540-549 (2015).
Bot et al., "Cyclophosphamide annd Fludarabine Conditioning Chemotherapy Induces a Key Homeostatic Cytokine Profile in Patients Prior to CAR T Cell Therapy," Blood, 126:4426-4433 (2015).
Perez et al., "Pharmacodynamic Profile and Clinical Response in Patients with B-Cell Malignancies of Anti-CD19 CAR T-Cell Therapy," Blood, 126:2042-2049 (2015).
Rossi et al., "Phase 1 Biomarker Analysis of the ZUMA-1 (KTE-C19-101) Study: A Phase 1-2 Multi-Center Study Evaluating the Safety and Efficacy of Anti-CD19 CAR T Cells (KTE-C19) in Subjects with Refactory Aggressive Non-Hodgkin Lymphoma," Blood, 126:2730-2737 (2015).
Dehqanzada et al., "Assessing serum cytokine profiles in breast cancer patients receiving a HER2/neu vaccine using Luminex technology," Oncol. Rep., 17:687-694 (Mar. 2007).
Chilean Office Action for Application No. 201703005 dated Jan. 8, 2019 (13 pages), with English Translation.
International Search Report and Written Opinion for PCT/US2016/034885 dated Jul. 27, 2016 (10 pages).
Extended European Search Report for EP 16800846 dated Nov. 27, 2018 (19 pages).
Notice of Allowance for U.S. Appl. No. 15/649,369, dated Feb. 14, 2019, which is related to this application.
Final Office Action for U.S. Appl. No. 15/649,369, dated Nov. 5, 2018, which is related to this application.
Non-Final Office Action for U.S. Appl. No. 15/649,369, dated Jul. 13, 2018, which is related to this application.
Non-Final Office Action for U.S. Appl. No. 15/649,369, dated Oct. 19, 2017, which is related to this application.
Notice To File Corrected Application Papers for U.S. Appl. No. 15/649,369, dated Jul. 20, 2017, which is related to this application.
Notice of Abandonment for U.S. Appl. No. 15/295,931, dated Jul. 5, 2017, which is related to this application.
Notice To File Missing Parts for U.S. Appl. No. 15/295,931, dated Oct. 31, 2016, which is related to this application.
Notice of Allowance for U.S. Appl. No. 15/167,977, dated Jul. 28, 2017, which is related to this application.
Notice of Allowance for U.S. Appl. No. 15/167,977, dated Jul. 14, 2017, which is related to this application.
Non-Final Office Action for U.S. Application No. 15/167,977, dated Feb. 6, 2017, which is related to this application.
Notice of Omitted Items for U.S. Appl. No. 15/167,977, dated Jun. 14, 2016, which is related to this application.
Written Opinion for Chilean Patent Application No. 201703006, dated Jul. 4, 2019 and is related to this subject application (7 pages).
English Translation of the Written Opinion for Chilean Patent Application No. 201703006, dated Jul. 4, 2019 and is related to this subject application (7 pages).
Written Opinion for Chilean Patent Application No. 201703005, dated Jul. 2, 2019 and is related to this subject application (7 pages).
English Translation of the Written Opinion for Chilean Patent Application No. 201703005, dated Jul. 2, 2019 and is related to this subject application (7 pages).
Coiffier, B., et al., "CHOP chemotherapy plus rituximab compared with CHOP alone in elderly patients with diffuse large-B-cell lymphoma," N Engl J Med 346(4):235-242, Massachusetts Medical Society, United States (2002).
Dudley, M.E., et al., "Cancer regression and autoimmunity in patients after clonal repopulation with antitumor lymphocytes," Science 298(5594):850-854, American Association for the Advancement of Science, United States (2002).

(56) References Cited

OTHER PUBLICATIONS

Dudley, M.E., et al., "Adoptive cell transfer therapy following non-myeloablative but lymphodepleting chemotherapy for the treatment of patients with refractory metastatic melanoma," J Clin Oncol. 23(10):2346-2357, American Society of Clinical Oncology, United States (2005).
Dudley, M.E., et al., "Adoptive cell therapy for patients with metastatic melanoma: evaluation of intensive myeloablative chemoradiation preparative regimens," J Clin Oncol. 26(32):5233-5239, American Society of Clinical Oncology, United States (2008).
Dudley, M.E., et al., "A phase I study of nonmyeloablative chemotherapy and adoptive transfer of autologous tumor antigen-specific T lymphocytes in patients with metastatic melanoma," Journal of Immunotherapy 25(3):243-251, Lippincott Williams & Wilkins, Inc., United States (2002).
Gattinoni, L., et al., "Removal of homeostatic cytokine sinks by lymphodepletion enhances the efficacy of adoptively transferred tumor-specific CD8+ T cells," J. Experiment. Med. 202(7):907-912, Rockefeller University Press, United States (2005).
Gisselbrecht, C., et al., "Salvage Regimens With Autologous Transplantation For Relapsed Large B-Cell Lymphoma in the Rituximab Era" Journal of Clinical Oncology 28(27):4184-4190, American Society of Clinical Oncology, United States (2010).
Harrison, J., "Kite Reports Cerebral Edema Death in ZUMA-1 CAR T-Cell Trial," Onclive.com, accessed at http://www.onclive.com/web-exclusives/kite-reports-cerebral-edema- death-in-zuma1-cartcell-trial?p=1, accessed on Jun. 7, 2017, 3 pages.
Klebanoff, C.A., et al., "Sinks, suppressors and antigen presenters: how lymphodepletion enhances T cell-mediated tumor immunotherapy," Trends Immunol. 26(2):111-117, Elsevier Science Ltd., England (2005).
Khouri, I.F., et al., "Transplant-Lite: Induction of Graft-Versus-Malignancy Using Fludarabine-Based Nonablative Chemotherapy and Allogeneic Blood Progenitor-Cell Transplantation as Treatment for Lymphoid Malignancies," Journal of Clinical Oncology 16(8):2817-2824, American Society of Clinical Oncology, United States (1998).
Kochenderfer, J.N. and Rosenberg, S.A., "Treating B-cell cancer with T cells expressing anti-CD9 chimeric antigen receptors," Nature Rev. Clin. Oncol. 10:267-276 (2013).
Kochenderfer, J.N., et al., "Anti-CD19 CAR T Cells Administered after Low-Dose Chemotherapy Can Induce Remissions of Chemotherapy-Refractory Diffuse Large B-Cell Lymphoma," Blood 124:550, American Society Of Hematology, United States, 3 pages (2014).
Kochenderfer, J.N. et al.,"Treatment of Chemotherapy-Refractory B-Cell Malignancies with Anti-CD19 Chimeric Antigen Receptor T cells," Molecular Therapy May 21-24, 2014 Amer. Soc. Gene & Cell Therapy 22 (Suppl. 1): S295 (2014).
Lee et al., "Autologous-Collected Donor-Derived CD 19-Directed Chimeric Antigen Receptor (CD 19-CAR) T Cells Induce a Complete Remission in Chemotherapy-Refractory Childhood Acute Lymphocytic Leukemia (ALL) Relapsing After Allogeneic Hematopoietic Stem Cell Transplantation (HSCT).", American Society of Hematology, Blood, vol. 120, issue 21, 2609.(2012).
Lee et al., "T cells expressing CD19 chimeric antigen receptors for acute lymphoblastic leukaemia in children and young adults: a phase 1 dose escalation trail", Lancet 385:571 528 (2015).
Locke, F.L., et al., "Updated Phase 1 Results From ZUMA-1: A Phase 1-2 Multicenter Study Evaluating the Safety and Efficacy of KTE-C19 (Anti-CD19 CAR T Cells) in Subjects With Refractory Aggressive Non-Hodgkin Lymphoma," Molecular Therapy 2016;24:S294.
Locke, F.L., et al., "Phase 1 Results of ZUMA-1: A Multicenter Study of KTE-C19 Anti-CD19 CAR T Cell Therapy in Refractory Aggressive Lymphoma," Mol Ther. 25(1):285-295. doi: 10.1016/j.ymthe.2016.10.020. Epub Jan. 4, 2017 (2017).
Maude, S.L., et al., "Chimeric Antigen Receptor T Cells for Sustained Remissions in Leukemia," The New England Journal of Medicine 371(16):1507-1517, Massachusetts Medical Society, United States (Oct. 16, 2014).

Moschella, F., et al., "Unraveling cancer chemoimmunotherapy mechanisms by gene and protein expression profiling of responses to cyclophosphamide," Cancer Research 71(10):3528-3539, American Association for Cancer Research, United States (2011).
Moschella, F., et al., "Cyclophosphamide induces a type I interferon-associated sterile inflammatory response signature in cancer patients' blood cells: implications for cancer chemoimmunotherapy," Clinical Cancer Research 19(15):4249-4261, American Association for Cancer Research, United States (2013).
O'Brien, S.M., et al., "Results of the Fludarabine and Cyclophosphamide Combination Regimen in Chronic Lymphocytic Leukemia," Journal of Clinical Oncology 19(5):1414-1420, American Society of Clinical Oncology, United States (2001).
Salit, R.B. et al., "Dose-adjusted EPOCH-rituximab combined with fludarabine provides an effective bridge to reduced-intensity allogeneic hematopoietic stem-cell transplantation in patients with lymphoid malignancies," J. Clin. Oncol. 30 (8): 830-836 (2012).
Schultz and Arnold, "Properties of Four Acute Phase Proteins: C-reactive Protein, Serum Amyloid A Protein, a1-acid Glycoprotein, and Fibrinogen", Seminars in Arthritis and Rheumatism, vol. 20, No. 3 Dec. 1990: pp. 129-147.
Sehn, L.H., et al., "Introduction of combined CHOP plus rituximab therapy dramatically improved outcome of diffuse large B-cell lymphoma in British Columbia" Journal of Clinical Oncology 23(22):5027-5033, American Society of Clinical Oncology, United States (2005).
Turtle, C.J., et al., "CD19 CAR-T cells of defined CD4+:CD8+ composition in adult B cell ALL patients," The Journal of Clinical Investigation 126(6):2123-2138, American Society for Clinical Investigation, United States (Mar. 2016).
Ziccheddu, G., et al., "The Janus face of cyclophosphamide: A sterile inflammatory response that potentiates cancer immunotherapy," Oncoimmunology 2(9):e25789:1-3, Landes Bioscience, United States (2013).
Food and Drug Administration, "Guidance for Industry: Estimating the Maximum Safe Starting Dose in Initial Clinical Trials for Therapeutics in Adult Healthy Volunteers," Jul. 2005, fda.gov, accessed at http://www.fda.gov/downloads/Drugs/%20..%20./Guidances/UCM078932.pdf, accessed on Oct. 14, 2016, 30 pages.
FDA Guidance for Sponsors, Clinical Investigators, and IRBs Data Retention When Subjects Withdraw from FDA-Regulated Clinical Trials, Retrieved from the internet, URL: http://www.fda.gov/Drugs/default.htm published Oct. 2008, Accessed on Jun. 27, 2014.
EPO Communication pursuant to Rules 70(2) and 70a(2) EPC for EP Application No. 16800847.2 dated Dec. 18, 2018, which is related to this subject application.
Extended EP Search Report or EP Application No. 16800847.2 dated Nov. 30, 2018, which is related to this subject application.
Official Action for Eurasian Application No. 2001792649 dated May 6, 2019, which is related to this subject application.
English Translation of Official Action for Eurasian Application No. 2001792649 dated May 6, 2019, which is related to this subject application.
Office Action for Chilean Application 201703006 dated Jan. 9, 2019, which is related to this subject application.
English Translation for Office Action for Chilean application 201703006 dated Jan. 9, 2019, which is related to this subject application.
Office Action for Chilean Application 201703005 dated Jan. 8, 2019, which is related to this subject application.
English Translation for Office Action for Chilean application 201703005 dated Jan. 8, 2019, which is related to this subject application.
EPO Communication pursuant to Rules 70(2) and 70a(2) EPC for EP Application No. 16800846.4 dated Jan. 8, 2019 which is related to this subject application.
Non-Final Office Action for U.S. Appl. No. 15/950,042, dated Oct. 25, 2018, which corresponds to the application related to this application.
Final Office Action for U.S. Appl. No. 15/950,042, dated Apr. 2, 2019, which corresponds to the application related to this application.
Non-Final Office Action for U.S. Appl. No. 15/950,042, dated Nov. 5, 2019, which corresponds to the application related to this application.

(56) References Cited

OTHER PUBLICATIONS

International Search Report for PCT Application No. PCT/US16/34888, ISA/US Commissioner for Patents, United States, dated Oct. 14, 2016, and is related to this subject application.
Written Opinion for PCT Application No. PCT/US16/34888, ISA/US Commissioner for Patents, United States, dated Oct. 14, 2016, and is related to this subject application.
Official and English Translation of Office Action mailed in counterpart Japanese Patent Application No. 2017-561968 dated May 12, 2020.
Preliminary Examination Report received for Singaporean Patent Application Serial No. 10201913623P dated Mar. 3, 2020, 2 pages.
Office Action dated Dec. 10, 2020 for Saudi Arabia Patent Application No. 517390396, English translation and original version.
Office Action dated Dec. 8, 2020 for Saudi Arabia Patent Application No. 517390394, English translation and original version.
Original and English Translation of Office Action dated Aug. 5, 2020 in Taiwan Patent Application No. 105116879, counterpart of related subject matter application.
Office Action dated Nov. 2, 2020 for Israel Patent Application No. 255887.
Office Action dated Nov. 4, 2020 for Israel Patent Application No. 255888.
English Translation and Original Examination Report dated Jul. 14, 2020 in Saudi Arabian Patent Application No. 517390394, related subject matter.
English Translation and Original Examination Report dated Jul. 8, 2020 in Saudi Arabian Patent Application No. 517390396, foreign counterpart.
English Translation and Original Office Action dated Jun. 23, 2020 in Japanese Patent Application No. 2017-561794, related subject matter.
Office Action dated Oct. 10, 2020 for Chinese Patent Application No. 201680038203.7.
Guifang, Li, (2002) "An excerpt of results of the fludarabine and cyclophosphamide combination regimen in chronic lymphocytic leukemia," Foreign Medical Sciences (Cancer Section), 29(2), 158-159, which was cited in Chinese.
O'Brien S M, et al. (2001), "Results of the fludarabine and cyclophosphamide combination regimen in chronic lymphocytic leukemia," J Clin Oncol, 19(5), 1414-20 This is the "A" reference on p. 1 of the search report in the Office Action.
Yadan, L. et al. (2015), CD19 and immunotherapy of B-cell lineage malignancies, Chin J Cancer Biother, 22(1), 99-103.
Office Action dated Sep. 2, 2020 for Chinese Patent Application No. 201680030892.7.
Jie et al. (2014), "Introduction of Chimeric Antigen Receptor-engineered T Cells and the Clinical Use for Anticancer," 36(2), 1-8.
Office Action dated Jan. 26, 2021 for counterpart Japanese Patent Application No. 2017-561968, English translation and original version.
Office Action Received for Taiwanese Patent Application Serial No. TW105116879, dated Jan. 15, 2020, 13 pages.
Hong et al., "Successful Treatment of Melanoma Brain Metastases with Adoptive Cell Therapy", Clinical Cancer Research, 2010, vol. 16, No. 19, pp. 4892-4898.
Preliminary Examination Report received for Singaporean Patent Application Serial No. 10201913620Q dated Mar. 3, 2020, 2 pages.
Original and English Translation of Office Action received for Eurasian Patent Application Serial No. 201792642/28 dated Mar. 17, 2020.
Examination report dated Apr. 3, 2020 in European Patent application No. 16800846.4.
Bracci et al., "Cyclophosphamide enhances the antitumor efficacy of adoptively transferred immune cells through the induction of cytokine expression, B-cell and T-cell homeostatic proliferation, and specific tumor infiltration," Clin Cancer Res 13(2 Pf 1):644-653, American Association for Cancer Research, United States (2007).

Rosenberg et al., "Durable Complete Responses in Heavily Pretreated Patients With Metastatic Melanoma Using T-cell Transfer Immunotherapy," Clinical Cancer Research 17(13):4550-4557, The Association, United States (2011).
International Search Report and Written Opinion for International Application No. PCT/US16/34888, ISA/US, Commissioner for Patents, Alexandria, Virginia, dated Oct. 14, 2016, 14 pages.
Extended European Search Report for EP 16800847 dated Nov. 30, 2018. (8 pages).
Jain, RK., "Barriers to drug delivery in solid tumors", Scientific American, Jul. 1994, vol. 271, pp. 58-65.
Preliminary Examination Report received for Singaporean Patent Application Serial No. 10201913604T dated Feb. 10, 2020, 1 page.
Preliminary Examination Report received for Singaporean Patent Application Serial No. 10201913613S dated Mar. 3, 2020, 2 pages.
Communication pursuant to Article 94(3) EPC received for European Patent Application Serial No. 16800847.2 dated Apr. 28, 2020, 4 pages.
International Preliminary Report on Patentability Chapter 1 received for PCT Application Serial No. PCT/US2016/034888 dated Dec. 7, 2017, 11 pages.
Communication pursuant to Article 94(3) EPC received for European Patent Application Serial No. 16800846.4 dated Apr. 3, 2020, 4 pages.
Final Office Action received for U.S. Appl. No. 15/950,042 dated Apr. 3, 2020, 22 pages.
Original and English Translation of Office Action dated Mar. 19, 2020 in Indonesian Patent Application No. P00201709434.
Brentjens, R. et al. "Treatment of Chronic Lymphocytic Leukemia with Genetically Targeted Autologous T Cells: Case Report of an Unforeseen Adverse Event in a Phase I Clinical Trial," The American Society of Gene & Cell Therapy, vol. 18, No. 4, 3 pages.
Kalos, M., et al. "T Cells with Chimeric Antigen Receptors Potent Antitumor Effects and Can Establish Memory in Patients with Advanced Leukaemia," Presentation by Thressi Maxwell, Neurochemistry Laboratory CMC, Sep. 2011, 42 pages.
ClinicalTrials.gov, "CAR T Receptor Immunotherapy for Patients with B-Cell Lymphoma," National Cancer Institute, Clinical Trial Identifier No. NCT00924326, results posted: Mar. 21, 2019, 23 pages.
Office Action dated Mar. 2, 2021 for Japanese Patent Application No. 2017-561794, English translation and original version.
Examination Report issued in related European Patent Application No. 16800846.4, dated Jun. 23, 2021, 9 pages.
Patent Examination Report 1 issued in New Zealand Patent Application No. 737359, dated Jun. 21, 2021, 4 pages.
Notice of Preliminary Rejection and its English translation issued in Korean Patent Application No. 10-2017-7037017, dated Aug. 8, 2021, 5 pages.
Third Party Observations submitted in related EP Application No. 16800846.4 with the European Patent Office on Jan. 25, 2021, 6 pages.
Office Action and English translation issued in related Chinese Patent Application No. 201680038203.7, dated Jun. 7, 2021, 28 pages.
Rejection Notification and English translation issued in related Saudi Arabian Patent Application No. 517390396, dated Jun. 30, 2021, 8 pages.
Substantive Examination Report (Restriction) issued in Philippine Patent Application No. 1/2017/502154, dated Mar. 2, 2021, 4 pages.
Extended European Search Report issued in European Patent Application No. 20204879.9, dated Jun. 17, 2021, 8 pages.
Office Action (and English translation) issued in Saudi Arabian Application No. 517390394, dated Dec. 8, 2020 8 pages.
Non-Final Office Action received for U.S. Appl. No. 15/950,042, dated Sep. 13, 2021, 23 pages.
Examination Report issued in Australian Patent Application No. 2016268864, dated May 18, 2021, 5 pages.
Notification of Second Office Action and English translation in Chinese Patent Application No. 201680030892.7, dated May 26, 2021, 10 pages.
Office Action (and English translation) issued in Japanese Patent Application No. 2017-561794, dated Mar. 2, 2021, 2 pages.

(56) References Cited

OTHER PUBLICATIONS

Examination Report No. 1 issued in Australian Patent Application No. 2016268863, dated Jun. 15, 2021, 6 pages.
Office Action (and English translation) dated Jan. 26, 2021 for Japanese Patent Application No. 2017-561968, 8 pages.
Decision to Grant a Patent and English Translation issued in Japanese Patent Application No. 2017-561968, dated Jun. 29, 2021, 6 pages.
Korean Office Action dated May 11, 2022 in connection with Korean Application No. 10-2017-7037018, 3 pages.
English translation of Summary of Korean Office Action dated May 11, 2022 in connection with Korean Application No. 10-2017-7037018, 1 page.
Australian Examination Report dated Mar. 29, 2022 in connection with Australian Application No. 2016268863, 3 pages.
Mexican Office Action dated Apr. 25, 2022 in connection with Mexican Application No. MX/a/2017/015186, 4 pages.
English translation of Mexican Office Action dated Apr. 25, 2022 in connection with Mexican Application No. MX/a/2017/015186, 3 pages.
New Zealand Office Action dated May 6, 2022 in connection with New Zealand Application No. 737359, 5 pages.
Korean Office Action dated Apr. 12, 2022 in connection with Korean Application No. 10-2022-7000444, 3 pages.
English language translation of Korean Office Action dated Apr. 12, 2022 in connection with Korean Application No. 10-2022-7000444, 3 pages.
Saudi Arabia Office Action dated Apr. 12, 2022 in connection with Saudi Arabia Application No. 517390394, 5 pages.
English translation of Saudi Arabia Office Action dated Apr. 12, 2022 in connection with Saudi Arabia Application No. 517390394, 4 pages.
Australian Office Action dated May 23, 2022 in connection with Australian Application No. 2016268864, which has related subject matter but is not foreign counterpart, 3 pages.
Saudi Arabia Office Action dated Jun. 7, 2022 in connection with Saudi Arabia Application No. 521421432, which has related subject matter but is not foreign counterpart, 4 pages.
English translations of Saudi Arabia Office Action dated Jun. 7, 2022 in connection with Saudi Arabia Application No. 521421432, which has related subject matter but is not foreign counterpart, 4 pages.
Canadian Office Action dated Jun. 22, 2022 in connection with Canadian Application No. 2,986,798, which has related subject matter but is not foreign counterpart, 4 pages.
New Zealand Office Action dated Jul. 13, 2022 in connection with New Zealand Application No. 737359, which has related subject matter but is not foreign counterpart, 5 pages.
Japanese Office Action and English translation dated Jul. 26, 2022 in connection with Japanese Application No. 2017-561794, which has related subject matter but is not foreign counterpart, 10 pages.
Canadian Office Action dated Jul. 4, 2022 in connection with Canadian Application No. 2,986,793, 7 pages.
European Communication dated Sep. 16, 2022 in connection with European Application No. 16800846.4, 7 pages.
Australian Office Action dated Jun. 9, 2022 in connection with Australian Application No. 2016268863, 4 pages.
Saudi Arabia Office Action dated Jun. 7, 2022 in connection with Saudi Arabia Application No. 521421433, 4 pages.
English translations of Saudi Arabia Office Action dated Jun. 7, 2022 in connection with Saudi Arabia Application No. 521421433, 4 pages.
Canadian Office Action dated Jun. 22, 2022 in connection with Canadian Application No. 2,986,798, 4 pages.
New Zealand Office Action dated Jul. 13, 2022 in connection with New Zealand Application No. 737359, 5 pages.
Japanese Office Action, and English translation thereof, dated Jul. 26, 2022 in connection with Japanese Application No. 2017-561794, which has related subject matter but is not foreign counterpart, 10 pages.
Saudi Arabia Office Action dated Sep. 18, 2022 in connection with Saudi Arabia Application No. 517390396, 8 pages.
English translation of Saudi Arabia Office Action dated Sep. 18, 2022 in connection with Saudi Arabia Application No. 517390396, 10 pages.
Korean Office Action, and English translation thereof, dated May 11, 2022 in connection with Korean Application No. 10-2017-7037018, 5 pages.
Third Party Observations filed in European Application counterpart EP application No. 16800846.4.
Thiant et al., 2011, Plasma levels of IL-7 and IL-15 after reduced intensity conditioned allo-SCT and relationship to acute GVHD. Bone Marrow Transplantation 46, 1374-1381.
Israel Office Action dated Jun. 22, 2022 in connection with Israel Application No. 284173, 4 pages.
English translation of Israel Office Action dated Jun. 22, 2022 in connection with Israel Application No. 284173, 5 pages.
Saudi Arabia Office Action dated Oct. 17, 2022 in connection with Saudi Arabia Application No. 521421433, 4 pages.
English translation of Saudi Arabia Office Action dated Oct. 17, 2022 in connection with Saudi Arabia Application No. 521421433, 4 pages.
Saudi Arabia Office Action dated Oct. 17, 2022 in connection with Saudi Arabia Application No. 521421432, which has related subject matter but is not foreign counterpart, 4 pages.
English translation of Saudi Arabia Office Action dated Oct. 17, 2022 in connection with Saudi Arabia Application No. 521421432, which has related subject matter but is not foreign counterpart, 4 pages.
Taiwan Office Action dated Jan. 6, 2022 in connection with Taiwan Application No. 105116879, 10 pages.
English language translation of Taiwan Office Action dated Jan. 6, 2022 in connection with Taiwan Application No. 105116879, 13 pages.
Taiwan Search Report dated Jan. 6, 2022 in connection with Taiwan Application No. 105116879, 1 page.
Original and English Translation of Preliminary Rejection dated Dec. 21, 2021, in Korean Patent Application No. 10-2017-7037018.
English language Preliminary Rejection dated Jan. 10, 2022, in New Zealand Patent Application No. 737359.
Original and English Translation of Rejection Decision dated Nov. 1, 2021, in Chinese Patent Application No. 201680038203.7.
Pawel Muranski et al., "Increased intensity lymphodepletion and adoptive immunotherapy—how far can we go?", Nature Clinical Practice Oncology, vol. 3 (No. 12):pp. 668-681 (Dec. 2006).
Related application but not foreign counterpart Korean Patent Application No. 10-2022-7000444: Office Action and English Translation Thereof dated Oct. 13, 2022, 7 pages.
Related application but not foreign counterpart Mexican Patent Application No. MX/a/2017/015186: Office Action and English Translation Thereof dated Oct. 21, 2022, 8 pages.
Related application but not foreign counterpart Brazilian Patent Application No. BR112017025166-3: Search Report and English Translation Thereof dated Sep. 14, 2021, 7 pages.
Unknown, "Guidance for Industry: Estimating the Maximum Safe Starting Dose in Initial Clinical Trials for Therapeutics in Adult Healthy Volunteers.", U.S. Department of Health and Human Services Food and Drug Administration Center for Drug Evaluation and Research (CDER), http://www.fda.gov/cder/guidance/index.htm, Jul. 2005, 30 pages.
Foreign counterpart Japanese Patent Application No. 2021-086807: Office Action and English Translation Thereof dated Dec. 13, 2022, 4 pages.
Foreign counterpart Vietnamese Patent Application No. 1-2017-05313: Office Action and English Translation Thereof dated Dec. 30, 2022, 4 pages.
Related application but not foreign counterpart Taiwan Patent Application No. 105116879, Allowance Decision of Re-Examination and English translation, dated Feb. 16, 2023, 3 pages.
Related application but not foreign counterpart Japanese Patent Application No. 2017-561794: Decision to Grant and English Translation Thereof dated Dec. 13, 2022, 4 pages.

(56) References Cited

OTHER PUBLICATIONS

Related application but not foreign counterpart Japanese Patent Application No. 2012-110476: Decision to Grant and English Translation Thereof dated Jan. 23, 2023, 8 pages.

Foreign counterpart Korean Patent Application No. 10-2022-7045189: Office Action and partial English Translation Thereof dated Feb. 27, 2023, 12 pages.

Related application but not foreign counterpart Korean Patent Application No. 10-2022-700044, Notice of Final Rejection and English translation, dated Mar. 3, 2023, 5 pages.

Office Action dated Jun. 19, 2023 in foreign related but not counterpart Taiwan Patent Application No. 111125144 with English translation.

IPO Search Report from foreign related but not counterpart Taiwan Patent Application No. 111125144.

Office Action dated May 16, 2023 in foreign related but not counterpart Brazilian Patent Application No. BR112017025166-3 with English translation.

Office Action dated Jun. 19, 2023 in foreign related but not counterpart Brazilian Patent Application No. BR122021025441-9 with English translation.

Office action dated May 16, 2023 in related but not foreign counterpart Brazilian Patent Application N° BR112017025166-3, Office, English translation attached.

Office Action dated Jun. 6, 2023 in foreign counterpart Vietnamese Patent Application No. 1-2023-02058 with English translation.

Office Action dated May 11, 2023 in foreign counterpart Chinese Patent Office Action application No. 202210127095.8 with English translation.

Decision to Grant in foreign counterpart Japanese Patent Application No. 2021-086807, dated May 30, 2023.

European Search Report with Opinion issued in counterpart application EP 23157411.2 dated Jul. 26, 2023 (10 pages).

J. N. Kochenderfer et al: "B-cell depletion and remissions of malignancy along with cytokine-associated toxicity in a clinical trial of anti-CDI9 chimeric-antigen-receptor-transduced T cells", Blood, vol. 119, No. 12, Dec. 8, 2011 (Dec. 8, 2011), pp. 2709-2720.

Office Action dated Jul. 10, 2023 in counterpart Brazil—Patent Application N° BR112017025120-5 with English Translation.

English Translation of Office Action dated Jul. 10, 2023 in counterpart Brazil—Patent Application N° BR112017025120-5.

Office Action dated Jul. 11, 2023 in counterpart Korean Patent Application No. 10-2022-7045189 with English translation.

English Translation of Office Action dated Jul. 11, 2023 in counterpart Related Korean Patent Application No. 10-2022-7045189 with English translation.

Office Action from Related Korean application Korean Patent Application No. 10 2022 7000444, dated Jul. 11, 2023 ( pages).

English Translation of Office Action from Related Korean application Korean Patent Application No. 10 2022 7000444, dated Jul. 11, 2023 ( pages).

\* cited by examiner

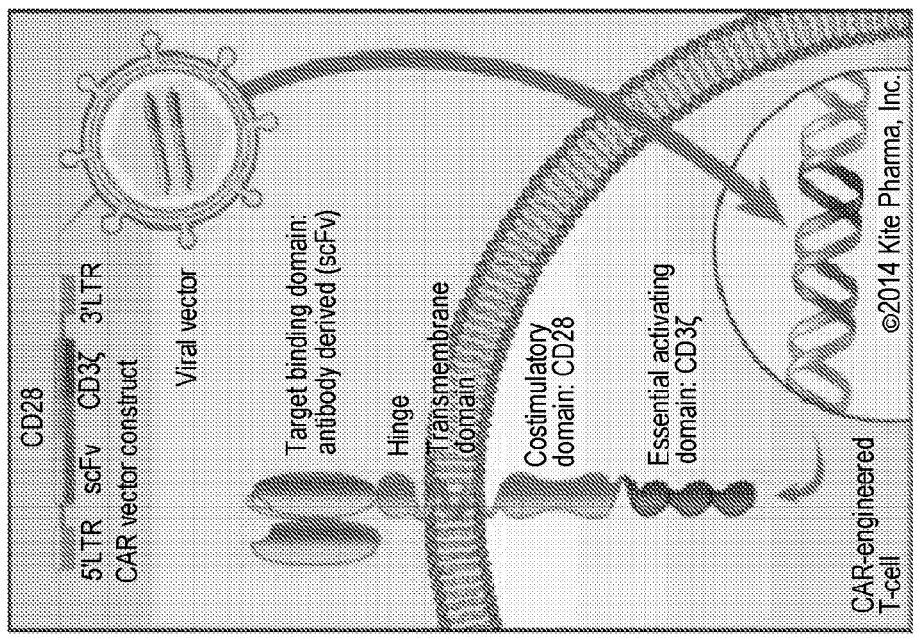
FIG. 1 – CAR-Engineered T Cell Schematic

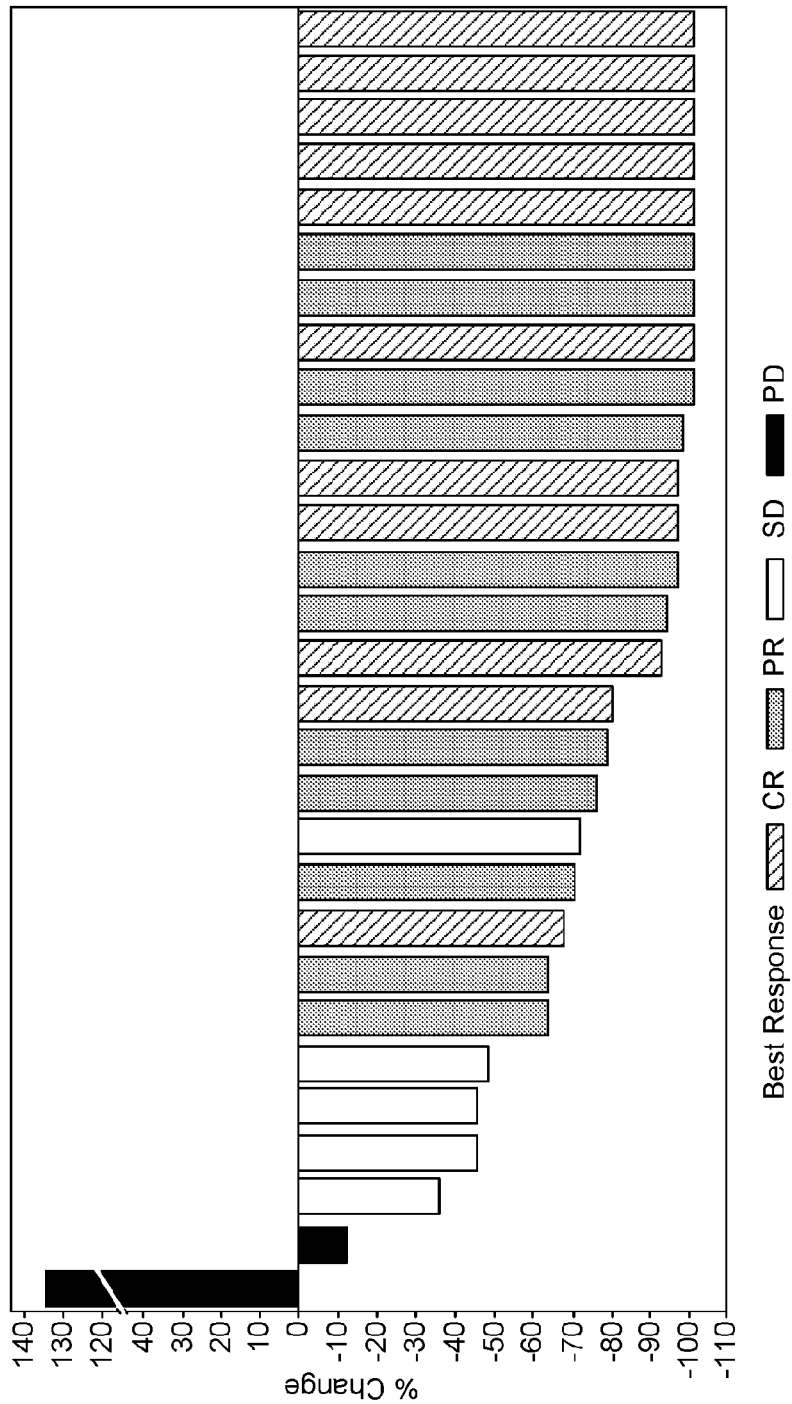
FIG. 2A – Best response to anti-CD19 CAR+ T cells in B cell malignancies

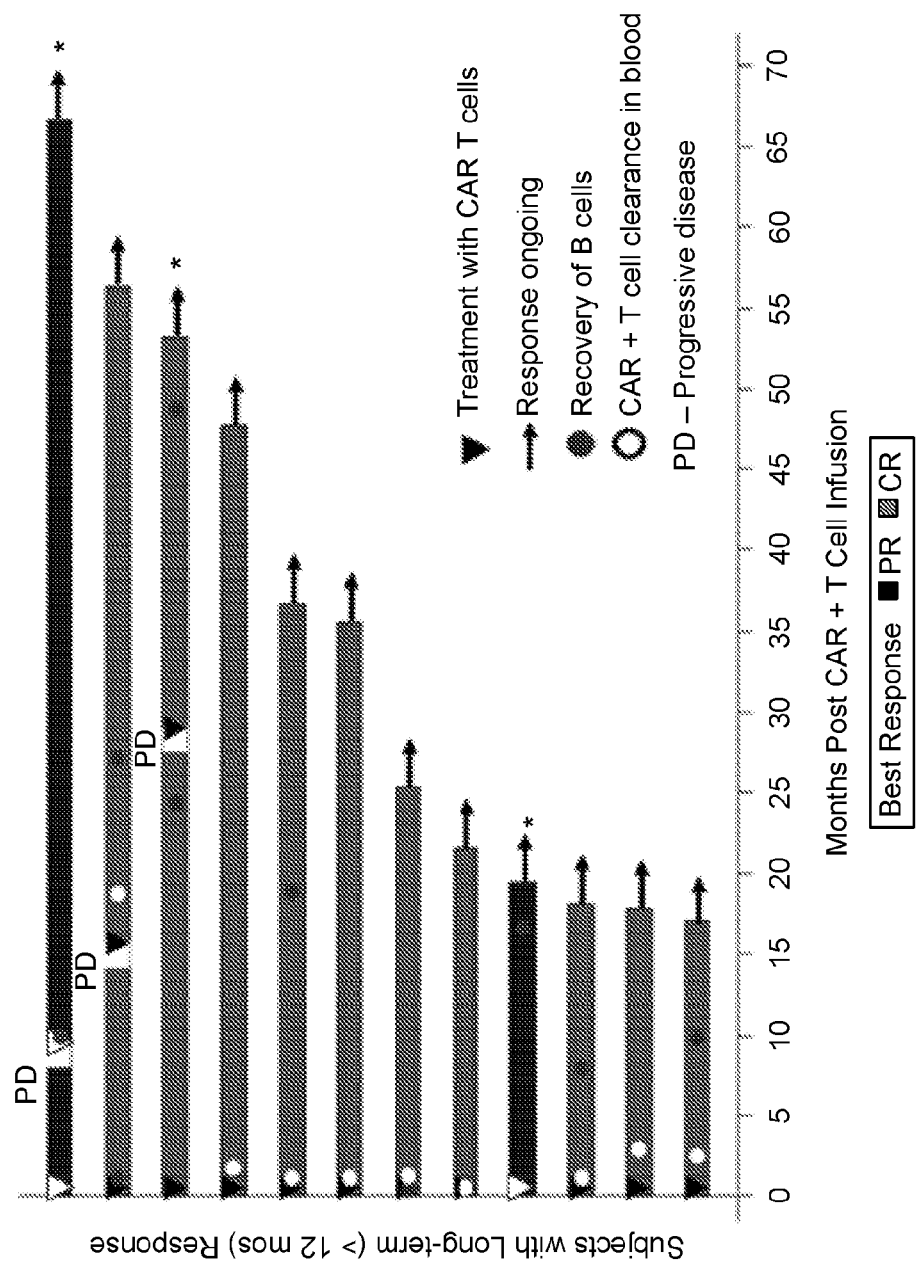

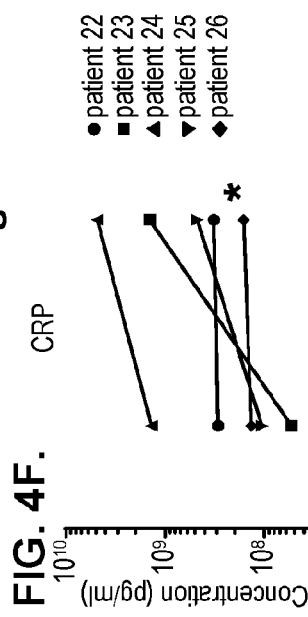
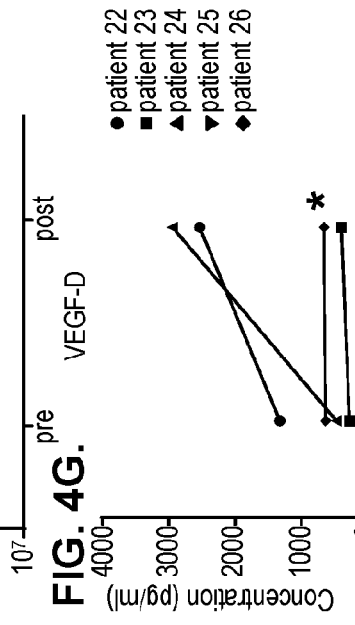
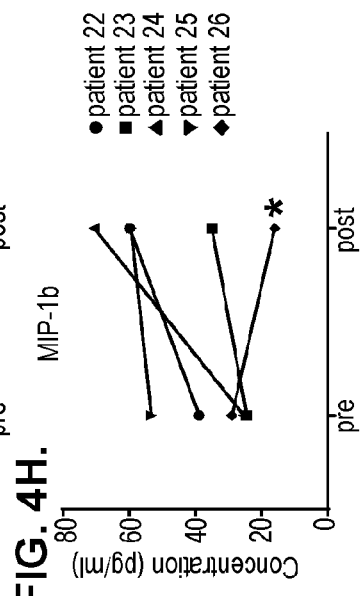
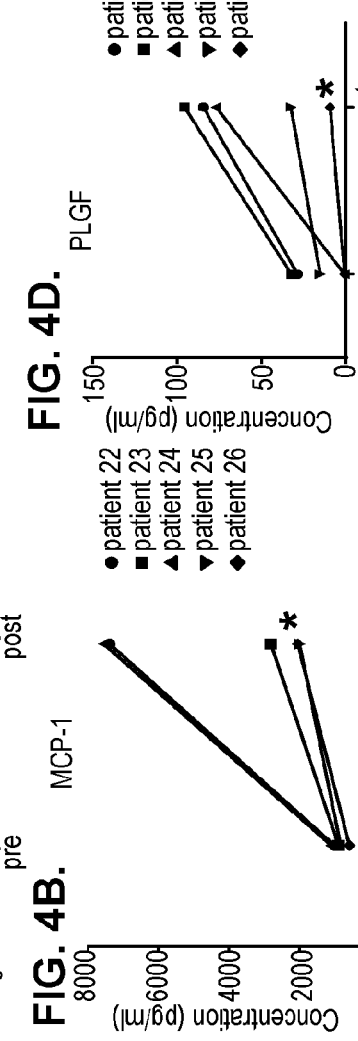
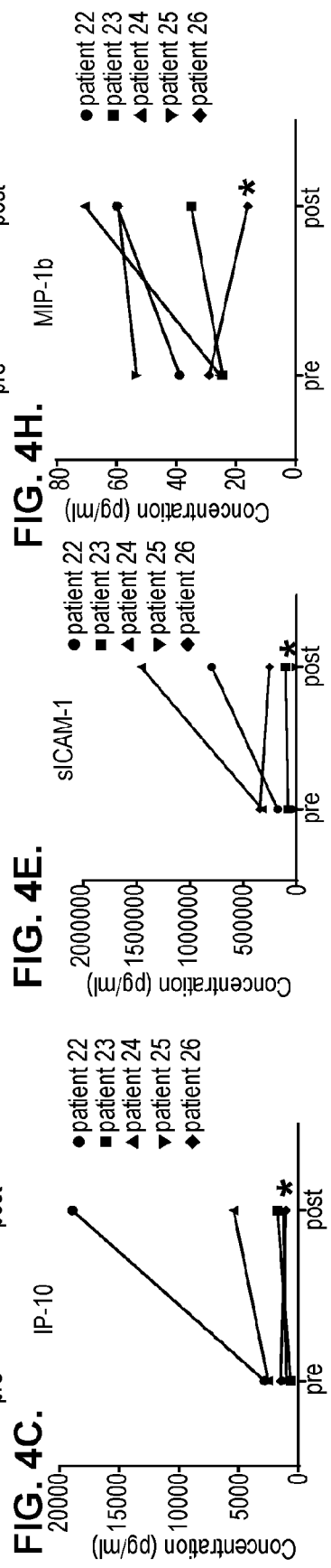
FIG. 4 – Serum Levels of select cytokines before and after conditioning

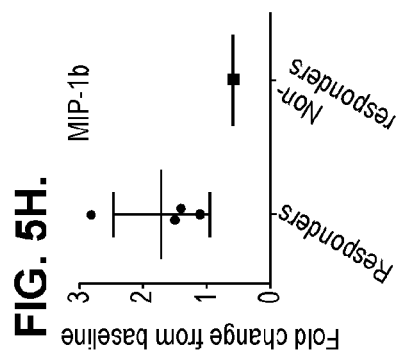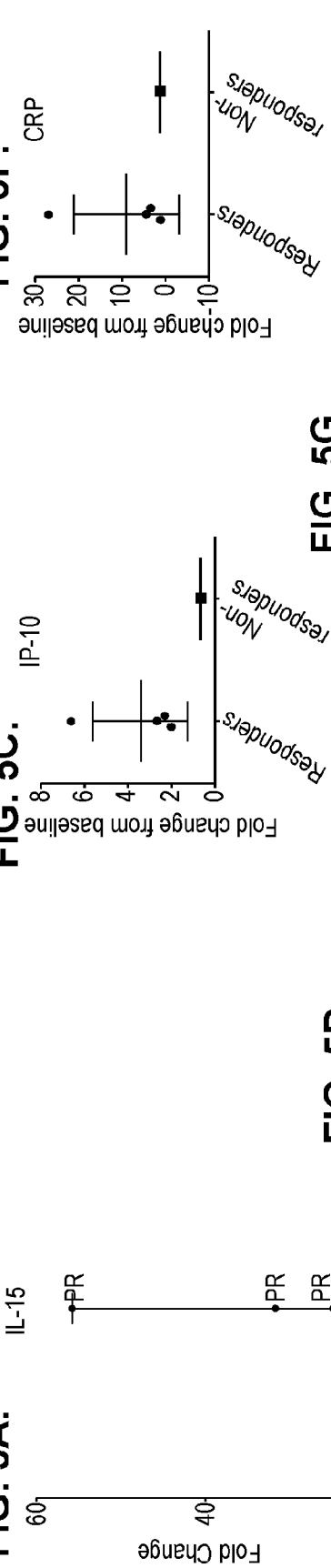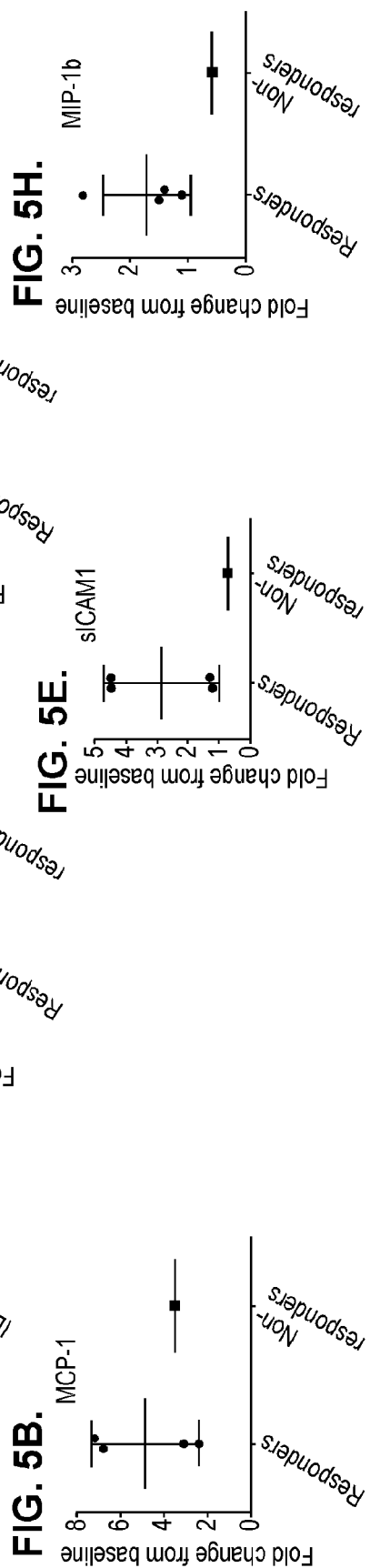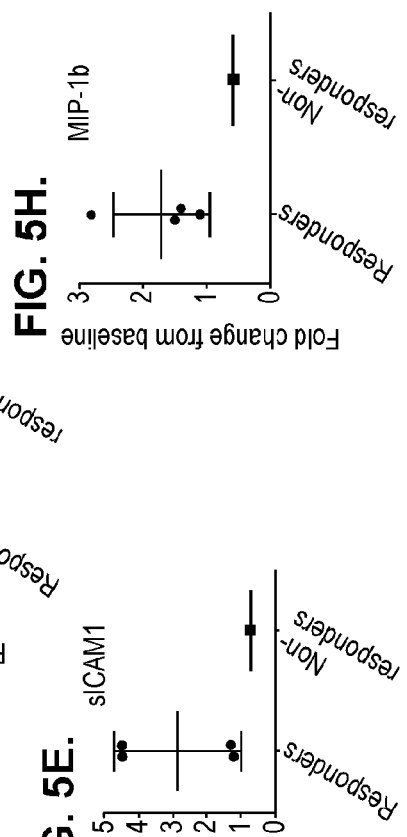
FIG. 5 – Serum Levels of select cytokines before and after conditioning

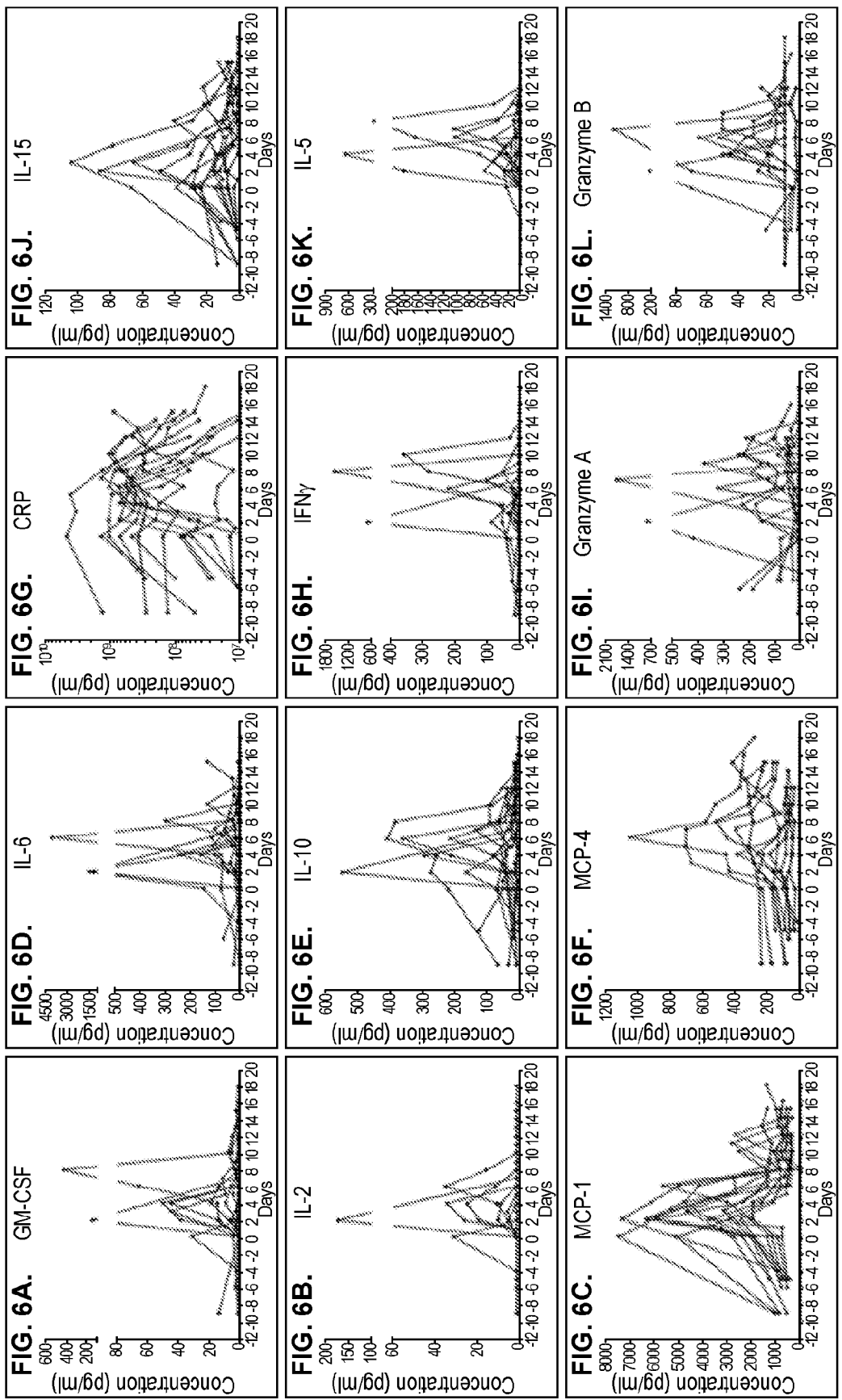
FIG. 6 – Analysis of patient serum levels of select cytokines

FIG. 6 (cont'd)
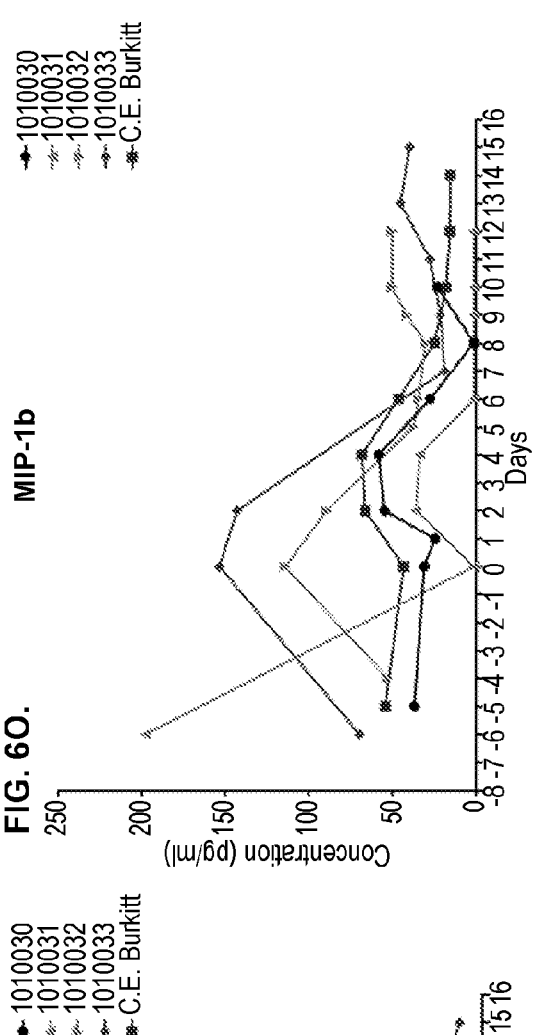
FIG. 6M.
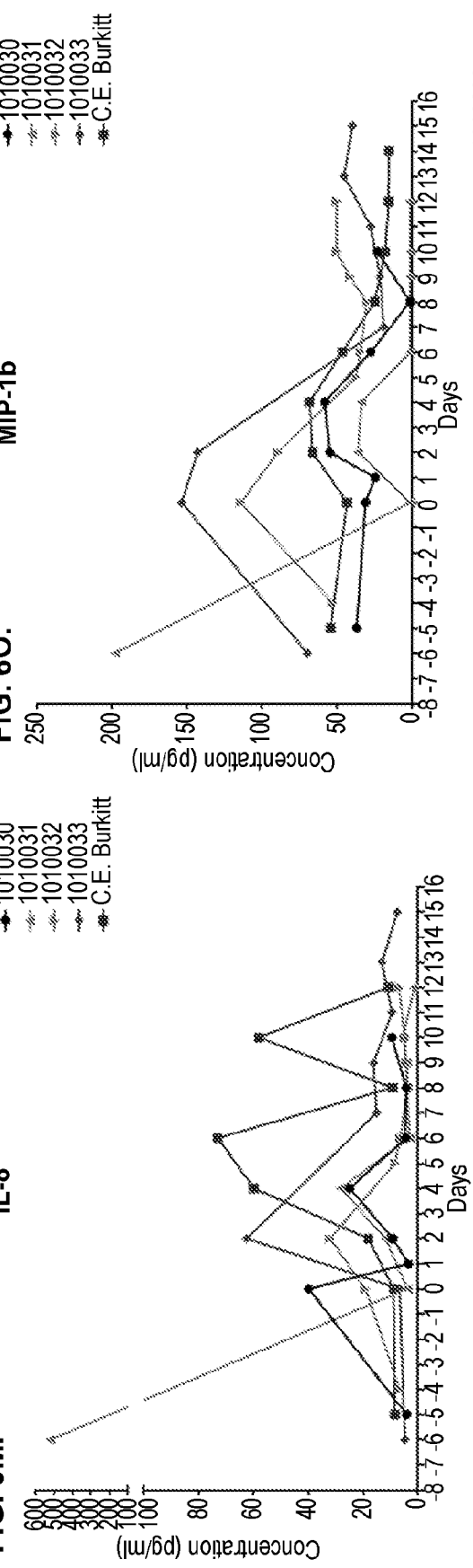
FIG. 6N.
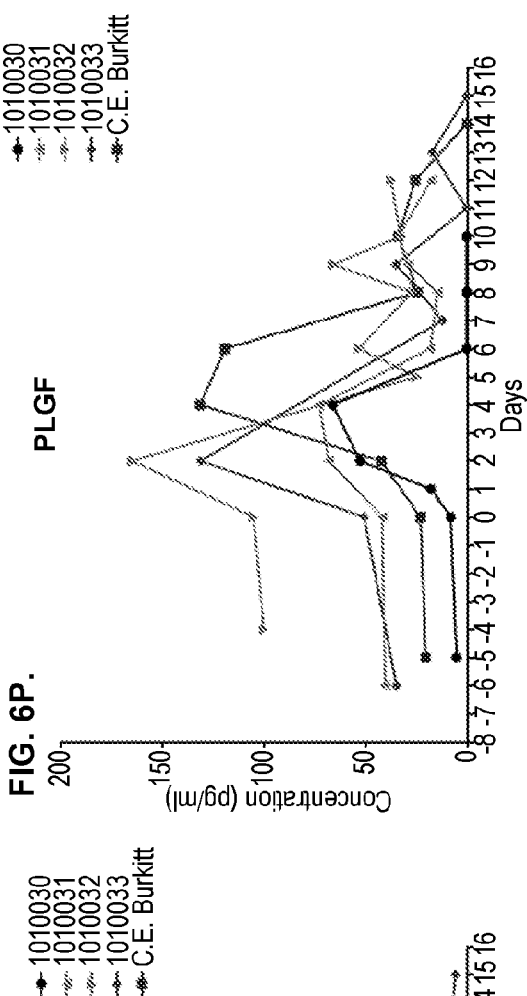
FIG. 6O.
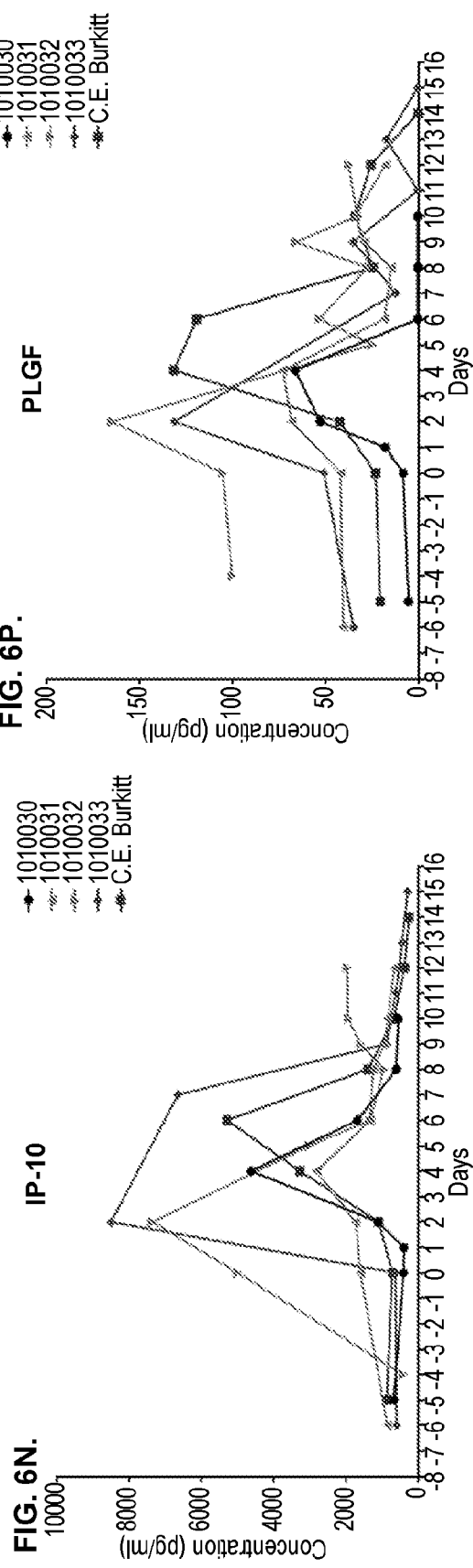
FIG. 6P.

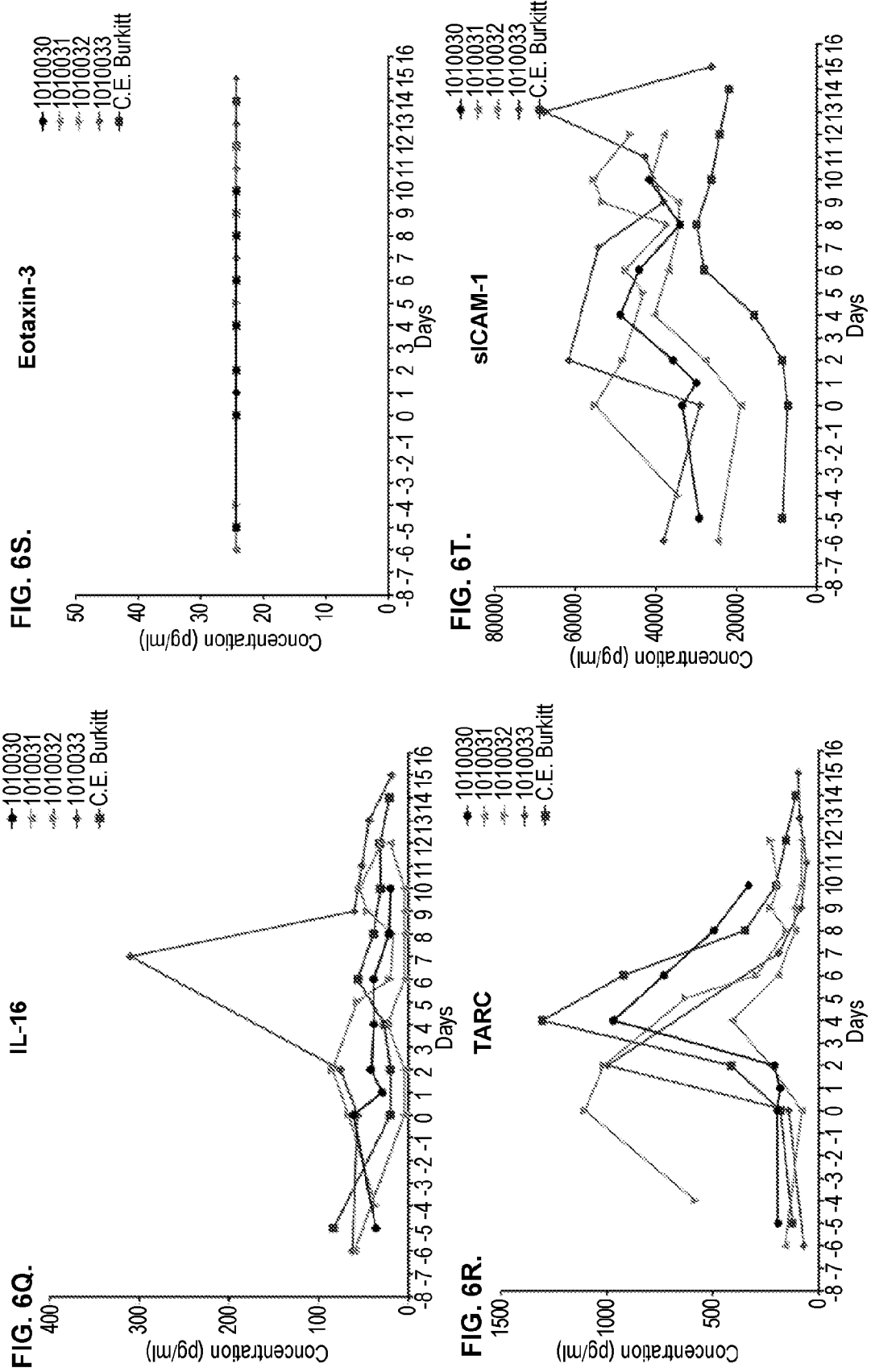

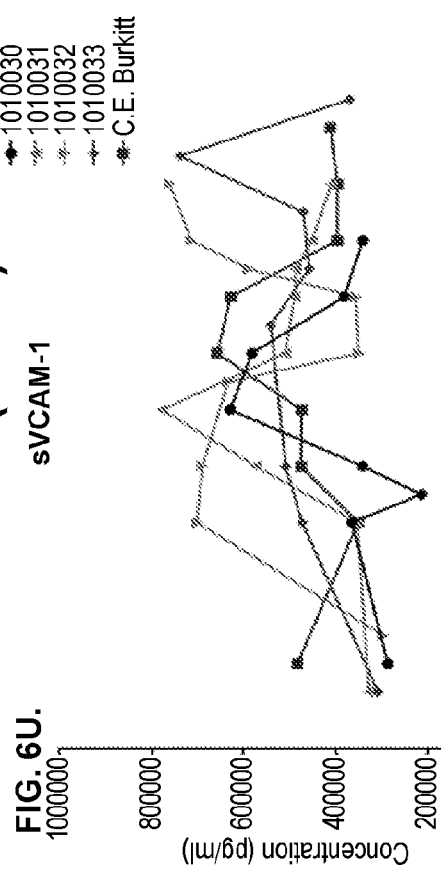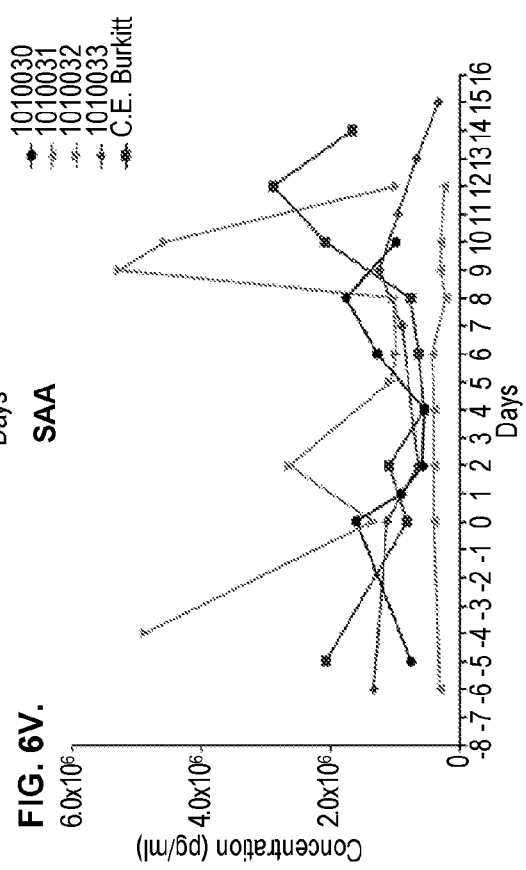
FIG. 6 (cont'd)

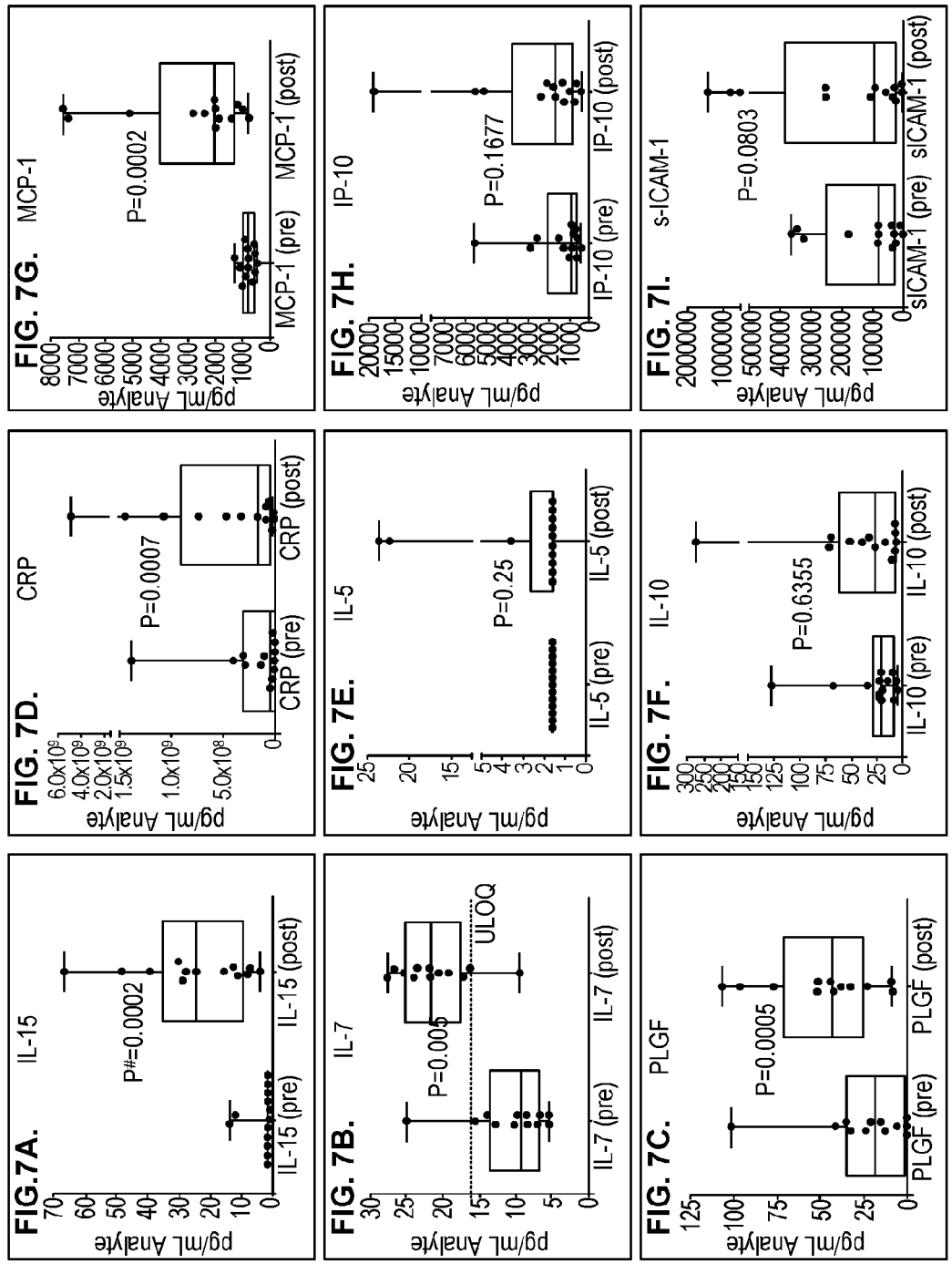
FIG. 7 – Serum Levels of select cytokines before and after conditioning with 300 mg/m2/day Cyclophosphamide and 30 mg/m2/day Fludarabine

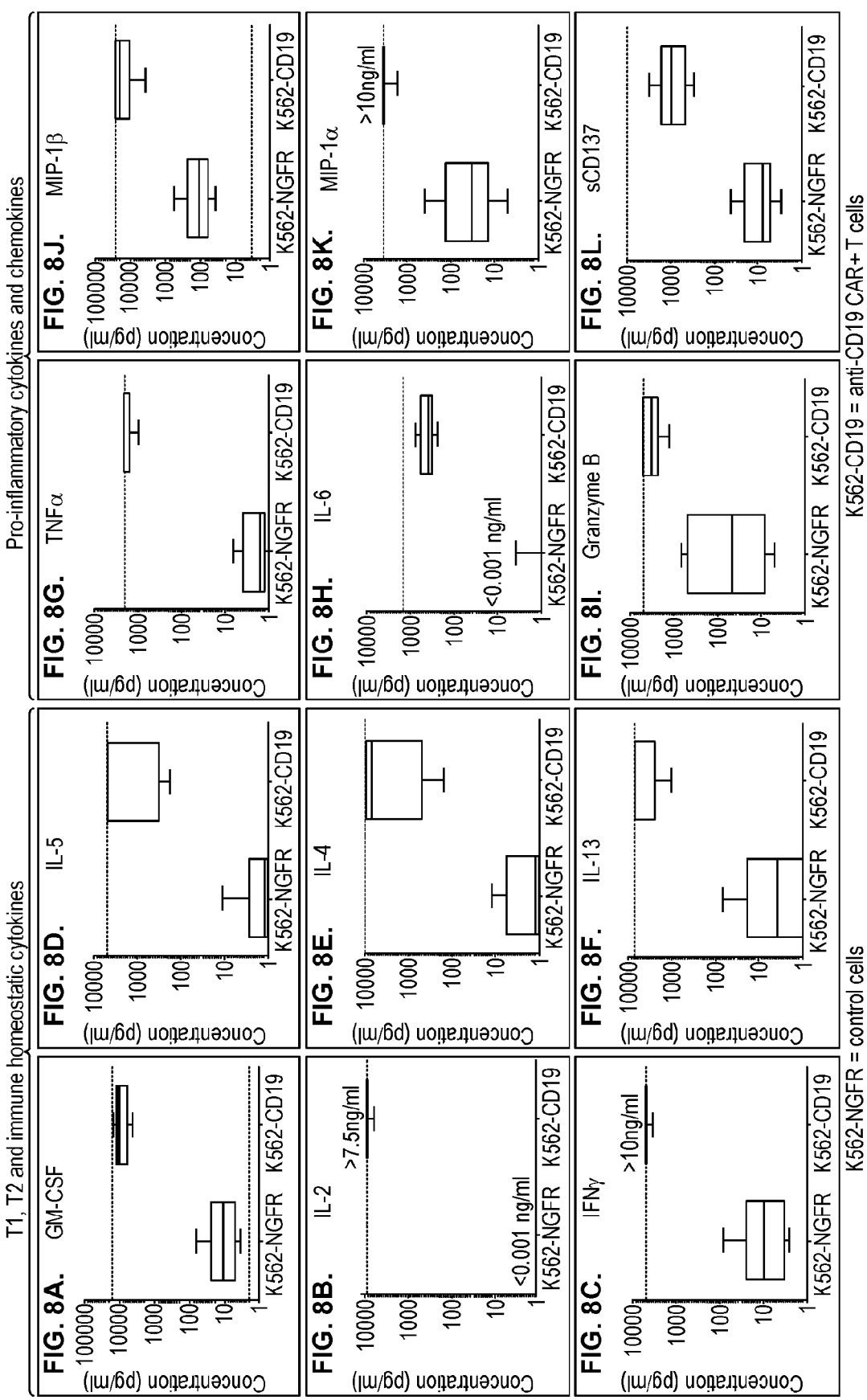
FIG. 8 – In vitro production of cytokines by anti-CD19 CAR+ T cells stimulated with K562 cells

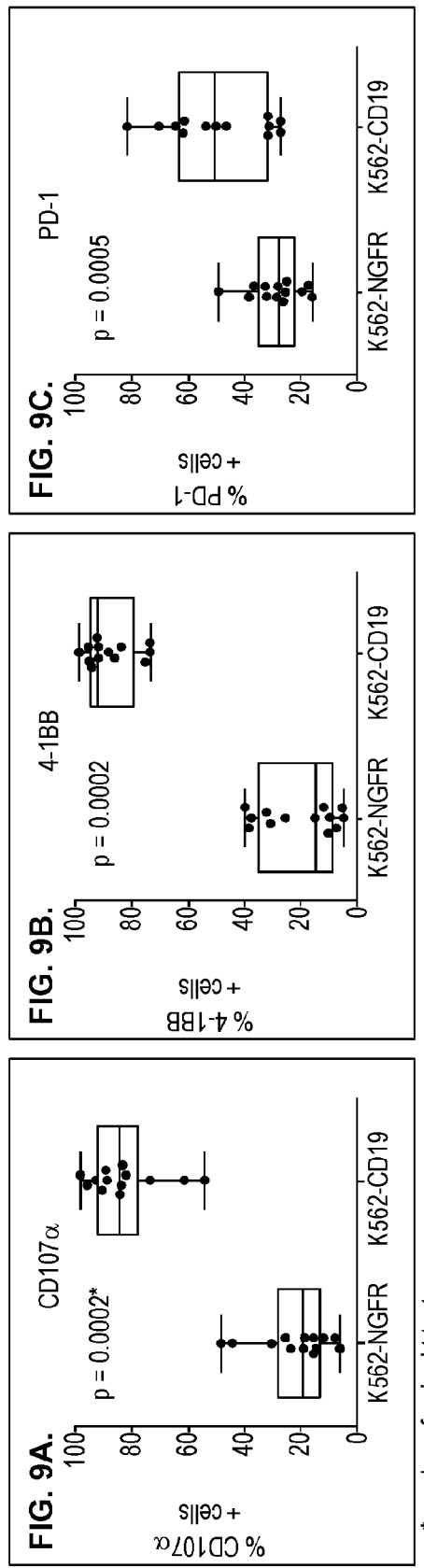
FIG. 9 – Induction of activating markers by anti-CD19 CAR+ T cells following engagement with target antigen

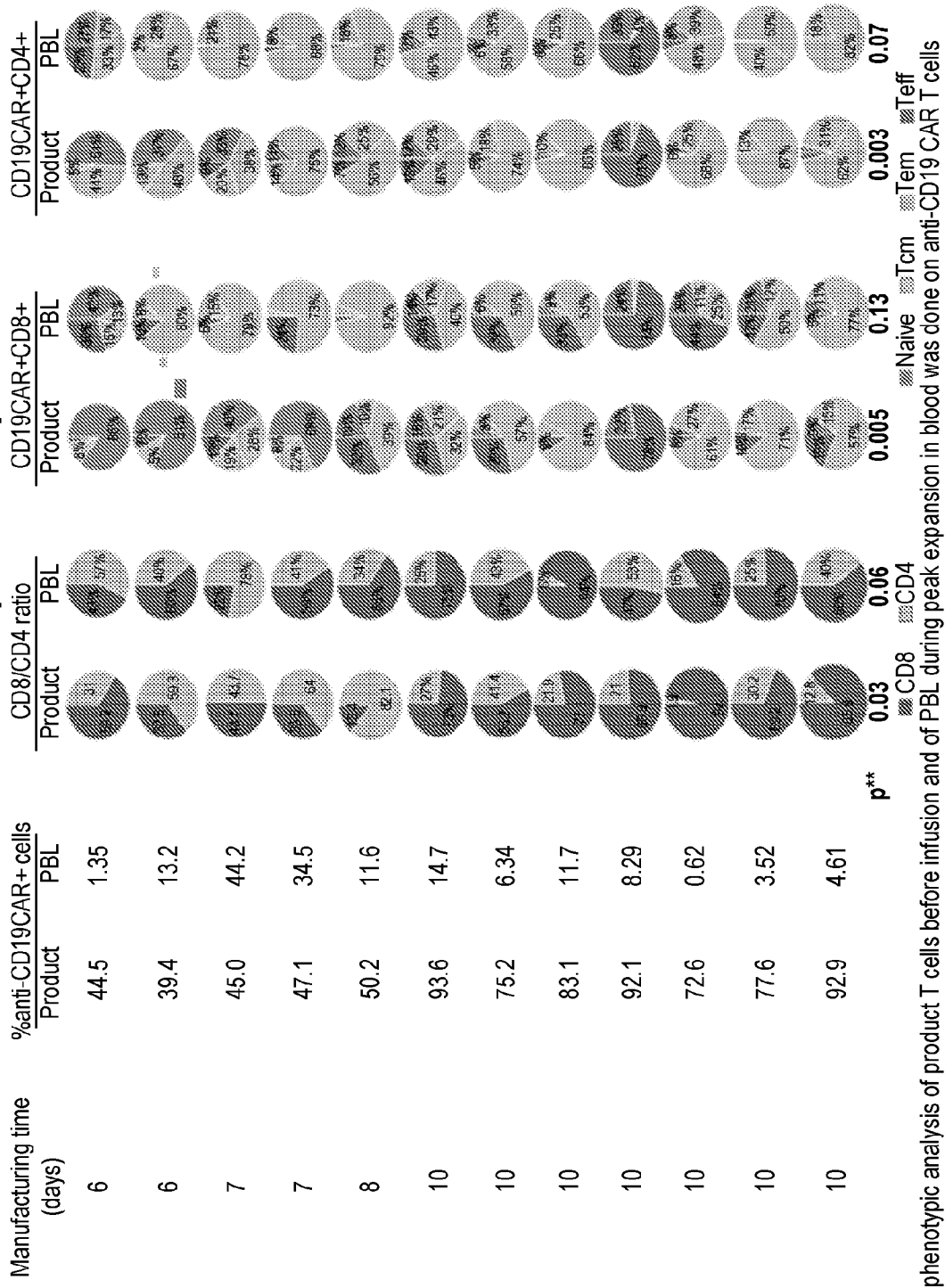

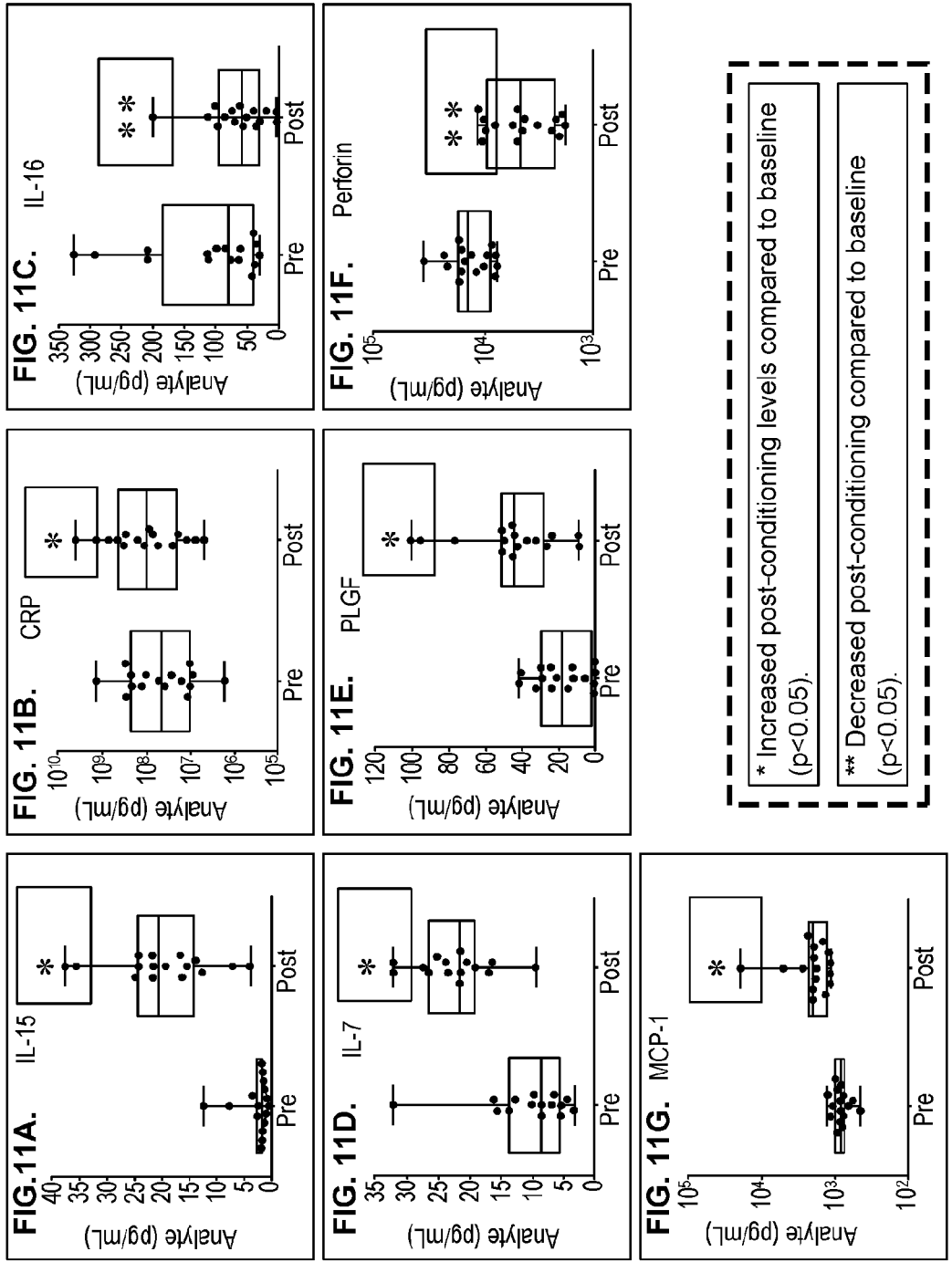
FIG. 11 – Expression profile of cytokines, chemokines and other markers observed following NHL patient conditioning

FIG. 12 – Quantification of Changes in Cytokines, Chemokines and Other Markers upon Conditioning with Cyclophosphamide and Fludarabine

| Marker[a] | Median fold change over baseline (Interquartile range) | % patients with increased levels over baseline (≥2x) | Pre vs post-conditioning Wilcoxon p-value |
|---|---|---|---|
| *Immune homeostatic* | | | |
| IL-15 ↑↑[b] | 14.8 (4.8, 21.8) | 81% | 0.0001 |
| IL-7 ↑[b] | 2.1 (1.7, 3) | 56% | 0.0001 |
| *Immune effector* | | | |
| PERFORIN ↓[c] | 0.3 (0.2, 0.5) | N/A | 0.0001 |
| *Inflammatory* | | | |
| CRP ↑[b] | 2.6 (1.2, 2.9) | 56% | 0.0034 |
| *Immune modulating* | | | |
| IL-16 ↓[c] | 0.8 (0.4, 0.9) | N/A | 0.0155 |
| *Chemokine* | | | |
| MCP-1 ↑[b] | 2 (1.6, 3.3) | 56% | 0.0001 |
| *Proangiogenic, Immune modulating* | | | |
| PLGF ↑[b] | 2.1 (1.2, 13.3) | 50% | 0.0002 |

[a] Markers were ordered within each category of biomarkers by low to high p-value using Wilcoxon signed-rank test. Those modified in a majority of patients and with p values of ≤0.05 were presented. Only 7 out of 41 measured markers showed changes in a majority of patients, associated with p≤0.05. Analysis was executed on markers measured prior to CAR T cell infusion.
[b] Markers increased over baseline (pre-conditioning values).
[c] Markers with levels decreased compared to baseline. N/A – not applicable.

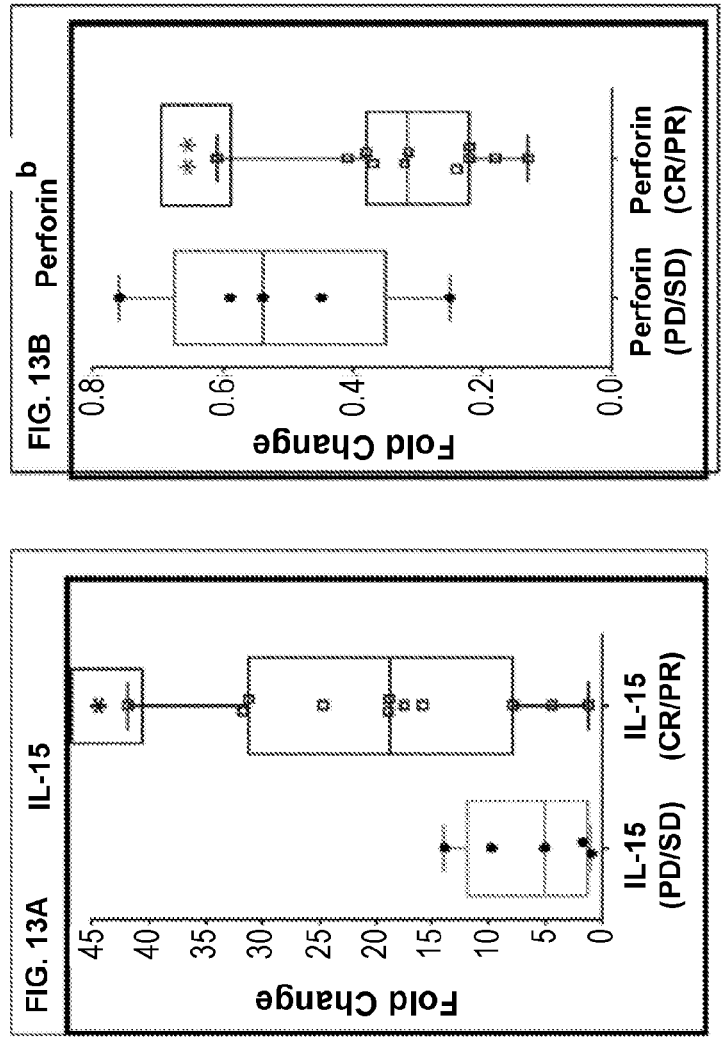

FIG. 13 – Magnitude of Change in Circulating IL-15 and Perforin Following Conditioning Chemotherapy Associated with Objective Response

[a] Wilcoxon rank-sum test utilized to compare fold change values (post vs. pre-conditioning) across responder vs non-responder groups.
[b] Conditioning also associated with diminution of circulating lymphocytes to undetectable levels at day 0.

\* Fold change post vs pre conditioning, positively associated with objective clinical response.
\*\* Fold change post vs pre conditioning, inversely associated with objective clinical response.

FIG. 14 – Biomarker Analysis of Cytokines, chemokines, and Effector Molecules

| Immune homeostatic cytokines | Inflammatory cytokines and markers | Immune modulating cytokines | Chemokines | Other markers |
|---|---|---|---|---|
| IL-15 | IL-6 | IL-13 | IL-8 | PLGF |
| IL-7 | IL-1α | IL-4 | MCP-1 | sICAM-1 |
| IL-2 | IL-1β | IL-5 | MCP-4 | sVCAM-1 |
| | IL-17α | IL-10 | MIP-1α | VEGF |
| Immune effectors | TNFα | IFNγ | MIP-1β | VEGF-C |
| Granzyme A | TNFβ | IL-12p40 | IP-10 | VEGF-D |
| Granzyme B | GM-CSF | IL-12p70 | TARC | FGF-2 |
| sFASL | CRP | IL-16 | Eotaxin | |
| Perforin | SAA | | Eotaxin-3 | |
| | | | MDC | |

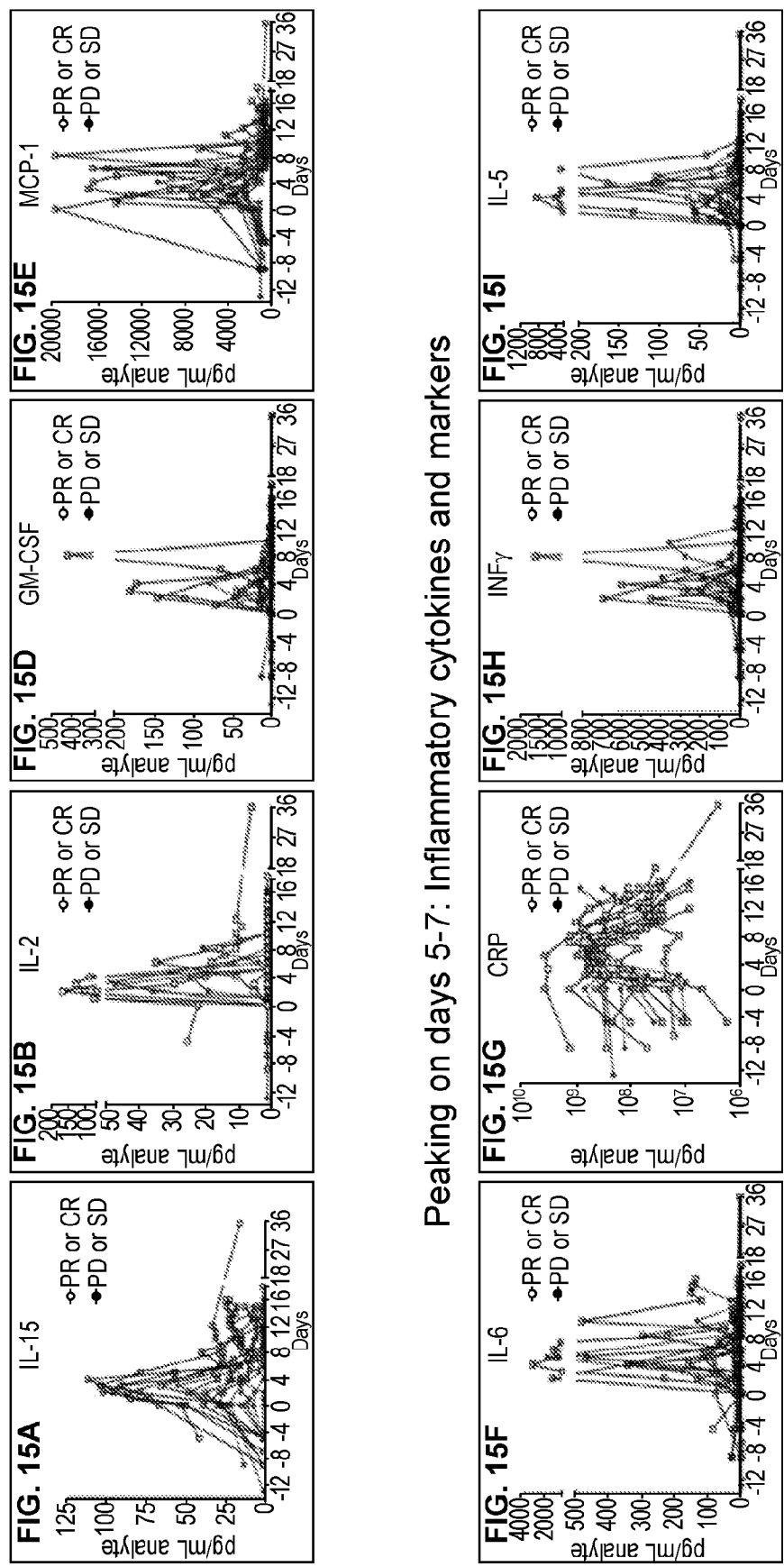
FIG. 15 – Sequential Induction and Clearance of Immune Homeostatic, Inflammatory, and Modulating Cytokines, Chemokines and Immune Effector Molecules

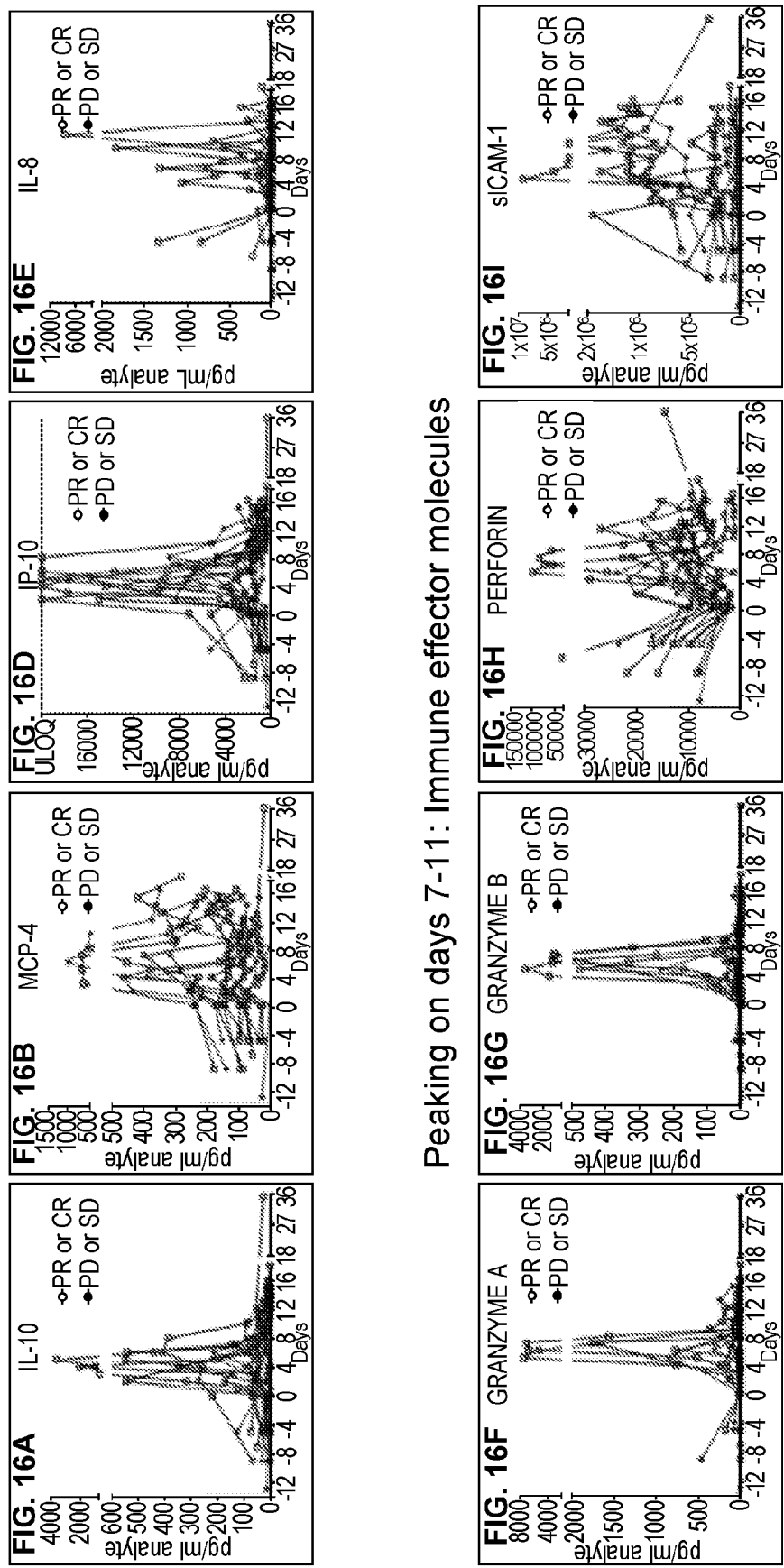
FIG. 16 – Sequential Induction and Clearance of Immune Homeostatic, Inflammatory, and Modulating Cytokines, Chemokines and Immune Effector Molecules

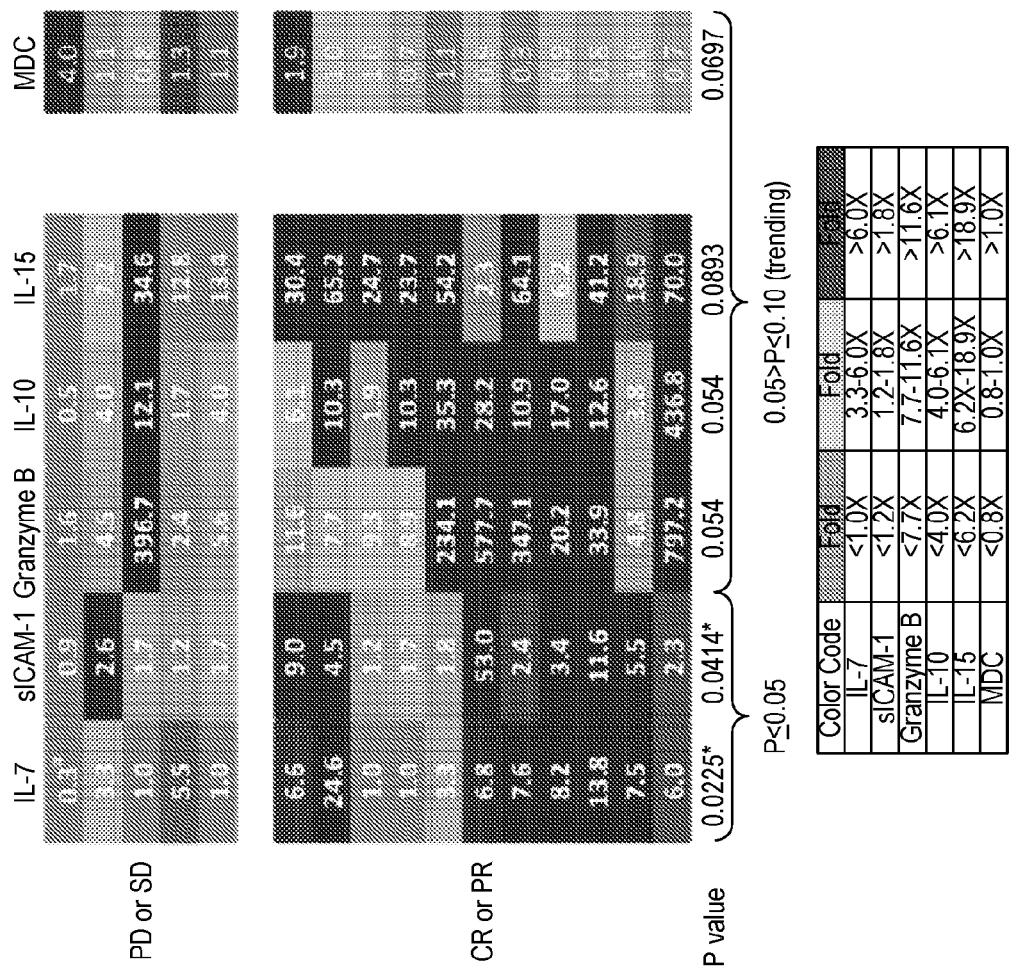
FIG. 17 – Change in treatment-related biomarkers and clinical response induced by anti-CD19 CAR T cells

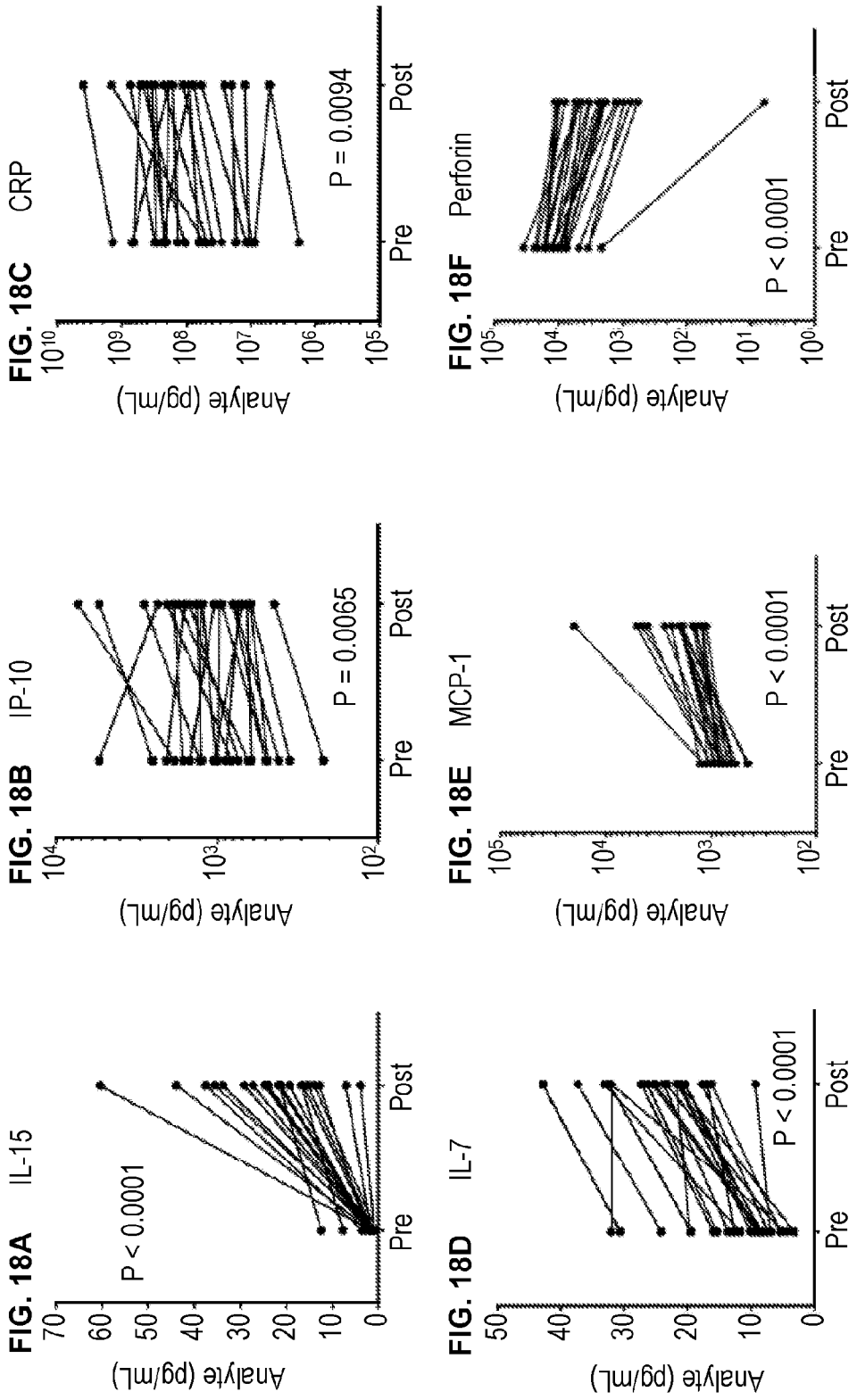

FIG. 18 – Low-Dose Conditioning Elevates Cytokines, Chemokines, Pro-inflammatory Markers, and Modulates Perforin Levels*

FIG. 18G

| Cytokine | Modulation by Conditioning (1: increase; -1 decrease) | Raw P-Value (2-sided Wilcoxon Signed Rank Test) | Multiple Testings (choose raw pvalues < 0.05 to enter into Holm's procedure) | Adjusted P-Value (Holm's procedure) |
|---|---|---|---|---|
| IL_15_ELISA | 1 | <.0001 | IL_15_ELISA | <.0001 |
| MCP_1 | 1 | <.0001 | MCP_1 | <.0001 |
| PERFORIN | -1 | <.0001 | PERFORIN | <.0001 |
| IL_7_ELISA | 1 | <.0001 | IL_7_ELISA | <.0001 |
| MDC | 1 | 0.0001 | MDC | 0.0012 |
| PLGF | -1 | 0.0006 | PLGF | 0.0064 |
| IL_16 | 1 | 0.0008 | IL_16 | 0.0068 |
| MCP_4 | -1 | 0.0016 | MCP_4 | 0.0124 |
| TNF_A | 1 | 0.0051 | TNF_A | 0.0354 |
| GRANZYME_B | -1 | 0.0061 | GRANZYME_B | 0.0366 |
| IP_10 | -1 | 0.0065 | IP_10 | 0.0366 |
| CRP | 1 | 0.0094 | CRP | 0.0375 |
| TARC | 1 | 0.0147 | TARC | 0.0441 |
| VEGF | -1 | 0.0305 | VEGF | 0.0610 |
| VEGF_C | -1 | 0.0494 | VEGF_C | 0.0610 |
| SVCAM_1 | 1 | 0.1095 | | |
| MIP_1B | -1 | 0.1429 | | |
| EOTAXIN | -1 | 0.1536 | | |
| MIP_1A | -1 | 0.2979 | | |
| VEGF_D | -1 | 0.478 | | |
| SICAM_1 | 1 | 0.6038 | | |
| IL_10 | -1 | 0.7337 | | |
| IL_8 | -1 | 0.7841 | | |
| IL_6 | 1 | 0.9341 | | |
| SAA | -1 | 0.9661 | | |
| IFNG | -1 | 1 | | |

FIG. 19 – Conditioning-related modulation of IL-15, IP-10 and Perforin
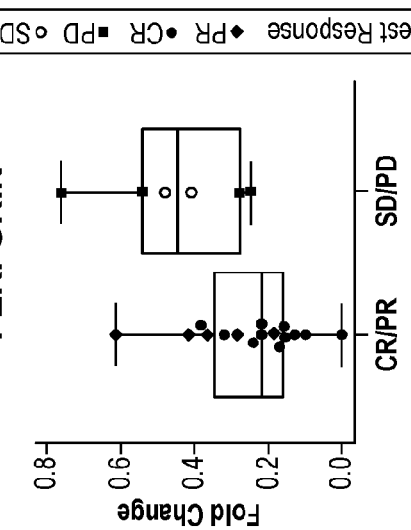
FIG. 19A IL-15 ELISA
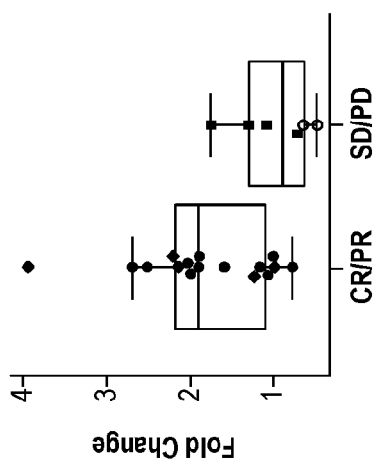
FIG. 19B IP-10
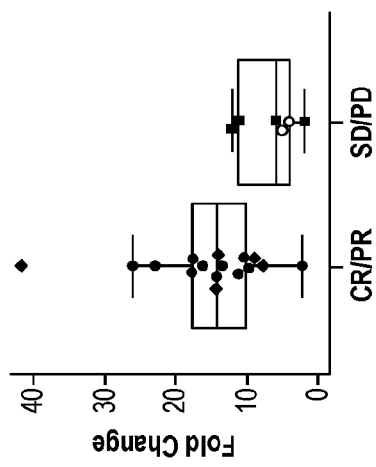
FIG. 19C PERFORIN
FIG. 19D
| Marker | Raw p-value | Adjusted p-value* |
|---|---|---|
| IL-15 ↑ | 0.0135 | 0.0405 |
| Perforin ↓ | 0.0202 | 0.0405 |
| IP-10 ↑ | 0.0245 | 0.0405 |
*A total of 41 biomarkers were analyzed; 3 showed significant association after Bonferroni step-down (Holm) multiplicity adjustment.

DIAGNOSTIC METHODS FOR T CELL THERAPY

STATEMENT OF GOVERNMENT INTEREST

This invention was made in the performance of a Cooperative Research and Development Agreement with the National Cancer Institute (NCI), an Agency of the Department of Health and Human Services. This invention was made with Government support under project number Z01BC010985 by the National Institutes of Health, National Cancer Institute. The Government of the United States has certain rights in this invention.

FIELD OF THE INVENTION

This invention relates to methods of identifying patients who are suitable for a T cell therapy or methods of preparing patients to be suitable for a T cell therapy by preconditioning the patients with one or more preconditioning agents capable of increasing the serum level of one or more cytokines that are indicative of the T cell therapy efficacy.

BACKGROUND OF THE INVENTION

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens can be used by the body's innate immune system to specifically target and kill cancer cells. However, cancer cells employ various mechanisms to prevent immune cells, such as T and B lymphocytes, from successfully targeting cancer cells.

Human T cell therapies rely on enriched or modified human T cells to target and kill cancer cells in a patient. Various technologies have been developed to enrich the concentration of naturally occurring T cells capable of targeting a tumor antigen or genetically modifying T cells to specifically target a known cancer antigen. These therapies have proven to have modest, though promising, effects on tumor size and patient survival. However, it has proven difficult to predict whether a given T cell therapy will be effective in each patient. Therefore, there is a need to identify a patient who would respond well to a T cell therapy or prepare a patient to respond well to a T cell therapy.

SUMMARY OF THE INVENTION

The present disclosure provides a method for treating a cancer in a patient suitable for a T cell therapy comprising (i) administering to the patient one or more preconditioning agents that are capable of increasing a serum level of interleukin-15 ("IL-15"), interleukin-7 ("IL-7"), and at least one additional cytokine selected from the group consisting of monocyte chemotactic protein 1 ("MCP-1"), C-reactive protein ("CRP"), placental growth factor ("PLGF"), interferon gamma-induced protein 10 ("IP-10"), and any combination thereof and (ii) administering a T cell therapy when the patient exhibits an increased serum level of IL-15, IL-7, and the at least one additional cytokine.

The present disclosure further provides a method for treating a cancer in a patient suitable for a T cell therapy comprising administering to the patient one or more preconditioning agents that are capable of increasing a serum level of IL-15, IL-7, and at least one additional cytokine selected from the group consisting of MCP-1, CRP, PLGF, IP-10, and any combination thereof, wherein the patient is treated with a T cell therapy when exhibiting an increased serum level of IL-15, IL-7, and the at least one additional cytokine.

The present disclosure also provides a method for treating a cancer in a patient suitable for a T cell therapy comprising (i) administering to the patient one or more preconditioning agents that are capable of increasing a serum level of IL-15, IL-7, and at least one additional cytokine selected from the group consisting of MCP-1, CRP, PLGF, IP-10, and any combination thereof, (ii) administering an additional amount of the one or more preconditioning agents or administering an effective amount of IL-15, IL-7, and the at least one additional cytokine selected from the group consisting of MCP-1, CRP, PLGF, IP-10, and any combination thereof, and (iii) administering a T cell therapy when the patient exhibits an increased serum level of IL-15, IL-7, and the at least one additional cytokine.

The present disclosure also provides a method for identifying a patient suitable for a T cell therapy comprising administering to the patient one or more preconditioning agents that are capable of increasing a serum level of IL-15, IL-7, and at least one additional cytokine selected from the group consisting of MCP-1, CRP, PLGF, IP-10, and any combination thereof.

The present disclosure also provides a method for identifying a patient suitable for a T cell therapy comprising (i) administering to the patient one or more preconditioning agents that are capable of increasing a serum level of IL-15, IL-7, and at least one additional cytokine selected from the group consisting of MCP-1, CRP, PLGF, IP-10, and any combination thereof and (ii) administering a T cell therapy when the patient exhibits an increased serum level of IL-15, IL-7, and the at least one additional cytokine.

The present disclosure also provides a method for identifying a patient suitable for a T cell therapy comprising (i) administering to the patient one or more preconditioning agents that are capable of increasing a serum level of IL-15, IL-7, and at least one additional cytokine selected from the group consisting of MCP-1, CRP, PLGF, IP-10, and any combination thereof, (ii) administering an additional amount of the one or more preconditioning agents or administering an effective amount of IL-15, IL-7, and the at least one additional cytokine selected from the group consisting of MCP-1, CRP, PLGF, IP-10, and any combination thereof, and (iii) administering a T cell therapy when the patient exhibits an increased serum level of IL-15, IL-7, and the at least one additional cytokine.

The present disclosure also provides a method for increasing a serum level of IL-15, IL-7, and at least one additional cytokine selected from the group consisting of MCP-1, CRP, PLGF, IP-10, and any combination thereof to pre-condition a patient in need of a T cell therapy comprising administering to the patient one or more preconditioning agents, wherein the patient is treated with a T cell therapy when exhibiting an increased serum level of IL-15, IL-7, and the at least one additional cytokine.

The present disclosure also provides a method for increasing a serum level of IL-15, IL-7, and at least one additional cytokine selected from the group consisting of MCP-1, CRP, PLGF, IP-10, and any combination thereof to pre-condition a patient in need of a T cell therapy comprising (i) administering to the patient one or more preconditioning agents and (ii) administering a T cell therapy when the patient exhibits an increased serum level of IL-15, IL-7, and the at least one additional cytokine.

The present disclosure also provides a method for increasing a serum level of IL-15, IL-7, and at least one additional cytokine selected from the group consisting of MCP-1, CRP, PLGF, IP-10, and any combination thereof to pre-condition a patient in need of a T cell therapy comprising (i) administering to the patient one or more preconditioning agents, (ii) administering an additional amount of the one or more preconditioning agents or administering an effective amount of IL-15, IL-7, and the at least one additional cytokine selected from the group consisting of MCP-1, CRP, PLGF, IP-10, and any combination thereof, and (iii) administering a T cell therapy when the patient exhibits an increased serum level of IL-15, IL-7, and the at least one additional cytokine.

In certain embodiments, the methods disclosed herein further comprise measuring the serum level of IL-15, IL-7, and the at least one cytokine after the administration of the one or more preconditioning agents.

In one particular embodiment, the one or more preconditioning agents disclosed herein comprise cyclophosphamide and a purine analog. In one embodiment, the purine analog is selected from pentostatin and fludarabine.

In certain embodiments, the T cell therapy is selected from the group consisting of tumor-infiltrating lymphocyte (TIL) immunotherapy, autologous cell therapy, engineered autologous cell therapy (eACT), allogeneic T cell transplantation, and any combination thereof.

BRIEF DESCRIPTION OF THE FIGURES

FIG. 1 shows a schematic representation of an example CAR-engineered T cell and its construction. In this exemplary CAR-engineered T cell, the target binding domain comprises an antibody derived scFv domain, the costimulatory domain is derived from CD28, and the essential activating domain is derived from CD3ζ (zeta). A CAR vector construct can be carried by a viral vector and then incorporated into a T cell genome. The CAR construct can then be expressed by the T cell as a transmembrane protein.

FIGS. 2A and 2B show patient disease responses following treatment with anti-CD-19 CAR+ T cells. The best responses of patients with B cell malignancies are shown in FIG. 2A as a percent change in disease condition. Dashed bars indicate a complete response (CR). Shaded bars indicate a partial response. White bars indicate a stable disease (SD). Black bars indicate progressive disease (PD). FIG. 2B shows patient disease responses relative to months post-CAR+ T cell infusion. Solid black bars indicate partial response (PR), and grey bars indicate complete response (CR). Breaks in the bars marked with "PD" indicate that the patient experienced a progressive disease. Inverted triangles mark the time of T cell infusion. Solid circles indicate the time of B cell recovery. White circles indicate the time of CAR+ T cell clearance from the patient's blood. A horizontal arrow indicates that the patient's response is ongoing.

FIGS. 4A-4H shows serum levels of selected cytokine analytes before and after conditioning with 300 mg/m$^2$/day cyclophosphamide and 30 mg/m$^2$/day fludarabine. The serum levels of interleukin 15 (IL-15; FIG. 4A), monocyte chemotactic protein 1 (MCP-1; FIG. 4B), gamma-induced protein 10 (IP-10; FIG. 4C), placental growth factor (PLGF; FIG. 4D), soluble intercellular adhesion molecule 1 (sICAM-1; FIG. 4E), C-reactive protein (CRP; FIG. 4F), vascular endothelial growth factor D (VEGF-D; FIG. 4G), and macrophage inflammatory protein 1β (MIP-1b; FIG. 4H) are shown pre-administration and post-administration of 300 mg/m$^2$ cyclophosphamide and 30 mg/m$^2$ fludarabine. Pre-administration serum was collected between day −12 and day −5, and post-administration serum was collected on day 0 prior to T cell therapy administration (FIGS. 4A-4H).

FIGS. 5A-H show the fold change in the serum levels of select cytokine analytes following conditioning with 300 mg/m$^2$/day cyclophosphamide and 30 mg/m$^2$/day fludarabine in patients who either responded or did not respond to subsequence T cell therapy. The fold change in the serum levels of IL-15 (FIG. 5A), MCP-1 (FIG. 5B), IP-10 (FIG. 5C), PLGF (FIG. 5D), sICAM-1 (FIG. 5E), CRP (FIG. 5F), VEGF (FIG. 5G), and MIP-1b (FIG. 5H) are shown for responders and non-responders. Horizontal lines indicate the average (FIGS. 5A-H). Individual patient IL-15 changes are shown in FIG. 5A, and each patient's disease responsiveness is indicated next to each data point as a partial response (PR), complete response (CR), stable disease (SD), or progressive disease (PD) (FIG. 5A).

FIGS. 6A-6V show the serum concentration of select cytokine analytes measured at various time points from day −10 to day 18 for patients administered 300 mg/m$^2$/day cyclophosphamide and 30 mg/m$^2$/day fludarabine prior to receiving a T cell therapy on day 0. The serum concentration of granulocyte macrophage colony-stimulating factor (GM-CSF; FIG. 6A), IL-2 (FIG. 6B), MCP-1 (FIG. 6C), IL-6 (FIG. 6D), IL-10 (FIG. 6E), MCP-4 (FIG. 6F), CRP (FIG. 6G), interferon gamma (IFNγ; FIG. 6H), granzyme A (FIG. 6I), IL-15 (FIG. 6J), IL-5 (FIG. 6K), granzyme B (FIG. 6L), IL-8 (FIG. 6M), IP-10 (FIG. 6N), MIP-1b (FIG. 6O), PLGF (FIG. 6P), IL-16 (FIG. 6Q), thymus and activation regulated chemokine (TARC; FIG. 6R), eotaxin-3 (FIG. 6S), sICAM-1 (FIG. 6T), soluble vascular adhesion molecule 1 (sVCAM; FIG. 6U), and (SAA; FIG. 6V) are shown.

FIGS. 7A-7I show the serum concentration of selected cytokine analytes measured pre- and post-administration of 300 mg/m$^2$/day cyclophosphamide and 30 mg/m$^2$/day fludarabine. Post-administration sera were collected right before T cell infusion. The serum concentrations of IL-15 (FIG. 7A), IL-7 (FIG. 7B), PLGF (FIG. 7C), CRP (FIG. 7D), IL-5 (FIG. 7E), IL-10 (FIG. 7F), MCP-1 (FIG. 7G), IP-10 (FIG. 7H), and sICAM-1 (FIG. 7I) are shown. Each data point represents a single patient. Horizontal bars show the average (FIGS. 7A-7I). P value of Wilcoxon matched-pairs signed rank test was applied to analytes measured preconditioning and postconditioning, and corresponding P values are shown (FIGS. 7A-7I). Some IL-7 values were above the upper limit of quantitation (ULOQ; FIG. 7B).

FIGS. 8A-8L shows the in vitro production of various cytokine analytes produced by anti-CD19 CAR+ T cells (K562-CD19) as compared to a negative control (K562-NGFR) following stimulation with K562 cells. The concentrations of GM-CSF (FIG. 8A), IL-2 (FIG. 8B), IFNγ (FIG. 8C), IL-5 (FIG. 8D), IL-4 (FIG. 8E), IL-13 (FIG. 8F), tumor necrosis factor alpha (TNFα; FIG. 8G), IL-6 (FIG. 8H), granzyme B (FIG. 8I), MIP-1β (FIG. 8J), MIP-1α (FIG. 8K), and soluble CD137 (FIG. 8L) are shown for control and anti-CD19 CAR+ T cells. T1, T2, and immune homeostatic cytokines (FIGS. 8A-8F) and pro-inflammatory cytokines and chemokines (FIGS. 8G-8L) are labeled accordingly. Data was collected pre-infusion by co-incubating product T cells with K562-CD19 or control K562-NGFR cells and measuring the concentration of the listed analytes in the medium (FIGS. 8A-8L).

FIGS. 9A-9C shows the percent of anti-CD19 CAR+ T cells (K562-CD19) expressing various cytokines following engagement with a target antigen as compared to a negative control (K562-NGFR). The percent of cells expressing CD107α (FIG. 9A), 4-1BB (FIG. 9B), and programmed death 1 (PD-1; FIG. 9C) are shown. Data was collected pre-infusion by co-incubating product T cells with K562-CD19 or control K562-NGFR cells and measuring the concentration of the select activating markers in the medium (FIGS. 9A-9C). P values shown indicate the results of a paired T test comparing K562-CD19 test cells with K562-NGFR negative control cells (FIGS. 9A-9C).

FIG. 10 illustrates the various characteristics of the product T cells and peripheral blood lymphocytes (PBLs) in view of the manufacturing time (days). The data include the percent of anti-CD-19 CAR+ T cells detected in the product versus the PBL; the ratio of CD8 to CD4 in the product versus the PBL; the relative occurrence of naïve, central memory (Tcm), effector memory (Tem), and effector (Teff) T cells within the anti-CD19 CAR+ CD8+ T cell population; and the relative occurrence of naïve, central memory (Tcm), effector memory (Tem), and effector (Teff) T cells within the anti-CD19 CAR+ CD4+ T cell population (FIG. 10). The phenotypic analysis of product T cells before infusion and PBL during peak expansion in blood was done on anti-CD19 CAR+ T cells (FIG. 10). The p-value represents the results of a rank test of association between manufacturing time and T cell subset composition.

FIG. 11 shows expression profile of cytokines, chemokines and other markers observed following NHL patient conditioning according to the invention. CRP: C reactive protein. PLGF: Placental growth factor. MCP-1: Monocyte chemoattractant protein-1.

FIG. 12 sets forth quantification of changes observed in cytokines, chemokines and other markers following Conditioning with Cyclophosphamide and Fludarabine according to the invention.

FIG. 13 shows the magnitude of change in circulating IL-15 and perforin following conditioning chemotherapy associated with objective response. P values were not adjusted for multiplicity. Analysis executed on markers measured prior to CAR T cell infusion.

FIG. 14 sets forth a biomarker analysis of cytokines, chemokines, and effector molecules. Markers were ordered within each category of biomarkers by low to high p-value using Wilcoxon signed-rank test. Those modified in a majority of patients and with p values of <0.05 were presented. Only 7 out of 41 measured markers showed changes in a majority of patients, associated with p<0.05. Analysis was executed on markers measured prior to CAR T cell infusion.

FIG. 15 sets forth sequential induction and clearance of immune homeostatic, inflammatory, and modulating cytokines, chemokines and immune effector molecules. Representative markers are shown. A total of 22 out of 41 measured markers showed an elevation post CAR T-cell treatment in at least 50% of the patients, at least 2-fold higher than baseline values: IL-15, IL-7, IL-2, Granzyme B, Granzyme A, CRP, IL-6, GM-CSF, IL-5, IFNg, IL-10, MCP-1, MCP-4, IP-10, IL-8, TARC, MIP1a, MIP1b, PLGF, VEGF-D, sICAM-1 and FGF-2. Peaking observed on days 3-4 for immune homeostatic cytokines & chemokines.

FIG. 16 sets forth the sequential induction and clearance of immune homeostatic, inflammatory, and modulating cytokines, chemokines and immune effector molecules. Representative markers are shown. A total of 22 out of 41 measured markers showed elevation post CAR T cell treatment in at least 50% of the patients, at least 2-fold higher than baseline values: IL-15, IL-7, IL-2, Granzyme B, Granzyme A, CRP, IL-6, GM-CSF, IL-5, IFNg, IL-10, MCP-1, MCP-4, IP-10, IL-8, TARC, MIP1a, MIP1b, PLGF, VEGF-D, sICAM-1 and FGF-2. Peaking was observed on days 5-7 for immune modulating cytokines and chemokines. "ULOQ": upper limit of quantitation.

FIG. 17 shows the change in treatment-related biomarkers and clinical response induced by anti-CD19 CAR T cells according to the invention. Maximum fold change of marker levels post-CAR T cell treatment versus baseline (preconditioning). Each line represents an individual subject. The Wilcoxon rank-sum test was used to compare the maximum fold change values across responder vs non-responder groups, for all 41 biomarkers evaluated. P-values were not adjusted for multiplicity, and only those biomarkers with p<0.10 were shown: p values for IL-7 and sICAM-1 were <0.05. The association was also applicable to changes in absolute levels of IL-7 (p=0.0165), IL-15 (p=0.0314) and IL-15 (p=0.041).

FIGS. 18A-18G show the change in the level of analytes before and after conditioning with cyclophosphamide and fludarabine. FIGS. 18A-18F show the pre and post levels of IL-15 (FIG. 18A), IP-10 (FIG. 18B), CRP (FIG. 18C), IL-7 (FIG. 18D), MCP-1 (FIG. 18E), and perforin (FIG. 18F). FIG. 18G summarizes the change in serum levels of various analytes and the corresponding p values.

FIG. 19A-19E shows the correlation between change in analyte level after conditioning and the objective response to CAR T cell therapy for IL-15 (FIG. 19A), IP-10 (FIG. 19B), and perforin (FIG. 19C). FIG. 19D provides a summary of the statistical significance of the data provided in each of FIGS. 19A-19C.

DETAILED DESCRIPTION OF THE INVENTION

Figure 3:
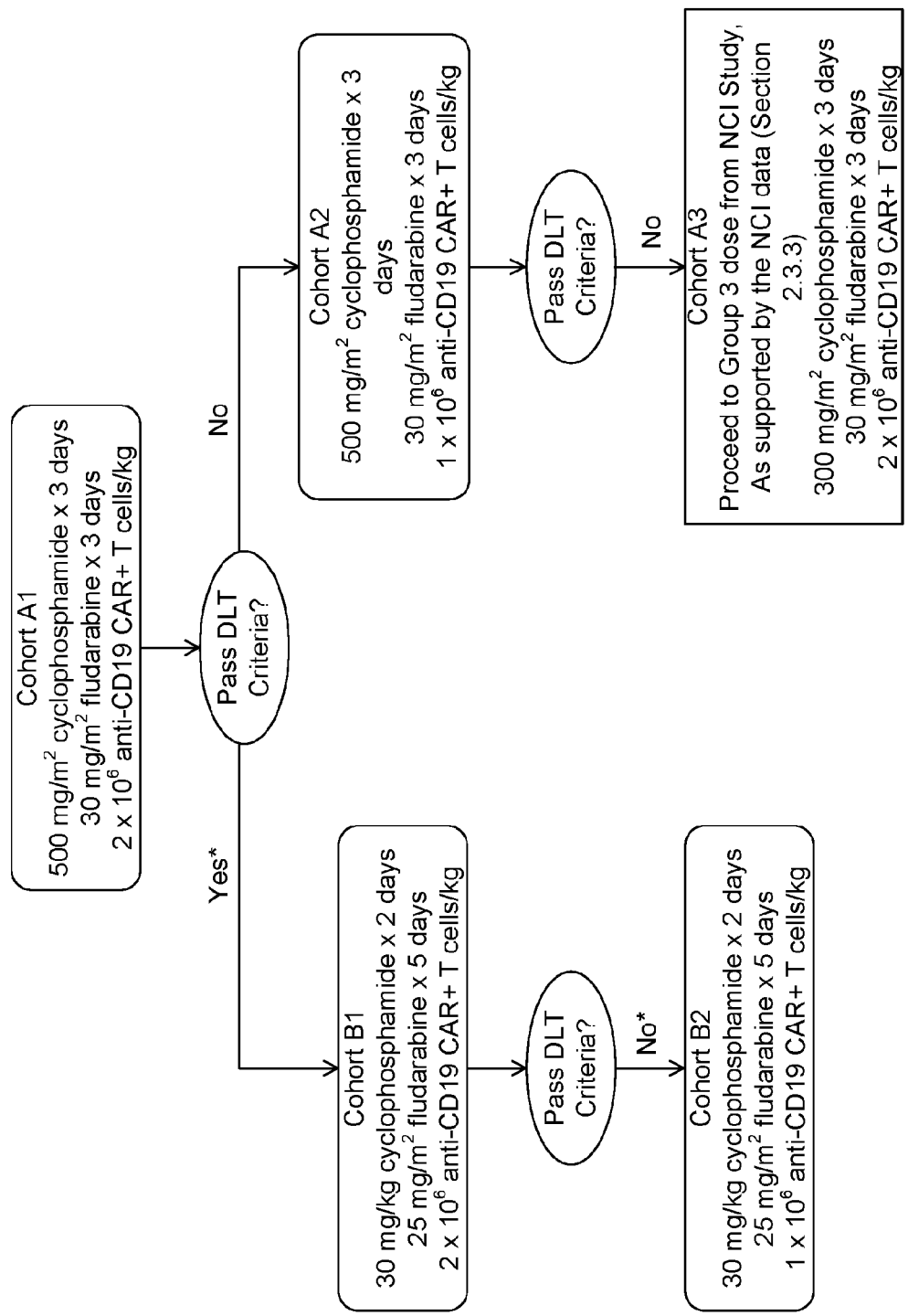
FIG. 3 provides a sample diagram of a phase 1 clinical trial directed to determining the safety, efficacy, and dose limiting toxicities of treating a patient with 500 mg/m$^2$/day cyclophosphamide, 30 mg/m$^2$/day fludarabine, and 2×10$^6$ anti-CD19 CAR+ T cells/kg.

The present invention relates to methods of identifying a patient suitable for a T cell therapy, e.g., an engineered CAR T cell therapy, e.g., an autologous cell therapy (eACT™), and then treating the patient with a T cell therapy. Therefore, the method comprises preconditioning the patient by administering one or more preconditioning agents capable of increasing the serum level of certain cytokines, e.g., IL-15, IL-7, and at least one additional biomarker cytokine. Preconditioning patients prior to T cell therapies with the one or more preconditioning agents improves the efficacy of the T cell therapy by reducing the number of endogenous lymphocytes and increasing the serum level of homeostatic cytokines and/or pro-immune factors present in the patient, including IL-15 and IL-7. This creates a more optimal microenvironment for the transplanted T cells to proliferate once administered to the patient.

The present invention further relates to methods of creating a more suitable environment for a T cell therapy in a patient in need thereof, comprising (i) administering to the patient one or more preconditioning agent capable of increasing the serum level of certain cytokines, e.g., IL-15, IL-7, and at least one additional biomarker cytokine; (ii) administering to the patient one or more cytokines identified to be associated with increased effectiveness of a T cell therapy, e.g., IL-15, IL-7, and at least one additional biomarker cytokine; or (iii) administering to the patient an additional treatment, e.g., additional cytokines, an additional dose of the one or more preconditioning agent, or T cells engineered to express one or more cytokines, wherein the additional treatment increases the serum level of the one or more cytokines identified to be associated with increased effectiveness of a T cell therapy, e.g., IL-15, IL-7, and at least one additional biomarker cytokine.

Definitions

In order that the present disclosure may be more readily understood, certain terms are first defined. As used in this application, except as otherwise expressly provided herein, each of the following terms shall have the meaning set forth below. Additional definitions are set forth throughout the application.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Systeme International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

The term "activation" refers to the state of an immune cell, e.g., a T cell, that has been sufficiently stimulated to induce detectable cellular proliferation. Activation can also be associated with induced cytokine production and detectable effector functions. The term "activated T cells" refers to, among other things, T cells that are undergoing cell division.

"Administering" refers to the physical introduction of an agent to a subject, using any of the various methods and delivery systems known to those skilled in the art. Exemplary routes of administration for the formulations disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the formulation is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

An "adverse event" (AE) as used herein is any unfavorable and generally unintended or undesirable sign (including an abnormal laboratory finding), symptom, medical occurrence, or disease associated with the use of a medical treatment. The definition of adverse events includes worsening of a pre-existing medical condition. Worsening indicates that a pre-existing medical condition has increased in severity, frequency, and/or duration or has an association with a worse outcome.

The term "antibody" (Ab) includes, without limitation, a glycoprotein immunoglobulin which binds specifically to an antigen. In general, and antibody can comprise at least two heavy (H) chains and two light (L) chains interconnected by disulfide bonds, or an antigen-binding portion thereof. Each H chain comprises a heavy chain variable region (abbreviated herein as VH) and a heavy chain constant region. The heavy chain constant region comprises three constant domains, CH1, CH2 and CH3. Each light chain comprises a light chain variable region (abbreviated herein as VL) and a light chain constant region. The light chain constant region is comprises one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the Abs may mediate the binding of the immunoglobulin to host tissues or factors, including various cells of the immune system (e.g., effector cells) and the first component (C1q) of the classical complement system.

An immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or nonhuman Abs; wholly synthetic Abs; and single chain Abs. A nonhuman Ab may be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain Ab.

An "antigen binding molecule" or "antibody fragment" refers to any portion of an antibody less than the whole. An antigen binding molecule can include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules.

An "antigen" refers to any molecule that provokes an immune response or is capable of being bound by an antibody. The immune response may involve either antibody production, or the activation of specific immunologically-competent cells, or both. A person of skill in the art would readily understand that any macromolecule, including virtually all proteins or peptides, can serve as an antigen. An antigen can be endogenously expressed, i.e. expressed by genomic DNA, or can be recombinantly expressed. An antigen can be specific to a certain tissue, such as a cancer cell, or it can be broadly expressed. In addition, fragments of larger molecules can act as antigens. In one embodiment, antigens are tumor antigens.

The term "autologous" refers to any material derived from the same individual to which it is later to be re-introduced. For example, the engineered autologous cell therapy (eACT™) method described herein involves collection of lymphocytes from a patient, which are then engineered to express, e.g., a CAR construct, and then administered back to the same patient.

The term "allogeneic" refers to any material derived from one individual which is then introduced to another individual of the same species, e.g., allogeneic T cell transplantation.

A "cancer" refers to a broad group of various diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. A "cancer" or "cancer tissue" can include a tumor. Examples of cancers that can be treated by the methods of the present invention include, but are not limited to, cancers of the immune system including lymphoma, leukemia, and other leukocyte malignancies. In some embodiments, the methods of the present invention can be used to reduce the tumor size of a tumor derived from, for example, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and combinations of said cancers. The particular cancer can be responsive to chemo- or radiation therapy or the cancer can be refractory. A refractor cancer refers to a cancer that is not amendable to surgical intervention and the cancer is either initially unresponsive to chemo- or radiation therapy or the cancer becomes unresponsive over time.

An "anti-tumor effect" as used herein, refers to a biological effect that can present as a decrease in tumor volume, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

The term "progression-free survival," which can be abbreviated as PFS, as used herein refers to the time from the treatment date to the date of disease progression per the revised IWG Response Criteria for Malignant Lymphoma or death from any cause.

"Disease progression" is assessed by measurement of malignant lesions on radiographs or other methods should not be reported as adverse events. Death due to disease progression in the absence of signs and symptoms should be reported as the primary tumor type (e.g., DLBCL).

The "duration of response," which can be abbreviated as DOR, as used herein refers to the period of time between a subject's first objective response to the date of confirmed disease progression, per the revised IWG Response Criteria for Malignant Lymphoma, or death.

The term "overall survival," which can be abbreviated as OS, is defined as the time from the date of treatment to the date of death.

A "cytokine," as used herein, refers to a non-antibody protein that is released by one cell in response to contact with a specific antigen, wherein the cytokine interacts with a second cell to mediate a response in the second cell. A cytokine can be endogenously expressed by a cell or administered to a subject. Cytokines may be released by immune cells, including macrophages, B cells, T cells, and mast cells to propagate an immune response. Cytokines can induce various responses in the recipient cell. Cytokines can include homeostatic cytokines, chemokines, pro-inflammatory cytokines, effectors, and acute-phase proteins. For example, homeostatic cytokines, including interleukin (IL) 7 and IL-15, promote immune cell survival and proliferation, and pro-inflammatory cytokines can promote an inflammatory response. Examples of homeostatic cytokines include, but are not limited to, IL-2, IL-4, IL-5, IL-7, IL-10, IL-12p40, IL-12p70, IL-15, and interferon (IFN) gamma. Examples of pro-inflammatory cytokines include, but are not limited to, IL-1a, IL-1b, IL-6, IL-13, IL-17a, tumor necrosis factor (TNF)-alpha, TNF-beta, fibroblast growth factor (FGF) 2, granulocyte macrophage colony-stimulating factor (GM-CSF), soluble intercellular adhesion molecule 1 (sICAM-1), soluble vascular adhesion molecule 1 (sVCAM-1), vascular endothelial growth factor (VEGF), VEGF-C, VEGF-D, and placental growth factor (PLGF). Examples of effectors include, but are not limited to, granzyme A, granzyme B, soluble Fas ligand (sFasL), and perforin. Examples of acute phase-proteins include, but are not limited to, C-reactive protein (CRP) and serum amyloid A (SAA).

"Chemokines" are a type of cytokine that mediates cell chemotaxis, or directional movement. Examples of chemokines include, but are not limited to, IL-8, IL-16, eotaxin, eotaxin-3, macrophage-derived chemokine (MDC or CCL22), monocyte chemotactic protein 1 (MCP-1 or CCL2), MCP-4, macrophage inflammatory protein 1α (MIP-1α, MIP-1a), MIP-1β (MIP-1b), gamma-induced protein 10 (IP-10), and thymus and activation regulated chemokine (TARC or CCL17).

Other examples of analytes and cytokines of the present invention include, but are not limited to chemokine (C-C motif) ligand (CCL) 1, CCL5, monocyte-specific chemokine 3 (MCP3 or CCL7), monocyte chemoattractant protein 2 (MCP-2 or CCL8), CCL13, IL-1, IL-3, IL-9, IL-11, IL-12, IL-14, IL-17, IL-20, IL-21, granulocyte colony-stimulating factor (G-CSF), leukemia inhibitory factor (LIF), oncostatin M (OSM), CD154, lymphotoxin (LT) beta, 4-1BB ligand (4-1BBL), a proliferation-inducing ligand (APRIL), CD70, CD153, CD178, glucocorticoid-induced TNFR-related ligand (GITRL), tumor necrosis factor superfamily member 14 (TNFSF14), OX40L, TNF- and ApoL-related leukocyte-expressed ligand 1 (TALL-1), or TNF-related apoptosis-inducing ligand (TRAIL).

The terms "serum level" and "serum concentration" are used interchangeably as used herein and refer to the amount of an analyte in the serum of a subject. Serum levels of a given analyte can be measured using any method known in the art. For example, cytokine serum levels can be measured using an enzyme-linked immunosorbent assay (ELISA). In one particular embodiment, cytokine serum levels can be measured using an EMDmillipore LUMINEX® xMAP® multiplex assay.

"Dosing interval," as used herein, means the amount of time that elapses between multiple doses of a formulation disclosed herein being administered to a subject. Dosing interval can thus be indicated as ranges.

Doses described herein can be presented as a "weight based dose" or as a "body surface area (BSA) based dose." A weight based dose is a dose that is administered to a patient that is calculated based on the weight of the patient, e.g., mg/kg. A BSA based dose is a dose that is administered to a patient that is calculated based on the surface area of the patient, e.g., mg/m². The two forms of dose measurement can be converted for human dosing by multiplying the weight based dose by 37 or dividing the BSA based dose by 37. For example, a dose of 60 mg/kg cyclophosphamide to be administered to a human subject is equivalent to a 2220 mg/m² dose of the same drug to be administered to the same subject.

The term "dosing frequency" as used herein refers to the frequency of administering doses of a formulation disclosed herein in a given time. Dosing frequency can be indicated as the number of doses per a given time. For example, a preconditioning agent, e.g, cyclophosphamide, can be administered as a single dose per day on each of 5 consecutive days, as a single dose per day on each of 4 consecutive days, as a single dose per day on each of 3 consecutive days, as a single dose per day on each of 2 consecutive days, or as a single dose on 1 day. In addition, a second preconditioning agent, e.g., fludarabine, can be administered as a single dose per day on each of 8 consecutive days, as a single dose per day on each of 7 consecutive days, as a single dose per day on each of 6 consecutive days, as a single dose per day on each of 5 consecutive days, as a single dose per day on each of 4 consecutive days, as a single dose per day on each of 3 consecutive days, as a single dose per day on each of 2 consecutive days, or as a single dose on 1 day. In other embodiments, the fludarabine is administered as 1 dose per day for 5 consecutive days or as 1 dose per day for 3 consecutive days.

A "therapeutically effective amount," "effective dose," "effective amount," or "therapeutically effective dosage" of a drug, a preconditioning agent, or a therapeutic agent, e.g., engineered CAR T cells, is any amount of the drug that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

The term "lymphocyte" as used herein includes natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). Its T-cell receptors (TCR) differentiate themselves from other lymphocyte types. The thymus, a specialized organ of the immune system, is primarily responsible for the T cell's maturation. There are six types of T-cells, namely: Helper T-cells (e.g., CD4+ cells), Cytotoxic T-cells (also known as TC, cytotoxic T lymphocyte, CTL, T-killer cell, cytolytic T cell, CD8+ T-cells or killer T cell), Memory T-cells ((i) stem memory $T_{SCM}$ cells, like naive cells, are CD45RO−, CCR7+, CD45RA+, CD62L+ (L-selectin), CD27+, CD28+ and IL-7Rα+, but they also express large amounts of CD95, IL-2Rβ, CXCR3, and LFA-1, and show numerous functional attributes distinctive of memory cells); (ii) central memory $T_{CM}$ cells express L-selectin and the CCR7, they secrete IL-2, but not IFNγ or IL-4, and (iii) effector memory $T_{EM}$ cells, however, do not express L-selectin or CCR7 but produce effector cytokines like IFNγ and IL-4), Regulatory T-cells (Tregs, suppressor T cells, or CD4+CD25+ regulatory T cells), Natural Killer T-cells (NKT) and Gamma Delta T-cells. B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

The term "genetically engineered" or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which can either be obtained from a patient or a donor. The cell can be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT), and allogeneic T cell transplantation. However, one of skill in the art would recognize that the conditioning methods disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The T cells of the immunotherapy can come from any source known in the art. For example, T cells can be differentiated in vitro from a hematopoietic stem cell population, or T cells can be obtained from a subject. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. Additional methods of isolating T cells for a T cell therapy are disclosed in U.S. Patent Publication No. 2013/0287748, which is herein incorporated by references in its entirety.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells can be engineered to express, for example, chimeric antigen receptors (CAR) or T cell receptor (TCR). CAR positive (+) T cells are engineered to express an extracellular single chain variable fragment (scFv) with specificity for a particular tumor antigen linked to an intracellular signaling part comprising a costimulatory domain and an activating domain. The costimulatory domain can be derived from, e.g., CD28, and the activating domain can be derived from, e.g., CD3-zeta (FIG. 1). In certain embodiments, the CAR is designed to have two, three, four, or more costimulatory domains. The CAR scFv can be designed to target, for example, CD19, which is a transmembrane protein expressed by cells in the B cell lineage, including all normal B cells and B cell malignances, including but not limited to NHL, CLL, and non-T cell ALL. Example CAR+ T cell therapies and constructs are described in U.S. Patent Publication Nos. 2013/0287748, 2014/0227237, 2014/0099309, and 2014/0050708, and these references are incorporated by reference in their entirety.

A "patient" as used herein includes any human who is afflicted with a cancer (e.g., a lymphoma or a leukemia). The terms "subject" and "patient" are used interchangeably herein.

The terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an aAPC, a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an MEW Class I molecule loaded with a peptide, an anti-CD3 antibody, a superagonist anti-CD28 antibody, and a superagonist anti-CD2 antibody.

A "costimulatory signal," as used herein, refers to a signal, which in combination with a primary signal, such as TCR/CD3 ligation, leads to a T cell response, such as, but not limited to, proliferation and/or upregulation or down regulation of key molecules.

A "costimulatory ligand" as used herein, includes a molecule on an antigen presenting cell that specifically binds a cognate co-stimulatory molecule on a T cell. Binding of the costimulatory ligand provides a signal that mediates a T cell response, including, but not limited to, proliferation, activation, differentiation, and the like. A costimulatory ligand induces a signal that is in addition to the primary signal provided by a stimulatory molecule, for instance, by binding of a T cell receptor (TCR)/CD3 complex with a major histocompatibility complex (MHC) molecule loaded with peptide. A co-stimulatory ligand can include, but is not limited to, CD7, B7-1 (CD80), B7-2 (CD86), programmed death (PD) L1, PD-L2, 4-1BB ligand, OX40 ligand, inducible costimulatory ligand (ICOS-L), intercellular adhesion molecule (ICAM), CD30 ligand, CD40, CD70, CD83, human leukocyte antigen G (HLA-G), MHC class I chain-related protein A (MICA), MHC class I chain-related protein B (MICB), herpes virus entry mediator (HVEM), lymphotoxin beta receptor, 3/TR6, immunoglobulin-like transcript (ILT) 3, ILT4, an agonist or antibody that binds Toll ligand receptor and a ligand that specifically binds with B7-H3. A co-stimulatory ligand includes, without limitation, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, tumor necrosis factor superfamily member 14 (TNFSF14 or LIGHT), natural killer cell receptor C (NKG2C), B7-H3, and a ligand that specifically binds with CD83.

A "costimulatory molecule" is a cognate binding partner on a T cell that specifically binds with a costimulatory ligand, thereby mediating a costimulatory response by the T cell, such as, but not limited to, proliferation. Costimulatory molecules include, but are not limited to, CD27, CD28, 4-1BB, OX40, CD30, CD40, CD83, PD-1, ICOS, LFA-1, CD2, CD7, TNFSF14 (LIGHT), NKG2C, B7-H3, an MHC class 1 molecule, B- and T-lymphocyte attenuator (BTLA), and a Toll ligand receptor.

The terms "conditioning" and "preconditioning" are used interchangeably herein and indicate preparing a patient in need of a T cell therapy for a suitable condition. Conditioning as used herein includes, but is not limited to, reducing the number of endogenous lymphocytes, removing a cytokine sink, increasing a serum level of one or more biomarker cytokines or pro-inflammatory factors, enhancing an effector function of T cells administered after the conditioning, enhancing antigen presenting cell activation and/or availability, or any combination thereof prior to a T cell therapy. In one embodiment, "conditioning" comprises increasing a serum level of one or more cytokines, e.g., interleukin 7 (IL-7), interleukin 15 (IL-15), interleukin 10 (IL-10), interleukin 5 (IL-5), gamma-induced protein 10 (IP-10), interleukin 8 (IL-8), monocyte chemotactic protein 1 (MCP-1), placental growth factor (PLGF), C-reactive protein (CRP), soluble intercellular adhesion molecule 1 (sICAM-1), soluble vascular adhesion molecule 1 (sVCAM-1), or any combination thereof. In another embodiment, "conditioning" comprises increasing a serum level of IL-7, IL-15, IP-10, MCP-1, PLGF, CRP, or any combination thereof.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions.

"Treatment" or "treating" of a subject refers to any type of intervention or process performed on, or the administration of an active agent to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission.

The use of the alternative (e.g., "or") should be understood to mean either one, both, or any combination thereof of the alternatives. As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% (i.e., ±10%). For example, about 3 mg can include any number between 2.7 mg and 3.3 mg (for 10%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one-tenth and one-hundredth of an integer), unless otherwise indicated.

Various aspects of the invention are described in further detail in the following subsections.

Methods of the Invention

The present invention is directed to methods of identifying patients suitable for a T cell therapy after an initial preconditioning step. The invention is thus directed to stratifying the patients into subpopulations after the first preconditioning step and treating the populations with appropriate next steps. One group of patients that are identified by the present methods can be those who are suitable for a T cell therapy after administering the first preconditioning regimen, but without any additional preconditioning regimens. Another group of patients can be those who are unsuitable for a T cell therapy with the first preconditioning step and require a second preconditioning step. A third group of patients can be those who are unsuitable for a T cell therapy even after subsequent preconditioning steps. The invention also includes preparing a patient for a T cell therapy by increasing certain biomarker cytokines in the patients using one or more preconditioning steps.

The invention identifies that an increased expression of certain cytokines in patients who have received a preconditioning regimen is indicative of an increased efficacy of a T cell therapy. The cytokines that are indicative of an increased T cell therapy efficacy comprises IL-15, IL-7, and at least one additional cytokine selected from the group consisting of monocyte chemotactic protein 1 ("MCP-1"), C-reactive protein ("CRP"), placental growth factor ("PLGF"), interferon gamma-induced protein 10 ("IP-10"), and any combination thereof. In one embodiment, the biomarker cytokines are IL-15, IL-7, and MCP-1. In another embodiment, the biomarker cytokines are IL-15, IL-7, and CRP. In other embodiments, the biomarker cytokines are IL-15, IL-7, and PLGF. In still other embodiments, the biomarker cytokines are IL-15, IL-7, MCP-1, and IP-10. In yet other embodiments, the biomarker cytokines are IL-15, IL-7, MCP-1, and CRP. In some embodiments, the biomarker cytokines are IL-15, IL-7, MCP-1, and PLGF. In certain embodiments, the biomarker cytokines are IL-15, IL-7, IP-10, and CRP. In other embodiments, the biomarker cytokines are IL-15, IL-7, PLGF, and IP-10. In yet other embodiments, the biomarker cytokines are IL-15, IL-7, MCP-1, IP-10, and CRP. In still other embodiments, the biomarker cytokines are IL-15, IL-7, MCP-1, IP-10, and PLGF. In certain embodiments, the biomarker cytokines are IL-15, IL-7, MCP-1, CRP, and PLGF. In some embodiments, the biomarker cytokines are IL-15, IL-7, IP-10, CRP, and PLGF. In other embodiments, the biomarker cytokines are IL-15, IL-7, IP-10, MCP-1, CRP, and PLGF.

In addition to the increased serum expression of the biomarker cytokines, the patients suitable for a T cell therapy can also exhibit additional characteristics: (i) a reduced number of endogenous lymphocytes; (ii) an increased effector function of T cells; (iii) an increased antigen presenting cell activation and/or availability; or (iv) any combination thereof.

The endogenous lymphocytes that are reduced by a preconditioning regimen can include, but are not limited to, endogenous regulatory T cells, B cells, natural killer cells, CD4+ T cells, CD8+ T cells, or any combination thereof, which can inhibit the anti-tumor effect of adoptively transferred T cells. Endogenous lymphocytes can compete with adoptively transferred T cells for access to antigens and supportive cytokines. Pretreatment with one or more preconditioning agents removes this competition, resulting in an increase in the level of endogenous cytokines, including IL-15 and IL-7. Once the adoptively transferred T cells are administered to the patient, they are exposed to increased levels of endogenous IL-15 and IL-7 and other homeostatic cytokines or pro-inflammatory factors. In addition, a preconditioning treatment can cause tumor cell death, leading to increased tumor antigen in the patient's serum. Not bound by any theory, conditioning with one or more preconditioning agents, including but not limited to cyclophosphamide and a purine analog, modifies the immune environment through induction of IL-15, IL-7, and one or more other biomarker cytokines, which can favor the homeostatic expansion, activation, and trafficking of T cells.

In one embodiment, the invention includes a method for identifying a patient suitable for a T cell therapy comprising administering to the patient one or more preconditioning agents that are capable of increasing a serum level of IL-15, IL-7, and at least one additional biomarker cytokine selected from the group consisting of MCP-1, CRP, PLGF, IP-10, and any combination thereof.

In another embodiment, the invention includes a method for identifying a patient suitable for a T cell therapy comprising (i) administering to the patient one or more preconditioning agents that are capable of increasing a serum level of IL-15, IL-7, and at least one additional biomarker cytokine selected from the group consisting of MCP-1, CRP, PLGF, IP-10, and any combination thereof and (ii) administering a T cell therapy when the patient exhibits an increased serum level of IL-15, IL-7, and the at least one additional biomarker cytokine.

The invention also includes a method for identifying a patient suitable for a T cell therapy comprising (i) administering to the patient one or more preconditioning agents that are capable of increasing a serum level of IL-15, IL-7, and at least one additional biomarker cytokine selected from the group consisting of MCP-1, CRP, PLGF, IP-10, and any combination thereof, (ii) measuring the serum level of IL-15, IL-7, and the at least one additional biomarker cytokine, and (iii) administering a T cell therapy when the patient exhibits an increased serum level of IL-15, IL-7, and the at least one additional biomarker cytokine.

In certain embodiments, the invention also includes a method for identifying a patient suitable for a T cell therapy comprising (i) administering to the patient one or more preconditioning agents that are capable of increasing a serum level of IL-15, IL-7, and at least one additional biomarker cytokine selected from the group consisting of MCP-1, CRP, PLGF, IP-10, and any combination thereof, (ii) administering an additional amount of the one or more preconditioning agents or directly administering an effective amount of IL-15, IL-7, and/or the at least one additional biomarker cytokine selected from the group consisting of MCP-1, CRP, PLGF, IP-10, and any combination thereof, and (iii) administering a T cell therapy when the patient exhibits an increased serum level of IL-15, IL-7, and the at least one additional biomarker cytokine.

In some embodiments, the invention also includes a method for identifying a patient suitable for a T cell therapy comprising (i) administering to the patient one or more preconditioning agents that are capable of increasing a serum level of IL-15, IL-7, and at least one additional biomarker cytokine selected from the group consisting of MCP-1, CRP, PLGF, IP-10, and any combination thereof, (ii) measuring the serum level of IL-15, IL-7, and the at least one additional biomarker cytokine, (iii) administering an additional amount of the one or more preconditioning agents or directly administering an effective amount of IL-15, IL-7, and/or the at least one additional biomarker cytokine selected from the group consisting of MCP-1, CRP, PLGF, IP-10, and any combination thereof, (iv) optionally measuring the serum level of IL-15, IL-7, and the at least one additional biomarker cytokine, and (v) administering a T cell therapy when the patient exhibits an increased serum level of IL-15, IL-7, and the at least one additional biomarker cytokine.

The invention further includes a method for increasing a serum level of IL-15, IL-7, and at least one additional biomarker cytokine selected from the group consisting of MCP-1, CRP, PLGF, IP-10, and any combination thereof to precondition a patient in need of a T cell therapy comprising administering to the patient one or more preconditioning agents, wherein the patient is treated with a T cell therapy when exhibiting an increased serum level of IL-15, IL-7, and the at least one additional biomarker cytokine.

In one embodiment, the invention includes a method for increasing a serum level of IL-15, IL-7, and at least one additional biomarker cytokine selected from the group consisting of MCP-1, CRP, PLGF, IP-10, and any combination thereof to precondition a patient in need of a T cell therapy comprising (i) administering to the patient one or more preconditioning agents and (ii) administering a T cell therapy when the patient exhibits an increased serum level of IL-15, IL-7, and the at least one additional biomarker cytokine.

In another embodiment, the invention includes a method for increasing a serum level of IL-15, IL-7, and at least one additional biomarker cytokine selected from the group consisting of MCP-1, CRP, PLGF, IP-10, and any combination thereof to precondition a patient in need of a T cell therapy comprising (i) administering to the patient one or more preconditioning agents, (ii) administering an additional amount of the one or more preconditioning agents or administering an effective amount of IL-15, IL-7, and the at least one additional biomarker cytokine selected from the group consisting of MCP-1, CRP, PLGF, IP-10, and any combination thereof, and (iii) administering a T cell therapy when the patient exhibits an increased serum level of IL-15, IL-7, and the at least one additional biomarker cytokine.

In certain embodiments, the method further comprises measuring the serum level of IL-15, IL-7, and the at least one additional biomarker cytokine after the administration of the one or more preconditioning agents. In one embodiment, the serum level of IL-15 is measured. In another embodiment, the serum level of IL-7 is measured. In another embodiment, the serum levels of IL-15 and IL-7 are measured.

The present invention also provides methods of treating a patient who exhibits an increased serum level of IL-15, IL-7, and at least one additional biomarker cytokine after administration of one or more preconditioning agents comprising administering a T cell therapy to the patient. The methods of the invention also includes further preconditioning a patient who does not exhibit a sufficient serum level of IL-15, IL-7, and at least one additional biomarker cytokine after administration of a first dose of one or more preconditioning agents, comprising administering a second dose of one or more preconditioning agents. In certain patients who do not exhibit any increased serum level of IL-15, IL-7, and the at least additional biomarker cytokine after the administration of the one or more preconditioning agents, the invention includes further administering an effective amount of the biomarker cytokines directly to the patient.

In other embodiments, the invention includes identifying one or more cytokines which are increased in the serum of a patient following administration of one or more preconditioning agents, wherein the increased serum levels of the one or more cytokines correlate with an increased responsiveness to a subsequent T cell therapy. In one embodiment, the serum levels of the one or more cytokines can be measured following the administration of the preconditioning agents. Patients who do not exhibit increased serum levels of the one or more cytokines can be subjected to an additional treatment. In one embodiment, the additional treatment includes administering to the patient a second dose of the one or more preconditioning agents capable of increasing the serum level of certain cytokines, e.g., IL-15, IL-7, and at least one additional biomarker cytokine. In another embodiment, the additional treatment includes administering to the patient one or more other treatment that increases the serum level of the one or more cytokines including administering to the patient one or more additional cytokines, one or more preconditioning agents not previously administered to the patient, or T cells engineered to express the one or more cytokines e.g., IL-15, IL-7, and at least one additional biomarker cytokine.

In another embodiment, the present invention provides methods for identifying cytokines which increase the effectiveness of a T cell therapy when upregulated in patients prior to administration of the T cell therapy, wherein the identified cytokines is administered to a patient prior to the T cell therapy with or without administering to the patient other preconditioning agents, or wherein the dose of the one or more preconditioning agents is increased to further increase the serum level of the identified cytokines. In another embodiment, the present invention provides a method of continuously monitoring serum levels of certain biomarker cytokines during conditioning and adjusting the timing and dosing accordingly, e.g., continuing preconditioning until the desired serum levels of the biomarker cytokines are achieved and the patient is ready for a T cell therapy.

In other embodiments, the invention includes a method of increasing the serum levels of one or more biomarker cytokine in a patient in need of a T cell therapy. In some embodiments, the serum levels of the one or more biomarker cytokine are increased by administering to the patient one or more preconditioning agents. In some embodiments, the serum levels of the one or more biomarker cytokine are increased by administering to the patient one or more cytokine selected from IL-15, IL-7, and at least one additional cytokine selected from the group consisting of MCP-1, CRP, PLGF, IP-10, and any combination thereof. In some embodiments, the serum levels of the one or more biomarker cytokine are increased by administering to the patient T cells engineered to express one or more cytokine selected from IL-15, IL-7, and at least one additional cytokine selected from the group consisting of MCP-1, CRP, PLGF, IP-10, and any combination thereof.

In one embodiment, the invention includes methods of treating a cancer in a patient suitable for a T cell therapy, comprising preconditioning the patient by administering to the patient one or more preconditioning agents that are capable of increasing the serum level of IL-15, IL-7, and at least one additional biomarker cytokine, wherein the patient is treated with a T cell therapy when exhibiting an increased serum level of IL-15, IL-7, and the at least one additional biomarker cytokine. The present invention shows that preconditioning a patient with one or more preconditioning agents that are capable of increasing the serum level of IL-15, IL-7 and at least one additional biomarker cytokine selected from the group consisting of MCP-1, CRP, PLGF, IP-10, and any combination thereof enhances the effectiveness of a T cell therapy subsequently administered to the patient. In another embodiment, the invention includes a method for treating a cancer in a patient suitable for a T cell therapy comprising administering to the patient one or more preconditioning agents that are capable of increasing a serum level of IL-15, IL-7, and at least one additional cytokine selected from the group consisting of MCP-1, CRP, PLGF, IP-10, and any combination thereof, wherein the patient is treated with a T cell therapy when exhibiting an increased serum level of IL-15, IL-7, and the at least one additional biomarker cytokine.

In other embodiments, the invention includes a method for treating a cancer in a patient suitable for a T cell therapy comprising (i) administering to the patient one or more preconditioning agents that are capable of increasing a serum level of IL-15, IL-7, and at least one additional biomarker cytokine selected from the group consisting of MCP-1, CRP, PLGF, IP-10, and any combination thereof and (ii) administering a T cell therapy when the patient exhibits an increased serum level of IL-15, IL-7, and the at least one additional biomarker cytokine.

In another embodiment, the invention includes a method for treating a cancer in a patient suitable for a T cell therapy comprising (i) administering to the patient one or more preconditioning agents that are capable of increasing a serum level of IL-15, IL-7, and at least one additional biomarker cytokine selected from the group consisting of MCP-1, CRP, PLGF, IP-10, and any combination thereof, (ii) administering an additional amount of the one or more preconditioning agents or administering an effective amount of IL-15, IL-7, and the at least one additional biomarker cytokine selected from the group consisting of MCP-1, CRP, PLGF, IP-10, and any combination thereof, and (iii) administering a T cell therapy when the patient exhibits an increased serum level of IL-15, IL-7, and the at least one additional biomarker cytokine.

In another embodiment, the invention includes a method of identifying a dose of one or more preconditioning agents that is effective for preparing a subject for a T cell therapy comprising (i) administering to the patient one or more preconditioning agents (e.g., cyclophosphamide and/or fludarabine), (ii) measuring the serum levels of IL-7, IL-15, IL-10, IL-5, IP-10, IL-8, MCP-1, PLGF, CRP, sICAM-1, sVCAM-1, perforin, MIP-1b, or any combination thereof, and (iii) characterizing the one or more preconditioning agents (e.g., cyclophosphamide and/or fludarabine) as being effective for preparing a subject for a T cell therapy, where following the administration of the one or more preconditioning agents, the subject exhibits an increased serum level of IL-7, IL-15, IL-10, IL-5, IP-10, IL-8, MCP-1, PLGF, CRP, sICAM-1, sVCAM-1, or any combination thereof, e.g., IL-15, IP-10, and/or IL-7, and/or a decreased serum level of perforin and/or MIP-1b. In some embodiments, the method further comprises administering the one or more preconditioning agents to the patent who exhibited an increased serum level of IL-7, IL-15, IL-10, IL-5, IP-10, IL-8, MCP-1, PLGF, CRP, sICAM-1, sVCAM-1, or any combination thereof, e.g., IL-15, IP-10, and/or IL-7, and/or a decreased serum level of perform and/or MIP-1b. In other embodiments, the method further comprises administering a T cell therapy to the patient who exhibited an increased serum level of IL-7, IL-15, IL-10, IL-5, IP-10, IL-8, MCP-1, PLGF, CRP, sICAM-1, sVCAM-1, or any combination thereof, e.g., IL-15, IP-10, and/or IL-7, and/or a decreased serum level of perforin and/or MIP-1b.

In another embodiment, the invention includes a method of verifying the effectiveness of one or more preconditioning agents for preparing a subject for a T cell therapy comprising (i) administering to the patient one or more preconditioning agents (e.g., cyclophosphamide and/or fludarabine), (ii) measuring the serum levels of IL-7, IL-15, IL-10, IL-5, IP-10, IL-8, MCP-1, PLGF, CRP, sICAM-1, sVCAM-1, perforin, MIP-1b, or any combination thereof, and (iii) characterizing the one or more preconditioning agents (e.g., cyclophosphamide and/or fludarabine) as being effective for preparing a subject for a T cell therapy where following the administration of the one or more preconditioning agents, the subject exhibits an increased serum level of IL-7, IL-15, IL-10, IL-5, IP-10, IL-8, MCP-1, PLGF, CRP, sICAM-1, sVCAM-1, or any combination thereof, e.g., IL-15, IP-10, and/or IL-7, and/or a decreased serum level of perforin and/or MIP-1b. In some embodiments, the method further comprises administering the one or more preconditioning agents to the patent who exhibited an increased serum level of IL-7, IL-15, IL-10, IL-5, IP-10, IL-8, MCP-1, PLGF, CRP, sICAM-1, sVCAM-1, or any combination thereof, e.g., IL-15, IP-10, and/or IL-7, and/or a decreased serum level of perform and/or MIP-1b. In other embodiments, the method further comprises administering a T cell therapy to the patient who exhibited an increased serum level of IL-7, IL-15, IL-10, IL-5, IP-10, IL-8, MCP-1, PLGF, CRP, sICAM-1, sVCAM-1, or any combination thereof, e.g., IL-15, IP-10, and/or IL-7, and/or a decreased serum level of perforin and/or MIP-1b.

In some embodiments, administration of the one or more preconditioning agents reduces the number of endogenous lymphocytes in the patient. In certain embodiments, the endogenous lymphocytes comprise regulatory T cells, B cells, natural killer cells, CD4+ T cells, CD8+ T cells, or any combination thereof. In some embodiments, administration of the one or more preconditioning agents increases the availability of a homeostatic cytokine, e.g., IL-15 and/or IL-7. In some embodiments, administration of the one or more preconditioning agents enhances an effector function of T cells administered after the conditioning. In some embodiments, administration of the one or more preconditioning agents enhances antigen presenting cell activation and/or availability.

In certain embodiments, the administration of the one or more preconditioning agents induces an improved antitumor efficacy of the T cell therapy compared to the antitumor efficacy of the T cell therapy without the administration of the one or more preconditioning agents.

Cytokine Levels

The invention describes use of biomarker cytokines for effective treatment of a cancer in a T cell therapy. In particular, this application identifies a group of cytokines that are key factors in providing an adequate environment for transferred T cells, improving the efficacy of the T cell therapy. In one embodiment, the invention is about inducing an up-regulation or increasing a serum level of the biomarker cytokines. Administration of one or more preconditioning agents prior to administration of a T cell therapy increases the level of the biomarker cytokines, modifying the immune environment in a way that favors the homeostatic expansion, activation, and trafficking of T cells. Once the adoptively transferred T cells are administered to the patient, they are exposed to increased levels of endogenous cytokines. The biomarker cytokines that are indicative of T cell efficacy include, but are not limited to, IL-15, IL-7, and at least one additional biomarker cytokine selected from the group consisting of MCP-1, CRP, PLGF, IP-10, and any combination thereof.

The invention also includes a method of increasing the availability of a biomarker cytokine in a patient in need of a T cell therapy. In certain embodiments, the biomarker cytokine is IL-15, IL-7, and at least one additional biomarker cytokine selected from the group consisting of MCP-1, CRP, PLGF, IP-10, and any combination thereof.

In certain embodiments, the invention provides a method of determining a treatment option for a patient comprising (i) measuring a serum level of a biomarker cytokine (e.g., IL-15 or IL-7) after administration of a first dose of one or more preconditioning agents and (ii) administering a T cell therapy to a patient who exhibits an increased level of one or more biomarker cytokines (e.g., a patient who is more likely to respond to a T cell therapy). In other embodiments, the invention provides a method of determining a treatment option for a patient comprising (i) measuring a serum level of a biomarker cytokine (e.g., IL-15 or IL-7) after administration of a first dose of one or more preconditioning agents and (ii) administering a second dose of the one or more preconditioning agents to a patient who does not exhibit an increased level of one or more biomarker cytokines or who exhibits less than a threshold level of the one or more biomarker cytokines (e.g., a patient who is not likely to respond to a T cell therapy). In some embodiments, the invention provides a method of determining a treatment option for a patient comprising (i) measuring a serum level of a biomarker cytokine (e.g., IL-15 or IL-7) after administration of one or more preconditioning agents, (ii) administering one or more biomarker cytokines to the patient who does not exhibit an increased level of one or more biomarker cytokines or who exhibits less than a threshold level of the one or more biomarker cytokines, (iii) administering a T cell therapy to the patient who exhibits an increased level of one or more biomarker cytokines or who exhibits more than a threshold level of the one or more cytokines.

In one embodiment, a more than about 5 fold, more than about 10 fold, more than about 15 fold, more than about 20 fold, more than about 25 fold, more than about 30 fold, more than about 35 fold, more than about 40 fold, more than about 45 fold, more than about 50 fold, more than about 60 fold, more than about 70 fold, more than about 80 fold, or more than about 90 fold increase in the serum IL-15 level following administration of one or more preconditioning agents indicates that a patient is more likely to respond to a T cell therapy. In a particular embodiment, a more than about 10 fold increase in the serum IL-15 level following administration of one or more preconditioning agents indicates that a patient is more likely to respond to a T cell therapy. In another embodiment, a more than about 20 fold increase in the serum IL-15 level following administration of one or more preconditioning agents indicates that a patient is more likely to respond to a T cell therapy. In another embodiment, a more than about 30 fold increase in the serum IL-15 level following administration of one or more preconditioning agents indicates that a patient is more likely to respond to a T cell therapy. In order to increase the serum level of IL-15, exogenous IL-15 and/or an additional amount of the one or more preconditioning agents can be administered to the patient.

In another embodiment, a more than about 2 fold, more than about 3 fold, more than about 4 fold, more than about 5 fold, more than about 10 fold, more than about 15 fold, more than about 20 fold, more than about 25 fold, more than about 30 fold, more than about 35 fold, more than about 40 fold, more than about 45 fold, more than about 50 fold, more than about 60 fold, more than about 70 fold, more than about 80 fold, or more than about 90 fold increase in the serum IL-7 level following administration of one or more preconditioning agents indicates that a patient is more likely to respond to a T cell therapy. In a particular embodiment, a more than about 2 fold increase in the serum IL-7 level following administration of one or more preconditioning agents indicates that a patient is more likely to respond to a T cell therapy. In order to increase the serum level of IL-7, an exogenous IL-7 and/or an additional dose of one or more preconditioning agents can be administered to the patient.

In other embodiments, a more than about 2 fold, more than about 3 fold, more than about 4 fold, more than about 5 fold, more than about 6 fold, more than about 7 fold, more than about 8 fold, more than about 9 fold, more than about 10 fold, more than about 15 fold, more than about 20 fold, or more than about 30 fold increase in the serum IP-10 level following administration of one or more preconditioning agents indicates that a patient is more likely to respond to a T cell therapy. In a particular embodiment, a more than about 2 fold increase in the serum IP-10 level following administration of one or more preconditioning agents indicates that a patient is more likely to respond to a T cell therapy. In another embodiment, a more than about 3 fold increase in the serum IP-10 level following administration of one or more preconditioning agents indicates that a patient is more likely to respond to a T cell therapy. In another embodiment, a more than about 4 fold increase in the serum IP-10 level following administration of one or more preconditioning agents indicates that a patient is more likely to respond to a T cell therapy. In another embodiment, a more than about 7 fold increase in the serum IP-10 level following administration of one or more preconditioning agents indicates that a patient is more likely to respond to a T cell therapy. In order to increase the serum level of IP-10, exogenous IP-10 and/or an additional amount of the one or more preconditioning agents can be administered to the patient.

In some embodiments, a more than about 1.5 fold, more than about 2 fold, more than about 3 fold, more than about 4 fold, more than about 5 fold, more than about 6 fold, more than about 7 fold, more than about 8 fold, more than about 9 fold, more than about 10 fold, more than about 15 fold, or more than about 20 fold increase in the serum MCP-1 level following administration of one or more preconditioning agents indicates that a patient is more likely to respond to a T cell therapy. In other embodiments, a more than about 2 fold increase in the serum MCP-1 level following administration of one or more preconditioning agents indicates that a patient is more likely to respond to a T cell therapy. In another embodiment, a more than about 3 fold increase in the serum MCP-1 level following administration of one or more preconditioning agents indicates that a patient is more likely to respond to a T cell therapy. In another embodiment, a more than about 5 fold increase in the serum MCP-1 level following administration of one or more preconditioning agents indicates that a patient is more likely to respond to a T cell therapy. In another embodiment, a more than about 7 fold increase in the serum MCP-1 level following administration of one or more preconditioning agents indicates that a patient is more likely to respond to a T cell therapy. In order to increase the serum level of MCP-1, exogenous MCP-1 and/or an additional amount of the one or more preconditioning agents can be administered to the patient.

In certain embodiments, a more than about 1.5 fold, more than about 2 fold, more than about 3 fold, more than about 4 fold, more than about 5 fold, more than about 10 fold, more than about 15 fold, more than about 20 fold, more than about 25 fold, more than about 30 fold, more than about 35 fold, more than about 40 fold, more than about 45 fold, more than about 50 fold, more than about 60 fold, more than about 70 fold, more than about 80 fold, more than about 90 fold, or more than about 100 fold increase in the serum PLGF level following administration of one or more preconditioning agents indicates that a patient is more likely to respond to a T cell therapy. In a particular embodiment, a more than about 1.5 fold increase in the serum PLGF level following administration of one or more preconditioning agents indicates that a patient is more likely to respond to a T cell therapy. In another embodiment, a more than about 2 fold increase in the serum PLGF level following administration of one or more preconditioning agents indicates that a patient is more likely to respond to a T cell therapy. In another embodiment, a more than about 3 fold increase in the serum PLGF level following administration of one or more preconditioning agents indicates that a patient is more likely to respond to a T cell therapy. In order to increase the serum level of PLGF, exogenous PLGF and/or an additional amount of the one or more preconditioning agents can be administered to the patient.

In other embodiments, a more than about 1.5 fold, more than about 2 fold, more than about 3 fold, more than about 4 fold, more than about 5 fold, more than about 9 fold, more than about 10 fold, more than about 15 fold, more than about 20 fold, more than about 25 fold, more than about 30 fold, more than about 35 fold, more than about 40 fold, more than about 45 fold, more than about 50 fold, more than about 60 fold, more than about 70 fold, more than about 80 fold, more than about 90 fold, or more than about 100 fold increase in the serum CRP level following administration of one or more preconditioning agents indicates that a patient is more likely to respond to a T cell therapy. In a particular embodiment, a more than about 1.5 fold increase in the serum CRP level following administration of one or more preconditioning agents indicates that a patient is more likely to respond to a T cell therapy. In another embodiment, a more than about 2 fold increase in the serum CRP level following administration of one or more preconditioning agents indicates that a patient is more likely to respond to a T cell therapy. In another embodiment, a more than about 5 fold increase in the serum CRP level following administration of one or more preconditioning agents indicates that a patient is more likely to respond to a T cell therapy. In another embodiment, a more than about 9 fold increase in the serum CRP level following administration of one or more preconditioning agents indicates that a patient is more likely to respond to a T cell therapy. In another embodiment, a more than about 10 fold increase in the serum CRP level following administration of one or more preconditioning agents indicates that a patient is more likely to respond to a T cell therapy. In another embodiment, the level of CRP in a patient suitable for a T cell therapy is increased by at least a more than about 25 fold increase in the serum CRP level following administration of one or more preconditioning agents indicates that a patient is more likely to respond to a T cell therapy. In order to increase the serum level of CRP, exogenous CRP and/or an additional dose of the one or more preconditioning agent can be administered to the patient.

In some embodiments, the one or more preconditioning agents further increase a serum level of interleukin 10 ("IL-10"), interleukin 5 ("IL-5"), interleukin 8 ("IL-8"), soluble intercellular adhesion molecule 1 ("sICAM-1"), soluble vascular adhesion molecule 1 ("sVCAM-1"), or any combinations thereof.

In some embodiments, the serum level of any one or more cytokine is measured on or one or more days before administration of the one or more preconditioning agents and on one or more days selected from the day of administration of the T cell therapy to 21 days after administration of the T cell therapy.

One of skill in the art would recognize that the level of biomarker cytokines can be increased by a number of different methods, including but not limited to, the use of the one or more preconditioning agents as described herein, administration of one or more exogenous cytokines to the patient as described herein, administration of one or more compositions that induce the expression of or prevent the degradation of one or more endogenous cytokines, administration of one or more transgenic cells capable of expressing one or more recombinant cytokines, and any other method having the effect of increasing the level of biomarker cytokines in a patient.

In some embodiments, the invention includes a method of preconditioning a patient in need of a T cell therapy, comprising administering to the patient one or more preconditioning agents and an effective amount IL-15, IL-7, and at least one additional cytokine selected from the group consisting of MCP-1, CRP, PLGF, IP-10, and any combination thereof. The cytokine to be administered to the patient can be obtained by any methods known in the art. For example the cytokine can be an isolated cytokine or a recombinant cytokine. The one or more doses of an isolated or recombinant cytokine can be administered before the T cell therapy, or after the T Cell therapy, or any combination thereof.

In one embodiment, the method of conditioning a patient in need of a T cell therapy, comprises administering to the patient one or more preconditioning agents and one or more doses of IL-2. In some embodiments, the dose of IL-2 is at least about 10,000 IU/kg, at least about 50,000 IU/kg, at least about 100,000 IU/kg, at least about 200,000 IU/kg, at least about 400,000 IU/kg, at least about 600,000 IU/kg, at least about 700,000 IU/kg, at least about 800,000 IU/kg, or at least about 1,000,000 IU/kg. In one embodiment, the dose of IL-2 is at least about 700,000 IU/kg. In one particular embodiment, the dose of IL-2 is about 720,000 IU/kg. In some embodiments, IL-2 will be administered to the patient every 8 hours until 15 doses or toxicity precludes additional doses.

Various cytokines can be enriched in patient serum following administration of the one or more preconditioning agents and/or a T cell therapy. In some embodiments, the patient after the administration of one or more preconditioning agents and/or a T cell therapy exhibits an increased serum concentration of a cytokine or a pro-inflammatory factor selected from the group consisting of interleukin (IL) 15, IL-7, IL-10, IL-5, IL-8, IL-1, IL-1b, IL-2, IL-3, IL-4, IL-6, IL-9, IL-11, IL-12, IL-12p40, IL-12p70, IL-13, IL-14, IL-16, IL-17, IL-17a, IL-20, IL-21, granulocyte macrophage colony-stimulating factor (GM-CSF), granulocyte colony-stimulating factor (G-CSF), monocyte chemotactic protein 1 (MCP-1), MCP-4, gamma-induced protein 10 (IP-10), placental growth factor (PLGF), soluble intercellular adhesion molecule 1 (sICAM-1), soluble vascular adhesion molecule 1 (sVCAM-1), C-reactive protein (CRP), vascular endothelial growth factor (VEGF), VEGF-C, VEGF-D, macrophage inflammatory protein 1β (MIP-1β, MIP-1b), leukemia inhibitory factor (LIF), oncostatin M (OSM), interferon (IFN) alpha, IFN-beta, IFN-gamma, tumor necrosis factor (TNF) alpha, TNF-beta, CD154, lymphotoxin (LT) beta, 4-1BB ligand (4-1BBL), a proliferation-inducing ligand (APRIL), CD70, CD153, CD178, glucocorticoid-induced TNFR-related ligand (GITRL), tumor necrosis factor superfamily member 14 (TNFSF14), OX40L, TNF- and ApoL-related leukocyte-expressed ligand 1 (TALL-1), TNF-related apoptosis-inducing ligand (TRAIL), chemokine (C-C motif) ligand (CCL) 1, macrophage inflammatory protein 1 alpha (MIP-1a or CCL3), CCL5, monocyte-specific chemokine 3 (MCP3 or CCL7), monocyte chemoattractant protein 2 (MCP-2 or CCL8), CCL13, thymus and activation regulated chemokine (TARC or CCL17), CCL22, FGF2, eotaxin, MDC, granzine A, granzine B, perforin, SAA, MCP-4, and any combination thereof. In some embodiments, following the administration of cyclophosphamide and fludarabine the patient exhibits increased serum levels of IL-15 and/or IP-10. In some embodiments, following the administration of cyclophosphamide and fludarabine the patient exhibits a decreased serum level of perforin.

Preconditioning Agents

The one or more preconditioning agents of the present invention can be any preconditioning agents capable of increasing the level of a serum level of IL-15, IL-7, and at least one additional cytokine selected from the group consisting of MCP-1, CRP, PLGF, IP-10, and/or any combination thereof. For example, the one or more preconditioning agents can comprise an alkylating agent. In certain embodiments, the alkylating agent can be selected from the group consisting of melphalan, chlorambucil, cyclophosphamide, mechlorethamine, mustine (HN2), uramustine, uracil mustard, melphalan, chlorambucil, ifosfamide, bendamustine, carmustine, lomustine, streptozocin, alkyl sulfonates, busulfan, thiotepa or its analogues, any analogue or functional derivative thereof, and any combination thereof. In one particular embodiment, the one or more preconditioning agents comprise cyclophosphamide.

Cyclophosphamide (ENDOXAN®, CYTOXAN®, PROCYTOX®, NEOSAR®, REVIMMUNE®, CYCLOBLASTIN®) is a nitrogen mustard-derivative alkylating agent with potent immunosuppressive activity. Cyclophosphamide acts as an antineoplastic, and it is used to treat various types of cancers including lymphoma, multiple myeloma, leukemia, mycosis fungoides, neuroblastoma, ovarian cancer, eye cancer, and breast cancer, as well as autoimmune disorders.

Once administered to a patient, cyclophosphamide is converted into acrolein and phosphoramide in the liver. Together, these metabolites crosslink DNA in both resting and dividing cells by adding an alkyl group to guanine bases of DNA at the number seven nitrogen atom of the imidazole ring. As a result, DNA replication is inhibited leading to cell death.

In another embodiment, the one or more preconditioning agents can include platinum-based chemotherapeutic agents. In certain embodiments, the platinum-based chemotherapeutic agents are selected from the group consisting of platinum, cisplatin, carboplatin, nedaplatin, oxaliplatin, satraplatin, triplatin tetranitrate, procarbazine, altretamine, triazenes, dacarbazine, mitozolomide, temozolomide, dacarbazine, temozolomide, any analogues or functional derivatives thereof, and any combination thereof.

In another embodiment, the one or more preconditioning agents can include purine analogues. In certain embodiments, the purine analogues are selected from the group consisting of azathioprine, 6-mercaptopurine, mercaptopurine, thiopurines, thioguanine, fludarabine, pentostatin, cladribine, any analogue or functional derivative thereof, and any combination thereof. In one embodiment, the one or more preconditioning agents includes fludarabine.

Fludarabine phosphate (FLUDARA®) is a synthetic purine nucleoside that differs from physiologic nucleosides in that the sugar moiety is arabinose instead of ribose or deoxyribose. Fludarabine acts as a purine antagonist antimetabolite, and it is used to treat various types of hematological malignancies, including various lymphomas and leukemias.

Once administered to a patient, fludarabine is rapidly dephosphorylated to 2-fluoro-ara-A and then phosphorylated intracellularly by deoxycytidine kinase to the active triphosphate, 2-fluoro-ara-ATP. This metabolite then interferes with DNA replication, likely by inhibiting DNA polymerase alpha, ribonucleotide reductase, and DNA primase, thus inhibiting DNA synthesis. As a result, fludarabine administration leads to increased cell death in dividing cells.

In some embodiments, the one or more preconditioning agents can include cyclophosphamide and a purine analog. The purine analogues can be selected from the group consisting of azathioprine, 6-mercaptopurine, mercaptopurine, thiopurines, thioguanine, fludarabine, pentostatin, cladribine, any analogue or functional derivative thereof, and any combination thereof. In one particular embodiment, the one or more preconditioning agents include cyclophosphamide and pentostatin. In one particular embodiment, the one or more preconditioning agents include cyclophosphamide and fludarabine.

In certain embodiments, a first dose of the one or more preconditioning agents is administered to the patient. For example, in some embodiments, a first dose of cyclophosphamide is about 300 mg/m$^2$/day to about 2000 mg/m$^2$/day. In another embodiment, the first dose of cyclophosphamide is higher than 300 mg/m$^2$/day and lower than 2000 mg/m$^2$/day. In other embodiments, the dose of cyclophosphamide is about 350 mg/m$^2$/day-about 2000 mg/m$^2$/day, at least about 400 mg/m$^2$/day-about 2000 mg/m$^2$/day, about 450 mg/m$^2$/day-about 2000 mg/m$^2$/day, about 500 mg/m$^2$/day-about 2000 mg/m$^2$/day, about 550 mg/m$^2$/day-about 2000 mg/m$^2$/day, or about 600 mg/m$^2$/day-about 2000 mg/m$^2$/day. In other embodiments, the dose of cyclophosphamide is about 350 mg/m$^2$/day-about 1500 mg/m$^2$/day, about 350 mg/m$^2$/day-about 1000 mg/m$^2$/day, about 400 mg/m$^2$/day-about 900 mg/m$^2$/day, about 450 mg/m$^2$/day-about 800 mg/m$^2$/day, about 450 mg/m$^2$/day-about 700 mg/m$^2$/day, about 500 mg/m$^2$/day-about 600 mg/m$^2$/day, or about 300 mg/m$^2$/day-about 500 mg/m$^2$/day. In another embodiment, the dose of cyclophosphamide is about 350 mg/m$^2$/day, about 400 mg/m$^2$/day, about 450 mg/m$^2$/day, about 500 mg/m$^2$/day, about 550 mg/m$^2$/day, about 600 mg/m$^2$/day, about 650 mg/m$^2$/day, about 700 mg/m$^2$/day, about 800 mg/m$^2$/day, about 900 mg/m$^2$/day, or about 1000 mg/m$^2$/day.

In other embodiments, the first dose of cyclophosphamide is about 200 mg/m$^2$/day to about 3000 mg/m$^2$/day. In another embodiment, the first dose of cyclophosphamide is higher than 200 mg/m$^2$/day and lower than 3000 mg/m$^2$/day. In other embodiments, the dose of cyclophosphamide is about 200 mg/m$^2$/day-about 3000 mg/m$^2$/day, about 300 mg/m$^2$/day-about 3000 mg/m$^2$/day, about 400 mg/m$^2$/day-about 3000 mg/m$^2$/day, about 500 mg/m$^2$/day-about 3000 mg/m$^2$/day, about 600 mg/m$^2$/day-about 3000 mg/m$^2$/day, about 700 mg/m$^2$/day-about 3000 mg/m$^2$/day, about 800 mg/m$^2$/day-about 3000 mg/m$^2$/day, about 900 mg/m$^2$/day-about 3000 mg/m$^2$/day, about 1000 mg/m$^2$/day-about 3000 mg/m$^2$/day, about 1100 mg/m$^2$/day-about 3000 mg/m$^2$/day, about 1200 mg/m$^2$/day-about 3000 mg/m$^2$/day, about 1300 mg/m$^2$/day-about 3000 mg/m$^2$/day, about 1400 mg/m$^2$/day-about 3000 mg/m$^2$/day, about 1500 mg/m$^2$/day-about 3000 mg/m$^2$/day, about 1600 mg/m$^2$/day-about 3000 mg/m$^2$/day, about 1700 mg/m$^2$/day-about 3000 mg/m$^2$/day, about 1800 mg/m$^2$/day-about 3000 mg/m$^2$/day, about 1900 mg/m$^2$/day-about 3000 mg/m$^2$/day, about 2000 mg/m$^2$/day-about 3000 mg/m$^2$/day, about 200 mg/m$^2$/day-about 2900 mg/m$^2$/day, about 400 mg/m$^2$/day-about 2800 mg/m$^2$/day, about 500 mg/m$^2$/day-about 2700 mg/m$^2$/day, about 600 mg/m$^2$/day-about 2600 mg/m$^2$/day, about 700 mg/m$^2$/day-about 2500 mg/m$^2$/day, about 800 mg/m$^2$/day-about 2400 mg/m$^2$/day, about 900 mg/m$^2$/day-about 2350 mg/m$^2$/day, about 1000 mg/m$^2$/day-about 2300 mg/m$^2$/day, about 1100 mg/m$^2$/day-about 2250 mg/m$^2$/day, or about 1110 mg/m$^2$/day-about 2220 mg/m$^2$/day. In one embodiment, the first dose of cyclophosphamide is 200 mg/m$^2$/day. In another embodiment, the first dose of cyclophosphamide is 300 mg/m$^2$/day. In another embodiment, the first dose of cyclophosphamide is 500 mg/m$^2$/day.

In some embodiments, a first dose of fludarabine is about 20 mg/m$^2$/day to about 900 mg/m$^2$/day. In some embodiments, a dose of fludarabine is higher than 30 mg/m$^2$/day and lower than 900 mg/m$^2$/day. In some embodiments, a dose fludarabine is about 35 mg/m$^2$/day-about 900 mg/m$^2$/day, about 40 mg/m$^2$/day-about 900 mg/m$^2$/day, about 45 mg/m$^2$/day-about 900 mg/m$^2$/day, about 50 mg/m$^2$/day-about 900 mg/m$^2$/day, about 55 mg/m$^2$/day-about 900 mg/m$^2$/day, or about 60 mg/m$^2$/day-about 900 mg/m$^2$/day. In some embodiments, a dose of fludarabine is about 35 mg/m$^2$/day-about 900 mg/m$^2$/day, about 35 mg/m$^2$/day-about 800 mg/m$^2$/day, about 35 mg/m$^2$/day-about 700 mg/m$^2$/day, about 35 mg/m$^2$/day-about 600 mg/m$^2$/day, about 35 mg/m$^2$/day-about 500 mg/m$^2$/day, about 35 mg/m$^2$/day-about 400 mg/m$^2$/day, about 35 mg/m$^2$/day-about 300 mg/m$^2$/day, about 35 mg/m$^2$/day-about 200 mg/m$^2$/day, about 35 mg/m$^2$/day-about 100 mg/m$^2$/day, about 40 mg/m$^2$/day-about 90 mg/m$^2$/day, about 45 mg/m$^2$/day-about 80 mg/m$^2$/day, about 45 mg/m$^2$/day-about 70 mg/m$^2$/day, or about 50 mg/m$^2$/day-about 60 mg/m$^2$/day. In some embodiments, a dose of fludarabine is about 20 mg/m$^2$/day, about 25 mg/m$^2$/day, about 30 mg/m$^2$/day, about 35 mg/m$^2$/day, about 40 mg/m$^2$/day, about 45 mg/m$^2$/day, about 50 mg/m$^2$/day, about 55 mg/m$^2$/day, about 60 mg/m$^2$/day, about 65 mg/m$^2$/day, about 70 mg/m$^2$/day, about 75 mg/m$^2$/day, about 80 mg/m$^2$/day, about 85 mg/m$^2$/day, about 90 mg/m$^2$/day, about 95 mg/m$^2$/day, about 100 mg/m$^2$/day, about 200 mg/m$^2$/day, or about 300 mg/m$^2$/day. In some embodiments, a dose of fludarabine is about 20 mg/m$^2$/day, about 25 mg/m$^2$/day, about 30 mg/m$^2$/day, about 35 mg/m$^2$/day, about 40 mg/m$^2$/day, about 45 mg/m$^2$/day, about 50 mg/m$^2$/day, about 55 mg/m$^2$/day, about 60 mg/m$^2$/day, about 65 mg/m$^2$/day, about 70 mg/m$^2$/day, about 75 mg/m$^2$/day, about 80 mg/m$^2$/day, about 85 mg/m$^2$/day, about 90 mg/m$^2$/day, about 95 mg/m$^2$/day, or about 100 mg/m$^2$/day. In other embodiments, the dose of fludarabine is about 110 mg/m$^2$/day, 120 mg/m$^2$/day, 130 mg/m$^2$/day, 140 mg/m$^2$/day, 150 mg/m$^2$/day, 160 mg/m$^2$/day, 170 mg/m$^2$/day, 180 mg/m$^2$/day, or 190 mg/m$^2$/day. In some embodiments, the dose of fludarabine is about 210 mg/m$^2$/day, 220 mg/m$^2$/day, 230 mg/m$^2$/day, 240 mg/m$^2$/day, 250 mg/m$^2$/day, 260 mg/m$^2$/day, 270 mg/m$^2$/day, 280 mg/m$^2$/day, or 290 mg/m$^2$/day. In one particular embodiment, the dose of fludarabine is about 20 mg/m$^2$/day. In one particular embodiment, the dose of fludarabine is about 25 mg/m$^2$/day. In another embodiment, dose of fludarabine is about 30 mg/m$^2$/day. In another embodiment, dose of fludarabine is about 60 mg/m$^2$/day.

In some embodiments, the dose of cyclophosphamide is 100 mg/m$^2$/day (or 110 mg/m$^2$/day, 120 mg/m$^2$/day, 130 mg/m²/day, or 140 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is 150 mg/m²/day (or 160 mg/m²/day, 170 mg/m²/day, 180 mg/m²/day, or 190 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is about 200 mg/m²/day (or 210 mg/m²/day, 220 mg/m²/day, 230 mg/m²/day, or 240 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is 250 mg/m²/day (or 260 mg/m²/day, 270 mg/m²/day, 280 mg/m²/day, or 290 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is 300 mg/m²/day (or 310 mg/m²/day, 320 mg/m²/day, 330 mg/m²/day, or 340 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is 350 mg/m²/day (or 360 mg/m²/day, 370 mg/m²/day, 380 mg/m²/day, or 390 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is 400 mg/m²/day (or 410 mg/m²/day, 420 mg/m²/day, 430 mg/m²/day, or 440 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is 450 mg/m²/day (or 460 mg/m²/day, 470 mg/m²/day, 480 mg/m²/day, or 490 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is 500 mg/m²/day (or 510 mg/m²/day, 520 mg/m²/day, 530 mg/m²/day, or 540 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is 550 mg/m²/day (or 560 mg/m²/day, 570 mg/m²/day, 580 mg/m²/day, or 590 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is 600 mg/m²/day (or 610 mg/m²/day, 620 mg/m²/day, 630 mg/m²/day, or 640 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is 650 mg/m²/day (or 660 mg/m²/day, 670 mg/m²/day, 680 mg/m²/day, or 690 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is 700 mg/m²/day (or 710 mg/m²/day, 720 mg/m²/day, 730 mg/m²/day, or 740 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is 750 mg/m²/day (or 760 mg/m²/day, 770 mg/m²/day, 780 mg/m²/day, or 790 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is 800 mg/m²/day (or 810 mg/m²/day, 820 mg/m²/day, 830 mg/m²/day, or 840 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is 850 mg/m²/day (or 860 mg/m²/day, 870 mg/m²/day, 880 mg/m²/day, or 890 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is 900 mg/m²/day (or 910 mg/m²/day, 920 mg/m²/day, 930 mg/m²/day, or 940 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is 950 mg/m²/day (or 960 mg/m²/day, 970 mg/m²/day, 980 mg/m²/day, or 990 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In some embodiments, the dose of cyclophosphamide is 1000 mg/m²/day (or 1010 mg/m²/day, 1020 mg/m²/day, 1030 mg/m²/day, or 1040 mg/m²/day) and the dose of fludarabine is 5 mg/m²/day, 10 mg/m²/day, 15 mg/m²/day, 20 mg/m²/day, 25 mg/m²/day, 30 mg/m²/day, 35 mg/m²/day, 40 mg/m²/day, 45 mg/m²/day, 50 mg/m²/day, 55 mg/m²/day, 60 mg/m²/day, 65 mg/m²/day, 70 mg/m²/day, or 75 mg/m²/day.

In other embodiments, the dose of cyclophosphamide is between 100 mg/m$^2$/day and 650 mg/m$^2$/day, and the dose of fludarabine is between 10 mg/m$^2$/day and 50 mg/m$^2$/day. In other embodiments, the dose of cyclophosphamide is between 150 mg/m$^2$/day and 600 mg/m$^2$/day, and the dose of fludarabine is between 20 mg/m$^2$/day and 50 mg/m$^2$/day. In other embodiments, the dose of cyclophosphamide is between 200 mg/m$^2$/day and 550 mg/m$^2$/day, and the dose of fludarabine is between 20 mg/m$^2$/day and 40 mg/m$^2$/day. In other embodiments, the dose of cyclophosphamide is between 250 mg/m$^2$/day and 550 mg/m$^2$/day, and the dose of fludarabine is between 15 mg/m$^2$/day and 45 mg/m$^2$/day.

In certain embodiments, the dose of cyclophosphamide is 1000 mg/m$^2$/day, and the dose of fludarabine is 60 mg/m$^2$/day, 65 mg/m$^2$/day, 70 mg/m$^2$/day, 75 mg/m$^2$/day, 80 mg/m$^2$/day, 85 mg/m$^2$/day, 90 mg/m$^2$/day, 95 mg/m$^2$/day, 100 mg/m$^2$/day, 105 mg/m$^2$/day, 110 mg/m$^2$/day, 115 mg/m$^2$/day, 120 mg/m$^2$/day, 125 mg/m$^2$/day, 130 mg/m$^2$/day, 135 mg/m$^2$/day, 140 mg/m$^2$/day, 145 mg/m$^2$/day, 150 mg/m$^2$/day, 155 mg/m$^2$/day, 160 mg/m$^2$/day, 165 mg/m$^2$/day, 170 mg/m$^2$/day, 175 mg/m$^2$/day, 180 mg/m$^2$/day, 185 mg/m$^2$/day, 190 mg/m$^2$/day, 195 mg/m$^2$/day, 200 mg/m$^2$/day, 205 mg/m$^2$/day, 210 mg/m$^2$/day, 215 mg/m$^2$/day, 220 mg/m$^2$/day, 225 mg/m$^2$/day, 230 mg/m$^2$/day, 235 mg/m$^2$/day, 240 mg/m$^2$/day, 245 mg/m$^2$/day, or 250 mg/m$^2$/day.

In one embodiment, a dose of cyclophosphamide is about 500 mg/m$^2$/day and a dose of fludarabine is about 60 mg/m$^2$/day. In another embodiment, a dose of cyclophosphamide is about 300 mg/m$^2$/day and a dose of fludarabine is about 30 mg/m$^2$/day. In another embodiment, a dose of cyclophosphamide is about 200 mg/m$^2$/day and a dose of fludarabine is about 20 mg/m$^2$/day. In another embodiment, a dose of cyclophosphamide is about 200 mg/m$^2$/day and a dose of fludarabine is about 30 mg/m$^2$/day. In another embodiment, a dose of cyclophosphamide is about 500 mg/m$^2$/day and a dose of fludarabine is about 30 mg/m$^2$/day. In another embodiment, a dose of cyclophosphamide is about 300 mg/m$^2$/day and a dose of fludarabine is about 60 mg/m$^2$/day. In another embodiment, a dose of cyclophosphamide is about 500 mg/m$^2$/day and a dose of fludarabine is about 60 mg/m$^2$/day. In another embodiment, a dose of cyclophosphamide is about 1110 mg/m$^2$/day and a dose of fludarabine is about 25 mg/m$^2$/day. In another embodiment, a dose of cyclophosphamide is about 2220 mg/m$^2$/day and a dose of fludarabine is about 25 mg/m$^2$/day, wherein the patient exhibits increased serum levels of IL-7, IL-15, IL-10, IL-5, IP-10, IL-8, MCP-1, PLGF, CRP, sICAM-1, sVCAM-1, or any combination thereof, e.g., IL-15, IP-10, and/or IL-7, or decreased serum levels of perforin and/or MIP-1b after the administration of the cyclophosphamide and fludarabine. In another embodiment, a dose of cyclophosphamide is about 60 mg/kg/day and a dose of fludarabine is about 25 mg/m$^2$/day, wherein the patient exhibits increased serum levels of IL-7, IL-15, IL-10, IL-5, IP-10, IL-8, MCP-1, PLGF, CRP, sICAM-1, sVCAM-1, or any combination thereof, e.g., IL-15, IP-10, and/or IL-7, or decreased serum levels of perforin and/or MIP-1b after the administration of the cyclophosphamide and fludarabine. In another embodiment, a dose of cyclophosphamide is about 30 mg/kg/day and a dose of fludarabine is about 25 mg/m$^2$/day. In one particular embodiment, the cyclophosphamide is administered before, after, or concurrently with fludarabine. In a certain embodiment, the cyclophosphamide is administered before fludarabine.

The timing of the administration of the one or more preconditioning agents can be adjusted to maximize effect. In certain embodiments, the one or more preconditioning agents comprise at two or more preconditioning agents. The two or more preconditioning agents can be administered concurrently or sequentially. In one particular embodiment, a first preconditioning agent, e.g., cyclophosphamide, is administered to the patient prior to or after a second preconditioning agent, e.g., fludarabine.

The doses of cyclophosphamide and fludarabine can be raised or lowered together or independently. For example, the dose of cyclophosphamide can be increased while the dose of fludarabine is decreased, and the dose of cyclophosphamide can be decreased while the dose of fludarabine is increased. Alternatively, the dose of both cyclophosphamide and fludarabine can be increased or decreased together. In some embodiments, the dose of cyclophosphamide is 300 mg/m$^2$/day and the dose of fludarabine is 20 mg/m$^2$/day. In other embodiments, the dose of cyclophosphamide is 300 mg/m$^2$/day and the dose of fludarabine is 30 mg/m$^2$/day. In other embodiments, the dose of cyclophosphamide is 300 mg/m$^2$/day and the dose of fludarabine is 60 mg/m$^2$/day. In other embodiments, the dose of cyclophosphamide is 500 mg/m$^2$/day and the dose of fludarabine is 20 mg/m$^2$/day. In other embodiments, the dose of cyclophosphamide is 500 mg/m$^2$/day and the dose of fludarabine is 30 mg/m$^2$/day. In other embodiments, the dose of cyclophosphamide is 500 mg/m$^2$/day and the dose of fludarabine is 60 mg/m$^2$/day. In other embodiments, the dose of cyclophosphamide is 200 mg/m$^2$/day and the dose of fludarabine is 20 mg/m$^2$/day. In other embodiments, the dose of cyclophosphamide is 200 mg/m$^2$/day and the dose of fludarabine is 30 mg/m$^2$/day. In other embodiments, the dose of cyclophosphamide is 200 mg/m$^2$/day and the dose of fludarabine is 60 mg/m$^2$/day.

As described herein, the day that a T cell therapy is administered is designated as day 0. The one or more preconditioning agents can be administered at any time prior to administration of the T cell therapy. In some embodiments, the administration of the one or more preconditioning agents begins at least seven days, at least six days, at least five days, at least four days, at least three days, at least two days, or at least one day prior to the administration of the T cell therapy. In other embodiments, the administration of the one or more preconditioning agents begins at least eight days, at least nine days, at least ten days, at least eleven days, at least twelve days, at least thirteen days, or at least fourteen days prior to the administration of the T cell therapy. In one embodiment, the administration of the one or more preconditioning agents begins about seven days prior to the administration of the T cell therapy. In another embodiment, the administration of the one or more preconditioning agents begins about five days prior to the administration of the T cell therapy.

In one embodiment, the administration of a first preconditioning agent begins about seven days prior to the administration of the T cell therapy, and the administration of a second preconditioning agent begins about five days prior to administration of the T cell therapy. In one particular embodiment, a first preconditioning agent is administered to the patient for two days at about seven days and about six days prior to the administration of the T cell therapy. In another embodiment, a second preconditioning agent is administered to the patient for five days at about five, four, three, two, and one day prior to the administration of the T cell therapy. In another embodiment, a first preconditioning agent is administered to the patient for three days at about five, four, and three days prior to the administration of the T cell therapy.

In one particular embodiment, administration of the cyclophosphamide begins about seven days prior to the administration of the T cell therapy, and the administration of a purine analog (e.g., fludarabine or pentostatin) begins about five days prior to the administration of the T cell therapy. In another embodiment, administration of the cyclophosphamide begins about five days prior to the administration of the T cell therapy, and the administration of a purine analog (e.g., fludarabine or pentostatin) begins about five days prior to the administration of the T cell therapy.

The timing of the administration of each component can be adjusted to maximize effect. In general, the one or more preconditioning agents can be administered daily. In some embodiments, the one or more preconditioning agents are administered daily for about two days, for about three days, for about four days, for about five days, for about six days, or for about seven days. In some embodiments, the one or more preconditioning agents can be administered daily for at least one day, at least two days, at least three days, at least four days, at least five days, at least six days, or at least seven days. In one particular embodiment, the one or more preconditioning agents are administered daily for about three days.

As described herein, the day the T cell therapy is administered to the patient is designated as day 0. In some embodiments, the one or more preconditioning agents, e.g., the cyclophosphamide, is administered to the patient on day 7 and day 6 prior to day 0 (i.e., day −7 and day −6). In other embodiments, the one or more preconditioning agents, e.g., the cyclophosphamide, is administered to the patient on day −5, day −4, and day −3. In some embodiments, the one or more preconditioning agents, e.g., the fludarabine, is administered to the patient on day −5, day −4, day −3, day −2, and day −1. In other embodiments, the one or more preconditioning agents, e.g., fludarabine, is administered to the patient on day −5, day −4, and day −3.

The one or more preconditioning agents, e.g., the cyclophosphamide and fludarabine, can be administered on the same or different days. If cyclophosphamide and fludarabine are administered on the same day, the cyclophosphamide dose can be administered either before or after the fludarabine dose. In one embodiment, the cyclophosphamide dose is administered to the patient on day −7 and day −6, and the fludarabine dose is administered to the patient on day −5, day −4, day −3, day −2, and day −1. In another embodiment, the cyclophosphamide dose is administered to the patient on day −5, day −4, and day −3, and the fludarabine dose is administered to the patient on day −5, day −4, and day −3.

In certain embodiments, the one or more preconditioning agents, e.g., cyclophosphamide and fludarabine, can be administered concurrently or sequentially. In one embodiment, cyclophosphamide is administered to the patient prior to fludarabine. In another embodiment, cyclophosphamide is administered to the patient after fludarabine.

The one or more preconditioning agents can be administered by any route, including intravenously (IV) or orally. In some embodiments, the one or more preconditioning agents, e.g., the cyclophosphamide, is administered by IV over about 30 minutes, over about 35 minutes, over about 40 minutes, over about 45 minutes, over about 50 minutes, over about 55 minutes, over about 60 minutes, over about 90 minutes, over about 120 minutes. In some embodiments, the one or more preconditioning agents, e.g., the fludarabine, is administered by IV over about 10 minutes, over about 15 minutes, over about 20 minutes, over about 25 minutes, over about 30 minutes, over about 35 minutes, over about 40 minutes, over about 45 minutes, over about 50 minutes, over about 55 minutes, over about 60 minutes, over about 90 minutes, over about 120 minutes.

In certain embodiments, a T cell therapy is administered to the patient following administration of the one or more preconditioning agents, e.g., cyclophosphamide and fludarabine. In some embodiments, the T cell therapy comprises an adoptive cell therapy. In certain embodiments, the adoptive cell therapy is selected from tumor-infiltrating lymphocyte (TIL) immunotherapy, autologous cell therapy, engineered autologous cell therapy (eACT), and allogeneic T cell transplantation. In one particular embodiment, the eACT comprises administration of engineered antigen specific chimeric antigen receptor (CAR) positive (+) T cells. In another embodiment, the eACT comprises administration of engineered antigen specific T cell receptor (TCR) positive (+) T cells. In some embodiments the engineered T cells treat a tumor in the patient.

Various other interventions may be included in the methods described herein. For example, it is well known that preconditioning agents, e.g., cyclophosphamide and fludarabine, can cause adverse events in patients following administration. It is within the scope of the invention that compositions can also be administered to the patient to reduce some of these adverse events. In some embodiments, the method further comprises administering a saline solution to the patient. The saline solution can be administered to the patient either prior to or after the administration of the one or more preconditioning agents, or both before and after the administration of the one or more preconditioning agents. In certain embodiments, the saline solution is administered concurrently with the one or more preconditioning agents. In one particular embodiment, a saline solution is administered to the patient prior to the administration of the one or more preconditioning agents and following the administration of the one or more preconditioning agents on the day of each infusion.

The saline solution can be administered to the patient by any route, including, e.g., intravenously or orally. In some embodiments, the method comprises administering about 0.1 L, about 0.2 L, about 0.3 L, about 0.4 L, about 0.5 L, about 0.6 L, about 0.7 L, about 0.8 L, about 0.9 L, about 1 L, about 1.1 L, about 1.2 L, about 1.3 L, about 1.4 L, about 1.5 L, about 1.6 L, about 1.7 L, about 1.8 L, about 1.9 L, or about 2.0 L of saline solution. The NaCl of the saline solution can be dissolved to a final concentration of about 0.1%, about 0.2%, about 0.3%, about 0.4%, about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, or about 2.0%. In one embodiment, the method comprises administering 1.0 L of 0.9% NaCl saline solution to the patient. In one particular embodiment, the method comprises administering 1.0 L of 0.9% NaCl saline solution to the patient prior to the administration of the one or more preconditioning agents and following the administration of the one or more preconditioning agents on the day of each infusion.

Further, adjuvants and excipients can also be administered to the patient. For example, mesna (sodium 2-sulfanylthanesulfonate) is an adjuvant that acts as a detoxifying agent to inhibit hemorrhagic cystitis and hematuria, which can occur following treatment with cyclophosphamide. Cyclophosphamide, in vivo, can be converted to urotoxic metabolites, such as acrolein. Mesna assists to detoxify these metabolites by reaction of its sulfhydryl group with the vinyl group. It also increases urinary excretion of cysteine. In certain embodiments, the method further comprises administering mesna to the patient. The mesna can be administered prior to the administration of the cyclophosphamide and/or fludarabine, after the administration of the cyclophosphamide and/or fludarabine, or both prior to and after the administration of the of the cyclophosphamide and/or fludarabine. In one embodiment, Mesna is administered intravenously or orally (per mouth). For example, oral mesna can be given with oral cyclophosphamide.

In addition, exogenous cytokines may also be administered to the patient in the method described herein. As discussed above, it is hypothesized that reducing the number of endogenous lymphocytes increases the bioavailability of endogenous molecules, such as cytokines, that can favor the expansion, activation, and trafficking of adoptively transferred T cells. Accordingly, various cytokines may be administered to the patient. In one embodiment, the method further comprises administering one or more doses of IL-2, IL-15, IL-7, IL-10, IL-5, IP-10, IL-8, MCP-1, PLGF, CRP, sICAM-1, sVCAM-1, or any combination thereof. In one particular embodiment, the method comprises administering one or more doses of IL-2. The dose of IL-2 can be at least about 10,000 IU/kg, at least about 50,000 IU/kg, at least about 100,000 IU/kg, at least about 200,000 IU/kg, at least about 400,000 IU/kg, at least about 600,000 IU/kg, at least about 700,000 IU/kg, at least about 800,000 IU/kg, or at least about 1,000,000 IU/kg.

T Cell Therapy

The present invention provides methods for treating a cancer in a patient suitable for a T cell therapy comprising preconditioning the patient by administering to the patient one or more preconditioning agents that are capable of increasing a serum level of IL-15, IL-7, and at least one additional cytokine selected from the group consisting of MCP-1, CRP, PLGF, IP-10, and any combination thereof, wherein the patient is treated with a T cell therapy when exhibiting an increased serum level of IL-15, IL-7, and the at least one additional cytokine. Because the preconditioning regimen serves to modify the immune environment through induction of IL-15, IL-7, and at least one additional cytokine, which can favor the homeostatic expansion, activation, and trafficking of T cells in general, various different T cell therapies can benefit from the conditioning methods described herein. One of skill in the art would understand that the methods can be applied to any method of treating a patient comprising administering to the patient one or more T cells.

For example, and without limitation, the methods described herein can enhance the effectiveness of a T cell therapy, which can be an adoptive T cell therapy selected from the group consisting of tumor-infiltrating lymphocyte (TIL) immunotherapy, autologous cell therapy, engineered autologous cell therapy (eACT), allogeneic T cell transplantation, non-T cell transplantation, and any combination thereof. Adoptive T cell therapy broadly includes any method of selecting, enriching in vitro, and administering to a patient autologous or allogeneic T cells that recognize and are capable of binding tumor cells. TIL immunotherapy is a type of adoptive T cell therapy, wherein lymphocytes capable of infiltrating tumor tissue are isolated, enriched in vitro, and administered to a patient. The TIL cells can be either autologous or allogeneic. Autologous cell therapy is an adoptive T cell therapy that involves isolating T cells capable of targeting tumor cells from a patient, enriching the T cells in vitro, and administering the T cells back to the same patient. Allogeneic T cell transplantation can include transplant of naturally occurring T cells expanded ex vivo or genetically engineered T cells. Engineered autologous cell therapy, as described in more detail above, is an adoptive T cell therapy wherein a patient's own lymphocytes are isolated, genetically modified to express a tumor targeting molecule, expanded in vitro, and administered back to the patient. Non-T cell transplantation can include autologous or allogeneic therapies with non-T cells such as, but not limited to, natural killer (NK) cells.

In one particular embodiment, the T cell therapy of the present invention is engineered Autologous Cell Therapy (eACT™). According to this embodiment, the method can include collecting blood cells from the patient prior to the administration of the one or more preconditioning agents. The isolated blood cells (e.g., T cells) can then be engineered to express a chimeric antigen receptor ("engineered CAR T cells") or T cell receptor ("engineered TCR T cells"). In some embodiments, the T cell therapy comprises engineered CAR T cell therapy or the engineered TCR T cell therapy. In a particular embodiment, the engineered CAR T cells or the engineered TCR T cells are administered to the patient after administering the one or more preconditioning agents. In some embodiments, the engineered CAR T cells or the engineered TCR T cells treat a tumor in the patient. In one embodiment the engineered CAR T reduce the size of a tumor. In another embodiment, the engineered TCR T cells reduce the size of a tumor.

In one embodiment, the T cells is engineered to express a chimeric antigen receptor. The chimeric antigen receptor can comprise binding molecule to a tumor antigen. The binding molecule can be an antibody or an antigen binding molecule thereof. For example, the antigen binding molecule can be selected from scFv, Fab, Fab', Fv, F(ab')2, and dAb, and any fragments or combinations thereof.

The chimeric antigen receptor can further comprise a hinge region. The hinge region can be derived from the hinge region of IgG1, IgG2, IgG3, IgG4, IgA, IgD, IgE, IgM, CD28, or CD8 alpha. In one particular embodiment, the hinge region is derived from the hinge region of IgG4.

The chimeric antigen receptor can also comprise a transmembrane domain. The transmembrane domain can be a transmembrane domain of any transmembrane molecule that is a co-receptor on immune cells or a transmembrane domain of a member of the immunoglobulin superfamily. In certain embodiments, the transmembrane domain is derived from a transmembrane domain of CD28, CD8 alpha, CD4, or CD19. In one particular embodiment, the transmembrane domain comprises a domain derived from a CD28 transmembrane domain.

The chimeric antigen receptor can further comprise one or more costimulatory signaling regions. For example, the costimulatory signaling region can be a signaling region of CD28, OX-40, 4-1BB, CD27, inducible T cell costimulator (ICOS), CD3 gamma, CD3 delta, CD3 epsilon, CD247, Ig alpha (CD79a), or Fc gamma receptor. In one particular embodiment, the costimulatory signaling region is a CD28 signaling region.

In one embodiment, the chimeric antigen receptor further comprises a CD3 zeta signaling domain.

The chimeric antigen receptor can be engineered to target a particular tumor antigen. In some embodiments, the tumor antigen is selected from CD19 CD20, ROR1, CD22, carcinoembryonic antigen, alphafetoprotein, CA-125, 5T4, MUC-1, epithelial tumor antigen, prostate-specific antigen, melanoma-associated antigen, mutated p53, mutated ras, HER2/Neu, folate binding protein, HIV-1 envelope glycoprotein gp120, HIV-1 envelope glycoprotein gp41, GD2, CD123, CD33, CD138, CD23, CD30, CD56, c-Met, mesothelin, GD3, HERV-K, IL-11Ralpha, kappa chain, lambda chain, CSPG4, ERBB2, EGFRvIII, VEGFR2, HER2-HER3 in combination, HER1-HER2 in combination, and any combination thereof. In one particular embodiment, the tumor antigen is CD19.

In another embodiment, the T cell therapy comprises administering to the patient engineered T cells expressing T cell receptor ("engineered TCR T cells"). The T cell receptor (TCR) can comprise a binding molecule to a tumor antigen. In some embodiments, the tumor antigen is selected from the group consisting of CD19, CD20, ROR1, CD22, carcinoembryonic antigen, alphafetoprotein, CA-125, 5T4, MUC-1, epithelial tumor antigen, prostate-specific antigen, melanoma-associated antigen, mutated p53, mutated ras, HER2/Neu, folate binding protein, HIV-1 envelope glycoprotein gp120, HIV-1 envelope glycoprotein gp41, GD2, CD123, CD33, CD138, CD23, CD30, CD56, c-Met, mesothelin, GD3, HERV-K, IL-11Ralpha, kappa chain, lambda chain, CSPG4, ERBB2, EGFRvIII, VEGFR2, HER2-HER3 in combination, HER1-HER2 in combination, and any combination thereof.

In one embodiment, the TCR comprises a binding molecule to a viral oncogene. In one particular embodiment, the viral oncogene is selected from human papliloma virus (HPV), Epstein-Barr virus (EBV), and human T-lymphotropic virus (HTLV).

In still another embodiment, the TCR comprises a binding molecule to a testicular, placental, or fetal tumor antigen. In one particular embodiment, the testicular, placental, or fetal tumor antigen is selected from the group consisting of NY-ESO-1, synovial sarcoma X breakpoint 2 (SSX2), melanoma antigen (MAGE), and any combination thereof.

In another embodiment, the TCR comprises a binding molecule to a lineage specific antigen. In one particular embodiment, the lineage specific antigen is selected from the group consisting of melanoma antigen recognized by T cells 1 (MART-1), gp100, prostate specific antigen (PSA), prostate specific membrane antigen (PSMA), prostate stem cell antigen (PSCA), and any combination thereof.

In one embodiment, the T cell therapy comprises administering to the patient engineered CAR T cells expressing a chimeric antigen receptor that binds to CD19 and further comprises a CD28 costimulatory domain and a CD3-zeta signaling region. In a particular embodiment, the T cell therapy comprises administering to a patient KTE-C19.

The T cell therapy included in the present invention involves the transfer of T cells to a patient. The T cells can be administered at a therapeutically effective amount. For example, a therapeutically effective amount of T cells, e.g., engineered CAR+ T cells or engineered TCR+ T cells, can be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the T cells, e.g., engineered CAR+ T cells or engineered TCR+ T cells, is about $10^4$ cells, about $10^5$ cells, about $10^6$ cells, about $10^7$ cells, or about $10^8$ cells. In one particular embodiment, the therapeutically effective amount of the T cells, e.g., engineered CAR+ T cells or engineered TCR+ T cells, is about $1\times10^5$ cells/kg, about $2\times10^5$ cells/kg, about $3\times10^5$ cells/kg, about $4\times10^5$ cells/kg, about $5\times10^5$ cells/kg, about $6\times10^5$ cells/kg, about $7\times10^5$ cells/kg, about $8\times10^5$ cells/kg, about $9\times10^5$ cells/kg, about $1\times10^6$ cells/kg, about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg. In one particular embodiment, the therapeutically effective amount of the T cells, e.g., engineered CAR+ T cells or engineered TCR+ T cells, is about $2\times10^6$ cells/kg.

In other embodiments, the therapeutically effective amount of the T cells, e.g., engineered CAR+ T cells or engineered TCR+ T cells, is from about $1.0\times10^5$ cells/kg to about $2\times10^8$ cells/kg, from about $2.0\times10^5$ cells/kg to about $2\times10^8$ cells/kg, from about $3.0\times10^5$ cells/kg to about $2\times10^8$ cells/kg, from about $4.0\times10^5$ cells/kg to about $2\times10^8$ cells/kg, from about $5.0\times10^5$ cells/kg to about $2\times10^8$ cells/kg, from about $6.0\times10^5$ cells/kg to about $2\times10^8$ cells/kg, from about $7.0\times10^5$ cells/kg to about $2\times10^8$ cells/kg, from about $8.0\times10^5$ cells/kg to about $2\times10^8$ cells/kg, from about $9.0\times10^5$ cells/kg to about $2\times10^8$ cells/kg, from about $0.5\times10^6$ cells/kg to about $2\times10^8$ cells/kg, from about $2\times10^6$ cells/kg to about $9\times10^7$ cells/kg, from about $3\times10^6$ cells/kg to about $9\times10^7$ cells/kg, from about $4\times10^6$ cells/kg to about $9\times10^7$ cells/kg, from about $5\times10^6$ cells/kg to about $9\times10^7$ cells/kg, from about $6\times10^6$ cells/kg to about $9\times10^7$ cells/kg, from about $7\times10^6$ cells/kg to about $9\times10^7$ cells/kg, from about $8\times10^6$ cells/kg to about $9\times10^7$ cells/kg, from about $9\times10^6$ cells/kg to about $9\times10^7$ cells/kg, from about $1\times10^7$ cells/kg to about $9\times10^7$ cells/kg, from about $2\times10^7$ cells/kg to about $9\times10^7$ cells/kg, from about $3\times10^7$ cells/kg to about $9\times10^7$ cells/kg, from about $4\times10^7$ cells/kg to about $9\times10^7$ cells/kg, from about $5\times10^7$ cells/kg to about $9\times10^7$ cells/kg, from about $6\times10^7$ cells/kg to about $9\times10^7$ cells/kg, from about $7\times10^7$ cells/kg to about $9\times10^7$ cells/kg, from about $8\times10^7$ cells/kg to about $9\times10^7$ cells/kg, from about $2\times10^6$ cells/kg to about $8\times10^7$ cells/kg, from about $2\times10^6$ cells/kg to about $7\times10^7$ cells/kg, from about $2\times10^6$ cells/kg to about $6\times10^7$ cells/kg, from about $2\times10^6$ cells/kg to about $5\times10^7$ cells/kg, from about $2\times10^6$ cells/kg to about $4\times10^7$ cells/kg, from about $2\times10^6$ cells/kg to about $3\times10^7$ cells/kg, from about $2\times10^6$ cells/kg to about $2\times10^7$ cells/kg, from about $2\times10^6$ cells/kg to about $1\times10^7$ cells/kg, from about $2\times10^6$ cells/kg to about $9\times10^6$ cells/kg, from about $2\times10^6$ cells/kg to about $8\times10^6$ cells/kg, from about $2\times10^6$ cells/kg to about $7\times10^6$ cells/kg, from about $2\times10^6$ cells/kg to about $6\times10^6$ cells/kg, from about $2\times10^6$ cells/kg to about $5\times10^6$ cells/kg, from about $2\times10^6$ cells/kg to about $4\times10^6$ cells/kg, from about $2\times10^6$ cells/kg to about $3\times10^6$ cells/kg, from about $3\times10^6$ cells/kg to about $8\times10^7$ cells/kg, from about $4\times10^6$ cells/kg to about $7\times10^7$ cells/kg, from about $5\times10^6$ cells/kg to about $6\times10^7$ cells/kg, from about $6\times10^6$ cells/kg to about $5\times10^7$ cells/kg, from about $7\times10^6$ cells/kg to about $4\times10^7$ cells/kg, from about $8\times10^6$ cells/kg to about $3\times10^7$ cells/kg, or from about $9\times10^6$ cells/kg to about $2\times10^7$ cells/kg. In one embodiment, the therapeutically effective amount of the engineered CAR T cells is from about $0.8\times10^6$ cells/kg to about $1.2\times10^6$ T cells/kg. In one particular embodiment, the therapeutically effective amount of the engineered CAR T cells is $2.0\times10^5$ cells/kg. In one particular embodiment, the therapeutically effective amount of the engineered CART cells is $1.0\times10^6$ cells/kg.

Cancer Treatment

The methods of the invention can be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In certain embodiments, the methods induce a complete response. In other embodiments, the methods induce a partial response.

Cancers that may be treated include tumors that are not vascularized, not yet substantially vascularized, or vascularized. The cancer may also include solid or non-solid tumors. In certain embodiments, the cancer can be selected from a tumor derived from bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, T-cell rich B cell lymphoma (TCRBCL), Primary mediastinal large B cell lymphoma (PMBCL), non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In one embodiment, the method can be used to treat a tumor, wherein the tumor is a lymphoma or a leukemia. Lymphoma and leukemia are cancers of the blood that specifically affect lymphocytes. All leukocytes in the blood originate from a single type of multipotent hematopoietic stem cell found in the bone marrow. This stem cell produces both myeloid progenitor cells and lymphoid progenitor cell, which then give rise to the various types of leukocytes found in the body. Leukocytes arising from the myeloid progenitor cells include T lymphocytes (T cells), B lymphocytes (B cells), natural killer cells, and plasma cells. Leukocytes arising from the lymphoid progenitor cells include megakaryocytes, mast cells, basophils, neutrophils, eosinophils, monocytes, and macrophages. Lymphomas and leukemias can affect one or more of these cell types in a patient.

In general, lymphomas can be divided into at least two sub-groups: Hodgkin lymphoma and non-Hodgkin lymphoma. Non-Hodgkin Lymphoma (NHL) is a heterogeneous group of cancers originating in B lymphocytes, T lymphocytes or natural killer cells. In the United States, B cell lymphomas represent 80-85% of cases reported. In 2013 approximately 69,740 new cases of NHL and over 19,000 deaths related to the disease were estimated to occur. Non-Hodgkin lymphoma is the most prevalent hematological malignancy and is the seventh leading site of new cancers among men and women and account for 4% of all new cancer cases and 3% of deaths related to cancer.

Diffuse large B cell lymphoma (DLBCL) is the most common subtype of NHL, accounting for approximately 30% of NHL cases. There are approximately 22,000 new diagnoses of DLBCL in the United States each year. It is classified as an aggressive lymphoma with the majority of patients cured with conventional chemotherapy (NCCN guidelines NHL 2014).

First line therapy for DLBCL typically includes an anthracycline-containing regimen with rituximab, such as R-CHOP (rituximab, cyclophosphamide, doxorubicin, vincristine, and prednisone), which has an objective response rate of about 80% and a complete response rate of about 50% (Coiffier 2002), with about one-third of patients have refractory disease to initial therapy or relapse after R-CHOP (Sehn 2005). For those patients who relapse after response to first line therapy, approximately 40-60% of patients can achieve a second response with additional chemotherapy. The standard of care for second-line therapy for autologous stem cell transplant (ASCT) eligible patients includes rituximab and combination chemotherapy such as R-ICE (rituximab, ifosfamide, carboplatin, and etoposide) and R-DHAP (rituximab, dexamethasone, cytarabine, and cisplatin), which each have an objective response rate of about 63% and a complete response rate of about 26% (Gisselbrecht 2010). Patients who respond to second line therapy and who are considered fit enough for transplant receive consolidation with high-dose chemotherapy and ASCT, which is curative in about half of transplanted patients (Gisselbrecht 2010). Patients who failed ASCT have a very poor prognosis and no curative options.

Primary mediastinal large B cell lymphoma (PMBCL) has distinct clinical, pathological, and molecular characteristics compared to DLBCL. PMBCL is thought to arise from thymic (medullary) B cells and represents approximately 3% of patients diagnosed with DLBCL. PMBCL is typically identified in the younger adult population in the fourth decade of life with a slight female predominance. Gene expression profiling suggests deregulated pathways in PMBCL overlap with Hodgkin lymphoma. Initial therapy of PMBCL generally includes anthracycline-containing regimens with rituximab, such as infusional dose-adjusted etoposide, doxorubicin, and cyclophosphamide with vincristine, prednisone, and rituximab (DA-EPOCH-R), with or without involved field radiotherapy.

Follicular lymphoma (FL), a B cell lymphoma, is the most common indolent (slow-growing) form of NHL, accounting for approximately 20% to 30% of all NHLs. Some patients with FL will transform (TFL) histologically to DLBCL which is more aggressive and associated with a poor outcome. Histological transformation to DLBCL occurs at an annual rate of approximately 3% for 15 years with the risk of transformation continuing to drop in subsequent years. The biologic mechanism of histologic transformation is unknown. Initial treatment of TFL is influenced by prior therapies for follicular lymphoma but generally includes anthracycline-containing regimens with rituximab to eliminate the aggressive component of the disease.

Treatment options for relapsed/refractory PMBCL and TFL are similar to those in DLBCL. Given the low prevalence of these diseases, no large prospective randomized studies in these patient populations have been conducted. Patients with chemotherapy refractory disease have a similar or worse prognosis to those with refractory DLBCL.

In summary, subjects who have refractory, aggressive NHL (e.g., DLBCL, PMBCL and TFL) have a major unmet medical need and further research with novel treatments are warranted in these populations.

Accordingly, in some embodiments, the method can be used to treat a lymphoma or a leukemia, wherein the lymphoma or leukemia is a B cell malignancy. In some embodiments, the lymphoma or leukemia is selected from B-cell chronic lymphocytic leukemia/small cell lymphoma, B-cell prolymphocytic leukemia, lymphoplasmacytic lymphoma (e.g., Waldenström macroglobulinemia), splenic marginal zone lymphoma, hairy cell leukemia, plasma cell neoplasms (e.g., plasma cell myeloma (i.e., multiple myeloma), or plasmacytoma), extranodal marginal zone B cell lymphoma (e.g., MALT lymphoma), nodal marginal zone B cell lymphoma, follicular lymphoma (FL), transformed follicular lymphoma (TFL), primary cutaneous follicle center lymphoma, mantle cell lymphoma, diffuse large B cell lymphoma (DLBCL), Epstein-Barr virus-positive DLBCL, lymphomatoid granulomatosis, primary mediastinal (thymic) large B-cell lymphoma (PMBCL), Intravascular large B-cell lymphoma, ALK+ large B-cell lymphoma, plasmablastic lymphoma, primary effusion lymphoma, large B-cell lymphoma arising in HHV8-associated multicentric Castleman's disease, Burkitt lymphoma/leukemia, T-cell prolymphocytic leukemia, T-cell large granular lymphocyte leukemia, aggressive NK cell leukemia, adult T-cell leukemia/lymphoma, extranodal NK/T-cell lymphoma, enteropathy-associated T-cell lymphoma, Hepatosplenic T-cell lymphoma, blastic NK cell lymphoma, Mycosis fungoides/Sezary syndrome, Primary cutaneous anaplastic large cell lymphoma, Lymphomatoid papulosis, Peripheral T-cell lymphoma, Angioimmunoblastic T cell lymphoma, Anaplastic large cell lymphoma, B-lymphoblastic leukemia/lymphoma, B-lymphoblastic leukemia/lymphoma with recurrent genetic abnormalities, T-lymphoblastic leukemia/lymphoma, and Hodgkin lymphoma. In some embodiments, the cancer is refractory to one or more prior treatments, and/or the cancer has relapsed after one or more prior treatments.

In certain embodiments, the cancer is selected from follicular lymphoma, transformed follicular lymphoma, diffuse large B cell lymphoma, and primary mediastinal (thymic) large B-cell lymphoma. In one particular embodiment, the cancer is diffuse large B cell lymphoma.

In some embodiments, the cancer is refractory to or the cancer has relapsed following one or more of chemotherapy, radiotherapy, immunotherapy (including a T cell therapy and/or treatment with an antibody or antibody-drug conjugate), an autologous stem cell transplant, or any combination thereof. In one particular embodiment, the cancer is refractory diffuse large B cell lymphoma.

The present invention is further illustrated by the following examples which should not be construed as further limiting. The contents of all references cited throughout this application are expressly incorporated herein by reference.

EXAMPLES

Example 1

A phase 1/2, single arm, open label, trial was designed to determine the safety and feasibility of anti-CD19 CAR+ T cells administered to subjects with B cell malignancies.

Subjects who signed informed consent and met study eligibility were enrolled into the study and underwent leukapheresis to obtain PBMCs for the production of anti-CD19 CAR+ T cells. Subjects were treated with conditioning chemotherapy prior to hospitalization in preparation for a single infusion of anti-CD19 CAR+ T cells on Day 0. Some subjects were then treated with interleukin-2 (Group 1 only), 3 hours after the anti-CD19 CAR+ T cell infusion. Retreatment of a second dose of anti-CD19 CAR+ T cells was allowed if there was a response of partial response (PR) or complete response (CR) after the first infusion and then subsequent disease progression.

Three groups of subjects were enrolled. Group 1 includes 8 subjects, including 1 subject who was retreated, dosed with anti-CD19 CAR+ T cells ranging from $3\times10^6$ through $30\times10^6$ anti-CD19 CAR+ T cells/kg. The dose of anti-CD19 CAR+ T cells followed a conditioning regimen consisting of high dose cyclophosphamide at 60-120 mg/kg (2220-4440 mg/m$^2$) for two days followed by fludarabine at 25 mg/m$^2$ for five days. These subjects also received high dose interleukin-2 (IL-2) at 720,000 IU/kg (every 8 hours until 15 doses or toxicity precluded additional doses) after the anti-CD19 CAR+ T cell administration to stimulate their proliferation.

Group 2 includes 15 subjects, including 2 subjects from Group 1 who were retreated, who received high dose cyclophosphamide and fludarabine and no interleukin-2 following varying doses of anti-CD19 CAR+ T cell administration ($1\times10^6$ through $5\times10^6$ anti-CD19 CAR+ T cells/kg).

Group 3 includes 11 subjects, who have received a reduced conditioning regimen of cyclophosphamide at 300 mg/m$^2$ and fludarabine at 30 mg/m$^2$, both given for 3 concurrent days with no IL-2. The first 7 and last 4 of these subjects received an anti-CD19 CAR+ T cell infusion of $1\times10^6$ anti-CD19 CAR+ T cells and $2\times10^6$ anti-CD19 CAR+ T cells, respectively.

Demographics

Subject demographic and disease characteristics are provided in Table 1. Thirty-two (32) subjects were enrolled, 19 subjects (59%) had DLBCL or PMBCL, 7 subjects (22%) had CLL, and 6 subjects (19%) had other indolent NHL, including indolent follicular lymphoma and splenic marginal zone lymphoma. Most subjects had refractory disease (84%), and had received a median of 3 prior lines of therapy. All subjects with aggressive NHL received prior anti-CD20 therapy, platinum combination chemotherapy, and 95% received prior anthracycline-based chemotherapy.

Pharmacokinetics

The number of anti-CD19 CAR+ T cells in the peripheral blood at various time points after initial administration on Day 0 were evaluated using qPCR analysis and corroborated by standard curves generated by flow cytometry with an antibody reagent specific for scFv present in the anti-CD19 CAR construct (Kochenderfer et al., "B-cell depletion and remissions of malignancy along with cytokine-associated toxicity in a clinical trial of anti-CD19 chimeric-antigen-receptor-transduced T cells," Blood 119:2709-20 (2012)).

TABLE 1

| Demographics of clinical trial subjects. | | | | |
|---|---|---|---|---|
| | Group 1 (N = 8) | Group 2 (N = 15) | Group 3 (N = 11) | Total (N = 32) |
| Age (years) | | | | |
| Mean (std) | 56 (6) | 52 (11) | 50 (16) | 52 (12) |
| Median | 56 | 55 | 55 | 55 |
| Minimum, maximum | 47, 63 | 31, 69 | 29, 67 | 29, 69 |
| Gender | | | | |
| Male | 8 (100%) | 8 (53%) | 11 (100%) | 25 (78%) |
| Female | 0 (0%) | 7 (47%) | 0 (0%) | 7 (22%) |
| Race | | | | |
| White | 8 (100%) | 13 (87%) | 10 (91%) | 29 (91%) |
| Asian | 0 (0%) | 1 (7%) | 0 (0%) | 1 (3%) |

TABLE 1-continued

Demographics of clinical trial subjects.

| | Group 1 (N = 8) | Group 2 (N = 15) | Group 3 (N = 11) | Total (N = 32) |
|---|---|---|---|---|
| Black or African American | 0 (0%) | 1 (7%) | 0 (0%) | 1 (3%) |
| Unknown | 0 (0%) | 0 (0%) | 1 (9%) | 1 (3%) |
| Diagnosis | | | | |
| CLL FL | 4 (50%) | 4 (27%) | 0 (0%) | 7 (22%) |
| SMZL | 3 (38%) | 0 (0%) | 1 (9%) | 4 (13%) |
| iNHL | 1 (13%) | 1 (7%) | 0 (0%) | 1 (3%) |
| DLBCL | 0 (0%) | 1 (7%) | 0 (0%) | 1 (3%) |
| PMBCL | 0 (0%) | 5 (33%) | 8 (73%) | 13 (41%) |
|  | 0 (0%) | 4 (27%) | 2 (18%) | 6 (19%) |
| Prior anti-CD20 | 7 (88%) | 13 (87%) | 11 (100%) | 30 (94%) |
| Refractory to last line of therapy (SD/PD to last line) | | | | |
| Yes | 6 (75%) | 13 (87%) | 9 (82%) | 27 (84%) |
| No | 1 (13%) | 2 (13%) | 0 (0%) | 2 (6%) |
| Unknown | 1 (13%) | 0 (0%) | 2 (18%) | 3 (9%) |
| Lines of prior therapy | | | | |
| Median (minimum, maximum) | 4 (2, 7) | 3 (1, 12) | 3 (2, 10) | 3 (1, 12) |

In group 1, $3 \times 10^6$ to $30 \times 10^6$ anti-CD19 CAR+ T cells/kg were infused. In the first 6 subjects, the anti-CD19 CAR+ T cells in blood circulation were detected at higher levels within 2 weeks after infusion, reaching up to 0.02-1% of total PBMC, then decayed rapidly and were undetectable after 50 days. Subjects 7 and 8, dosed with the highest number of anti-CD19 CAR+ T cells (28 and $30 \times 10^6$ anti-CD19 CAR+ T cells/kg, respectively), had higher peak percentages reaching >10% anti-CD19 CAR+ T cells of total PBMC, and longer-term persistence of anti-CD19 CAR+ T cells in blood (>130 and 180 days, respectively).

In group 2, in the absence of interleukin-2 treatment, the anti-CD19 CAR+ T cells showed a similar expansion in the peripheral blood within 2 weeks, followed by decay and complete disappearance from circulation within several weeks (Table 2).

Overall, there was no overt relationship between the dose of anti-CD19 CAR+ T cells and their expansion and persistence in the peripheral blood. Likewise, to date, there was no apparent relationship between the anti-CD19 CAR+ T cell dose, the anti-CD19 CAR+ T cell expansion or persistence in the blood, and the clinical response or the toxicities related to this therapy, respectively.

In groups 1 and 2, there was no secondary expansion of anti-CD19 CAR+ T cells following their primary expansion at 7-14 days post-infusion. There is no evidence of oncogenic transformation ascribable to the genomic insertion of the CAR-expression retrovirus in the subjects tested to date. Group 3 results were not yet available at the time of data cutoff.

Efficacy

Clinicians evaluated 32 subjects for safety and 29 subjects for efficacy. The overall response rate for the 29 subjects evaluable for efficacy was 76%. Eleven (11) of 29 subjects (38%) achieved a CR and 11/29 subjects (38%) achieved a PR (FIGS. 2A and 2B; Table 3).

Sixteen of the 29 (55%) evaluable subjects remain in response from their first treatment, with 12 subject's (including retreated subjects) duration of response exceeding 1 year (Table 3). Three responding subjects were retreated after progression, all have ongoing responses (17.4 to over 52.2 months).

As indicated in Table 3, 17 of the 19 subjects with refractory aggressive DLBCL/PMBCL were evaluable for disease response (1 subject was not evaluable; 1 subject had not yet been evaluated). Among these 17 subjects, 11 (65%) had a response with 6/17 subjects (35%) achieving a CR. The median duration of response is 7.3 months.

TABLE 2

Anti-CD19 CAR+ T cell expansion and persistence in the peripheral blood of subjects in group 2.

| | Total dose of anti-CD19 CAR+ T cells ($\times 10^6$) | Dose range of anti-CD19 CAR+ T cells/ kg in millions ($\times 10^6$) | Anti-CD19 CAR+ T cell peak - expressed as number of cells/μL blood | Time to peak in days | Persistence of anti-CD19 CAR+ T cells in days |
|---|---|---|---|---|---|
| Mean | 210 | 3.1 | 50 | 10 | 32 |
| (Range) | (105-490) | (1.2-7.5) | (9-777) | (7-17) | (13-132) |

TABLE 3

Objective Response Rate and Duration of Response by Tumor Type.

| Tumor Type (n evaluable) | Overall Response Rate n (%) | Complete Response Rate n (%) | Duration of Response (months) Median (Individual) |
|---|---|---|---|
| Any (n = 29) | 22 (76%) | 11 (38%) | 14.9 |
| DLBCL/PMBCL (n = 17) | 11 (65%) | 6 (35%) | 7.3 (<1+, 1.0, 1.2, 5.3+, 6.0, 7.3, 7.9+, 14.1+, 15.7+, 20.3+, 28.5+) |
| CLL (n = 7) | 6 (86%) | 4 (57%) | 22.2 (2.8, 4.6, 17.1+, 27.2+, 31.1+, 35.6+) |
| Indolent NHL (n = 5) | 5 (100%) | 1 (20%) | 18.8 (10.4+, 17.1+, 18.8+, 45.4+, 58.5+) |

+indicates that the response is still ongoing

Six of the 7 evaluable subjects (86%) with CLL had a response with 4/7 subjects (57%) achieving a CR (Table 3). The median duration of response is 22.2 months with 4/7 subjects (57%) still in response including 3 subjects with ongoing responses for greater than 27 months (Table 3).

Five of the 5 evaluable subjects (100%) with indolent NHL had a response with 1/5 subjects (20%) achieving a CR. The median duration of response is 18.8 months (Table 3). Five subjects (5/5; 100%) remain in response with 2 subjects responding greater than 45 months (Table 4).

Safety

Adverse Events 32 subjects had been treated with the anti-CD19 CAR+ T cells with no adverse events yet reported for the last subject treated. Overall safety summaries include all 32 treated subjects. Summaries by group include safety data for subjects 1010003 and 1010004 twice, once when these subjects were treated in Group 1 and second when these subjects were treated in Group 2 (retreatment with anti-CD19 CAR+ T cells).

Summary of Adverse Events

A summary of adverse events is provided in Table 4. Overall, 31 subjects (97%) experienced any adverse event, with 0 subjects (0%) experiencing a worst grade of grade 3, 29 subjects (91%) experiencing a worst grade of grade 4, and 2 subjects (6%) with fatal adverse events. Twenty subjects (63%) experienced an anti-CD19 CAR+ T cell related adverse event; 6 subjects (19%) worst grade of 3, 8 subjects (25%) worst grade 4, and no subjects experienced a grade 5 event. Sixteen (16) subjects (50%) experienced a serious adverse event; 3 subjects (9%) worst grade of 3, 9 subjects (28%) worst grade of 4, and 2 subjects (6%) worst grade of 5.

Dose-Limiting Toxicity

The incidence of DLT within Groups 1, 2 and 3 was 38%, 40%, and 0%, respectively. With the exception of subject 1010002, DLTs were primarily neurotoxicities, 2 cases of elevated creatinine, and 1 event each of hypoxia and hypotension. Table 6 provides a listing of DLTs. In Group 3 there were no DLTs reported. The conditioning regimen in Group 3 was studied with $2 \times 10^6$ anti-CD19 CAR+ T cells/kg.

TABLE 4

Summary of Adverse Events.

| n (%) | Group 1 (N = 8) | Group 2 (N = 15) | Group 3 (N = 11) | Overall (N = 32) |
|---|---|---|---|---|
| Any Gr 2-5 AE | 8 (100) | 15 (100%) | 10 (91%) | 31 (97%) |
| Gr 3 | 0 (0) | 0 (0%) | 0 (0%) | 0 (0%) |
| Gr 4 | 7 (88%) | 14 (93%) | 10 (91%) | 29 (91%) |
| Gr 5 | 1 (13%) | 1 (7%) | 0 (0%) | 2 (6%) |
| Any Gr 2-5 CAR related | 3 (37%) | 11 (73%) | 7 (64%) | 20 (63%) |
| Gr 3 | 0 (0%) | 3 (20%) | 3 (27%) | 6 (19%) |
| Gr 4 | 2 (25%) | 6 (40%) | 0 (0%) | 8 (25%) |
| Gr 5 | 0 (0) | 0 (0%) | 0 (0%) | 0 (0%) |
| Any Serious | 6 (75%) | 8 (53%) | 2 (18%) | 16 (50%) |
| Gr 3 | 2 (25%) | 1 (7%) | 0 (0%) | 3 (9%) |
| Gr 4 | 2 (25%) | 6 (40%) | 1 (9%) | 9 (28%) |
| Gr 5 | 1 (13%) | 1 (7%) | 0 (0%) | 2 (6%) |

Cytokine Release Syndrome

Cytokine release is induced by the activated T cells upon engagement with the CD19 target. Using a broad search strategy, treatment-emergent adverse events which may be attributed to CRS include fever, febrile neutropenia, hypotension, acute vascular leak syndrome, elevated creatinine, renal failure, hypoxia, and pleural effusion. Twenty-eight (28) (88%) subjects reported adverse events which could be attributed to cytokine release, where 24 subjects (75%) reported a ≥grade 3 event and 6 subjects (19%) experienced a serious event. Adverse events due to co-therapies such as IL-2 (used in Group 1) and conditioning chemotherapy (causing febrile neutropenia) potentially confound this analysis.

Clinical manifestations of CRS occurred typically in the first week after anti-CD19 CAR+ T cell infusion and were less common in the subjects in Group 3. Only 1 of the 11 subjects in Group 3 experienced grade 3 hypotension, and 4 experienced grade 3 fever. Events of acute vascular leak syndrome, oliguria, elevated creatinine, and renal failure were reported only in subjects in Groups 1 and 2.

TABLE 5

Dose-Limiting Toxicities.

| Subject No. | Anti-CD19 CAR+ T cells/kg | Dose-Limiting Toxicities (DLT) | Group | Comment |
|---|---|---|---|---|
| 1010002 | $3 \times 10^6$ | G4 hypoxia G4 influenza infection G5 thrombosis (cerebral thrombi with global infarction) | 1 | The subject had a culture-proven H1N1 viral pneumonia and died 18 days after his infusion. |
| 1010004 | $2.5 \times 10^6$ | G4 creatinine | 2 | Required dialysis |
| 1010007 | $28 \times 10^6$ | G4 somnolence | 1 | Required intubation |
| 1010008 | $30 \times 10^6$ | G4 somnolence | 1 | Required intubation |
| 1010009 | $5 \times 10^6$ | G3 confusion/ aphasia G3 cranial nerve VII neuropathy | 2 | |
| 1010010 | $4 \times 10^6$ | G3 intermittent confusion/aphasia | 2 | |

TABLE 5-continued

Dose-Limiting Toxicities.

| Subject No. | Anti-CD19 CAR+ T cells/kg | Dose-Limiting Toxicities (DLT) | Group | Comment |
|---|---|---|---|---|
| 1010014 | $2.5 \times 10^6$ | G3 hypoxia G4 hypotension G3 creatinine G4 somnolence/ intermittent confusion | 2 | Required intubation |
| 1010015 | $2.5 \times 10^6$ | G4 myoclonus G4 expressive aphasia | 2 | Required intubation |
| 1010021 | $1 \times 10^6$ | G4 aphasia G3 motor neuropathy | 2 | |

Neurologic Adverse Events

Neurologic adverse events were observed in all three groups, predominantly aphasia/dysphasia, confusion, motor neuropathy and somnolence. Thirteen subjects (41%) had severe ≥grade 3 neurotoxicity, and 11 subjects (34%) experienced a serious event.

The subject who died with a neurotoxicity had an event of CNS cerebrovascular ischemia in the context of viral influenza A infection. This was deemed unrelated to the anti-CD19 CAR+ T cells by the investigator.

Five subjects (16%) with neurotoxicity events required mechanical ventilation for airway protection for neurological adverse events; all of these subjects were in Groups 1 and 2. There have been no subjects intubated in Group 3.

Neurologic adverse events had a median onset of 6 days ranging between days 2 and 17 post anti-CD19 CAR+ T cell infusion, with the exception of grade 4 myelitis which occurred in 1 subject and had an onset at day 110 post anti-CD19 CAR+ T cell infusion. Given the time of onset, presentation and brain MRI findings, this event was considered by the investigator to be related to fludarabine and not attributed to the anti-CD19 CAR+ T cells. The median time to resolution of the neurological adverse event to grade 1 or better was 14 days post infusion.

Deaths

Two subjects died within 30 days of chemotherapy and anti-CD19 CAR+ T cell infusion. Subject 2 died 18 days after investigational treatment due to a cerebral infarction concurrent with viral pneumonia, influenza A infection, *E coli* infection, dyspnea, and hypoxia. Subject 11 had PMBCL, with extensive fibrotic mediastinal lymphoma involvement, died 16 days after investigational treatment. No cause of death determined on autopsy and the autopsy report concluded likely cause of death was cardiac arrhythmia given the mediastinal involvement of PMBCL. Neither event was deemed related to anti-CD19 CAR+ T cells by the investigator.

Example 2

Select patients were administered a conditioning chemotherapy comprising cyclophosphamide 300 mg/m²/day and Fludarabine 30 mg/m²/day. The conditioning chemotherapy was administered for three days from day −5 to day −3. On day 0, a first subset of the patients (patients 22-28) (Table 6) received 10 day-manufacturing, fresh anti-CD19 CAR+ T cells, and a second subset of the patients (patients 29-32) received 6 day-manufacturing, cryopreserved anti-CD19 CAR+ T cells.

Patient sera was tested by luminex using Millipore HCD8MAG15K17PMX kit (T1, T2, immune modulating cytokines, chemokines, immune effectors). The levels of interleukin 15 (IL-15), monocyte chemotactic protein 1 (MCP-1), gamma-induced protein 10 (IP-10), placental growth factor (PLGF), soluble intercellular adhesion molecule 1 (sICAM-1), C-reactive protein (CRP), vascular endothelial growth factor D (VEGF-D), macrophage inflammatory protein 1β (MIP-1β) were measured before and after conditioning.

TABLE 6

Condition and Outcome Data for Patients 22-28.

| Patient | Condition | Outcome |
|---|---|---|
| 22 | DLBCL | PR |
| 23 | FL | PR |
| 24 | DLBCL | PR |
| 25 | DLBCL | PR |
| 26 | DLBCL | PD |
| 27 | DLBCL | CR |
| 28 | DLBCL | PD |

DLBCL = Diffuse Large B Cell Lymphoma;
FL = Follicular Lymphoma;
PR = Partial Response;
CR = Complete Response;
PD = Progressive Disease Of patients 22-28, patients 22-25 and 27 showed at least a partial response and patients 26 and 28 showed progressive disease following treatment. For patients 22-26, the levels of IL-15, MCP-1, and PLGF showed at least some increase in patient sera (FIGS. 4A, 4B, and 4D), while the levels of IP-10, sICAM-1, CRP, VEGF-D, and MIP-10 increased in some patients and remained stable or decreased in others (FIGS. 4C and 4E-4H). Only IL-15 was measured for patients 27 and 28 (FIG. 4A).

Some differences in marker levels were observed between responding patients, having either a partial or complete response, and non-responding patients, having progressive disease. IL-15 levels increased by an average of about 35-Fold in responding patients, ranging from about 10-fold to about 55-fold, relative to baseline, while the non-responding patients each had a less than about 10-fold increase in IL-15 levels (FIG. 5A). MCP-1 levels in responders increased by an average of about 5 fold, ranging from about 2 fold to about 7 fold, while the non-responder (patient 26) had a less than 4-fold increase in the level of MCP-1 (FIG. 5B). IP-10 levels in responders increased by an average of about 3.5 fold, ranging from about 2 fold to about 7 fold, while the non-responder had essentially no change in the level of serum IP-10 (FIG. 5C). PLGF levels in responders increased by an average of about 30 fold, ranging from a slight increase of about 2 fold or less to an increase of about over 100 fold, while the non-responder had only a slight increase in the level of serum PLGF (FIG. 5D). sICAM-1 levels in responders increased by an average of about 3 fold, ranging from essentially no change to an increase of about 4.5 fold, while the non-responder had essentially no change in the level of serum sICAM-1 (FIG. 5E). CRP levels in responders increased by an average of about 10 fold, ranging from essentially no change to an increase of about 25 fold, while the non-responder had essentially no change in the level of serum CRP (FIG. 5F). VEGF-D levels in responders increased by an average of about 3 fold, ranging from essentially no change to an increase of about 6 fold, while the non-responder had essentially no change in the level of serum VEGF-D (FIG. 5G). MIP-1β levels in responders increased by an average of about 1.5 fold, ranging from essentially no change to an increase of about 3 fold, while the level of serum MIP-1β decreased by about 50% in the non-responder (FIG. 5H).

Patients 30-33 were dosed with 6 day-manufacturing, cryopreserved cells, and the levels of various cytokines, chemokines, effectors, markers of inflammation, and adhesion molecules, including granulocyte macrophage colony-stimulating factor (GM-CSF), interferon γ (IFNγ or IFNG), interleukin 10 (IL-10), IL-15, interleukin 2 (IL-2), interleukin 5 (IL-5), interleukin 6 (IL-6), interleukin 8 (IL-8), IP-10, MCP-1, MIP-1β, serum granzyme A (GRNZA), serum granzyme B (GRNZB), PLGF, CRP, monocyte chemotactic protein 4 (MCP-4), interleukin 16 (IL-16), thymus and activation regulated chemokine (TARC), Eotaxin-3, sICAM-1, soluble vascular adhesion molecule 1 (sVCAM-1), and serum amyloid A (SAA), were measured on selected days from day −6 through day 18 (FIGS. 6A-6V).

Example 3

To improve the depth and duration of lymphocyte depletion observed in group 3 of Example 1, the conditioning chemotherapy dose in cohort A1 will be increased to cyclophosphamide at 500 mg/m² and fludarabine at 30 mg/m² both given for 3 concurrent days with the target dose of 2×10⁶ anti-CD19 CAR+ T cells/kg. The cyclophosphamide dose used in this regimen (Cohort A1) is approximately 38% lower than that used in the Group 2 cyclophosphamide 30 mg/kg conditioning regimen from Example 1 (incidence of dose limiting toxicity (DLT) 29%), with the same lower dose of fludarabine dose as Group 3 of Example 1.

Evaluation of higher conditioning chemotherapy doses and/or varying anti-CD19 CAR+ T cell doses would proceed based on the incidence of DLT and evaluation of benefit-risk. The CAR vector construct is identical to the construct described in Example 1. This example describes a clinical trial designed to test the safety and efficacy of anti-CD19 CAR+ T cells generated by a rapid, closed, and bead-less process. Closing the process retains the characteristics of the T cell product.

Study Design

A phase 1/2 multicenter, open-label study will be performed evaluating the safety and efficacy of KTE-C19 in subjects with refractory NHL. The study will be separated into two distinct phases designated as phase 1 and phase 2.

During phase 1, approximately 6 to 24 subjects with DLBCL, PMBCL or TFL will be enrolled to evaluate the safety of KTE-C19 regimens. A safety review team (SRT), internal to the study sponsor, will review the safety data and make recommendations on further study conduct of phase 1 and progression to phase 2 as depicted in FIG. 3.

During phase 2, subjects will enroll into two separate cohorts designated as cohort 1 and cohort 2. Cohort 1 will enroll adult subjects with refractory DLBCL, and cohort 2 will enroll adult subjects with refractory PMBCL and TFL. TFL is defined as subjects who received prior chemotherapy for follicular lymphoma.

Independent of the phase of the study each subject will follow the same study treatment schedule and procedural requirements. Each subject will proceed through the following study periods: screening/leukapheresis period; conditioning chemotherapy period; investigational product (IP) treatment period; post treatment assessment period Long-term follow-up period Study Duration For an individual subject, the length of participation includes an up to 28-day screening period, a 5-7 day conditioning chemotherapy treatment period, a KTE-C19 treatment period (which includes a 7-day in-hospital recovery period), a post treatment assessment period, and a long term follow-up period (survival surveillance for up to 15 years).

Subjects will be followed for all adverse events for 3 months after treatment. After 3 months, subjects will be monitored for targeted adverse events/serious adverse events (e.g., hematological, neurological, second malignancies, infections or autoimmune disorders) and presence of replication competent retrovirus (RCR) in subjects blood at intervals outlined in the schedule of assessments (SOA). The need for prolonged follow-up is based on the potential persistence of gene transfer vectors in treated subjects.

Completion of the study is defined as the time at which the last subject completes the long term follow-up period visit, is considered lost to follow-up, withdraws consent, or dies. The primary analyses will be conducted when all subjects in cohort 1 of phase 2 and the overall study population, respectively have completed the 6 month disease response assessment, are lost to follow-up, withdraw from the study, or die, whichever occurs first.

Subject Eligibility

The inclusion criteria for subjects include:

a) Histologically confirmed aggressive B cell NHL, including the following types defined by WHO 2008: DLBCL not otherwise specified, T cell/histiocyte rich large B cell lymphoma, DLBCL associated with chronic inflammation, Epstein-Barr virus (EBV)+ DLBCL of the elderly; primary mediastinal (thymic) large B cell lymphoma; or transformation of follicular lymphoma to DLBCL;

b) Chemotherapy-refractory disease, defined as one or more of stable disease (duration of stable disease must be ≤12 months) or progressive disease as best response to most recent chemotherapy containing regimen; and disease progression or recurrence ≤12 months of prior autologous SCT;

c) subjects must have received adequate prior therapy including at a minimum anti-CD20 monoclonal antibody unless investigator determines that tumor is CD20 negative and an anthracycline containing chemotherapy regimen;

d) Subjects with transformed FL must have received prior chemotherapy for follicular lymphoma and subsequently have chemorefractory disease after transformation to DLBCL;

e) At least 1 measurable lesion according to the revised IWG Response Criteria for Malignant Lymphoma; lesions that have been previously irradiated will be considered measurable only if progression has been documented following completion of radiation therapy;

f) MRI of the brain showing no evidence of central nervous system lymphoma;

g) Greater than or equal to 2 weeks must have elapsed since any prior radiation therapy or systemic therapy at the time the subject is planned for leukapheresis;

h) Toxicities due to prior therapy must be stable or recovered to ≤Grade 1 (except for clinically non-significant toxicities such as alopecia);

i) Subjects must be age 18 or older;

j) Eastern cooperative oncology group (ECOG) performance status of 0 or 1 k) Subjects must have the following laboratory values: i) ANC≥1000/uL; ii) Platelet count≥50,000/uL; iii) Adequate renal, hepatic, and cardiac function defined as serum creatinine≤1.5 mg/dL, serum ALT/AST≤2.5 ULN, and total bilirubin≤1.5 mg/dl, except in subjects with Gilbert's syndrome; and iv) Cardiac ejection fraction≥50% and no evidence of pericardial effusion as determined by an ECHO; and l) Females of childbearing potential must have a negative serum or urine pregnancy test.

The exclusion criteria for subjects includes:

a) History of malignancy other than nonmelanoma skin cancer or carcinoma in situ (e.g., cervix, bladder, breast) or follicular lymphoma unless disease free for at least 3 years;

b) History of Richter's transformation of CLL;

c) Autologous stem cell transplant within 6 weeks of informed consent;

d) History of allogeneic stem cell transplantation;

e) Prior CD19 targeted therapy with the exception of subjects who received KTE-C19 in this study and are eligible for re-treatment;

f) Prior chimeric antigen receptor therapy or other genetically modified T cell therapy;

g) History of severe, immediate hypersensitivity reaction attributed to aminoglycosides;

h) Clinically significant active infection (e.g., simple UTI, bacterial pharyngitis allowed) or currently receiving IV antibiotics or have received IV antibiotics within 7 days prior to enrollment (Prophylaxis antibiotics, antivirals and antifungals are permitted);

i) Known history of infection with HIV or hepatitis B (HBsAg positive) or hepatitis C virus (anti-HCV positive);

j) Subjects with detectable cerebrospinal fluid malignant cells, or brain metastases, or with a history of cerebrospinal fluid malignant cells or brain metastases;

k) History of a seizure disorder, cerebrovascular ischemia/hemorrhage, dementia, cerebellar disease, or any autoimmune disease with CNS involvement;

l) Subjects with cardiac atrial or cardiac ventricular lymphoma involvement;

m) Requirement for urgent therapy due to tumor mass effects such as bowel obstruction or blood vessel compression;

n) Primary immunodeficiency;

o) Any medical condition likely to interfere with assessment of safety or efficacy of study treatment;

p) Current or expected need for systemic corticosteroid therapy; topical and inhaled corticosteroids in standard doses and physiologic replacement for subjects with adrenal insufficiency are allowed; doses of corticosteroids of greater than or equal to 5 mg/day of prednisone or equivalent doses of other corticosteroids are not allowed;

q) History of severe immediate hypersensitivity reaction to any of the agents used in this study;

r) Live vaccine ≤6 weeks prior to start of conditioning regimen;

s) Women of child-bearing potential who are pregnant or breastfeeding, because of the potentially dangerous effects of the preparative chemotherapy on the fetus or infant; females who have undergone surgical sterilization or who have been postmenopausal for at least 2 years are not considered to be of childbearing potential;

t) Subjects of both genders who are not willing to practice birth control from the time of consent through 6 months after the completion of KTE-C19; and u) In the investigators judgment, the subject is unlikely to complete all protocol-required study visits or procedures, including follow-up visits, or comply with the study requirements for participation.

In addition, biomarker analysis will be performed on blood and tumor samples to evaluate predictive and pharmacodynamic markers for KTE-C19. Prognostic markers in aggressive NHL may also be evaluated. Baseline leukapheresis and final KTE-C19 samples will be banked and may be analyzed by immunophenotyping and/or gene expression profiling. Remaining samples may be stored for future exploratory analysis of DNA, RNA, or protein markers. Archived tumor tissue will be collected for central path review. Additional analysis may include CD19 expression, gene expression profiling, and analysis of DNA alterations. Remaining tumor samples may be stored for future exploratory analysis of DNA, RNA, or protein markers.

Protocol Treatment

Schedule

Leukocytes will be obtained from subjects by leukapheresis (12-15 liter apheresis with a goal to target approximately $5-10 \times 10^9$ mononuclear cells for the manufacturing of KTE-C19. Each subject's leukapheresed product will be processed to enrich for the T cells containing PBMC fraction. T cells are then stimulated to expand and transduced with a retroviral vector to introduce the CAR gene. The T cells are then expanded and cryopreserved to generate the investigational product. Following completion of each subject's conditioning chemotherapy regimen, subjects will receive their respective KTE-C19 infusion.

Study Treatment

Subjects will receive a non-myeloablative conditioning regimen consisting of cyclophosphamide and fludarabine in order to induce lymphocyte depletion and create an optimal environment for expansion of KTE-C19 in vivo. Subjects will initiate conditioning chemotherapy with cyclophosphamide and fludarabine beginning on Day −5 (or Day −7 for cohort B) through Day −1. The 5-day conditioning chemotherapy regimen will be administered in an outpatient setting. The 7-day conditioning chemotherapy regimen may be administered as an outpatient or inpatient regimen per investigator's discretion.

Phase 1:

In Cohorts A1 and A2, subjects will receive the following 5-day conditioning chemotherapy regimen: IV hydration with 1 L of 0.9% NaCl saline solution given prior to cyclophosphamide on the day of infusion; followed by Cyclophosphamide 500 mg/m² IV over 60 minutes on Day −5, Day −4, and Day −3; followed by Fludarabine 30 mg/m² IV over 30 minutes on Day −5, Day −4, and Day −3; followed by an additional 1 L of 0.9% NaCl saline solution at the completion of the fludarabine infusion (FIG. 3). In certain cases, mesna (sodium 2-mercaptoethanesulfonate) can be added per institutional guidelines.

In Cohort A3, subjects will receive the following 5-day chemotherapy regimen: IV hydration with 1 L of 0.9% NaCl saline solution given prior to cyclophosphamide on the day of infusion; followed by Cyclophosphamide 300 mg/m² IV over 60 minutes on Day −5, Day −4, and Day −3; followed by Fludarabine 30 mg/m² IV over 30 minutes on Day −5, Day −4, and Day −3; followed by an additional 1 L of 0.9% NaCl saline solution at the completion of the fludarabine infusion. In certain cases, mesna may be added per institutional guidelines For subjects enrolled into Cohorts A1, A2, or A3, Day −2 and Day −1 will be rest days before KTE-C19 infusion on Day 0.

In Cohorts B1 and B2, subjects will receive the following 7-day chemotherapy regimen: IV hydration with 0.9% NaCl saline solution, recommended at 2.6 ml/kg/hr (maximum 200 ml/hr), administered as a continuous infusion starting 11 hours pre-cyclophosphamide infusion and continue hydration until 24 hours after last cyclophosphamide infusion; Cyclophosphamide 30 mg/kg (1110 mg/m²) IV administered on Day −7 and −6, infused over 120 minutes; followed by Fludarabine 25 mg/m² IV administered on Day −5, Day −4, Day −3, Day −2 and Day −1, infused over 30 minutes. In certain cases, mesna may be added per institutional guidelines.

For subjects enrolled into Cohort B1 or B2, there will be no rest days between the last day of chemotherapy (Day −1) and the KTE-C19 infusion on Day 0.

For KTE-C19, subjects in Cohorts A1, A3, or B1 will receive KTE-C19 treatment consisting of a single infusion of CAR transduced autologous T cells administered intravenously at a target dose of $2\times10^6$ anti-CD19 CAR+ T cells/kg (±20%; $1.6\times10^6$ anti-CD19 CAR+ T cells/kg to $2.4\times10^6$ anti-CD19 CAR+ T cells/kg). A minimum dose of $1\times10^6$ anti-CD19 CAR+ T cells/kg may be administered. For subjects weighing greater than 100 kg, a maximum flat dose of $2\times10^8$ anti-CD19 CAR+ T cells will be administered.

Subjects in Cohorts A2 or B2 will receive KTE-C19 treatment consisting of a single infusion of CAR transduced autologous T cells administered intravenously at a target dose of $1\times10^6$ anti-CD19 CAR+ T cells/kg (±20%; $0.8\times10^6$ anti-CD19 CAR+ T cells/kg to $1.2\times10^6$ anti-CD19 CAR+ T cells/kg). A minimum dose of $0.5\times10^6$ anti-CD19 CAR+ T cells/kg may be administered. For subjects weighing greater than 100 kg, a maximum flat dose of either $1\times10^8$ anti-CD19 CAR+ T cells will be administered.

Phase 2:

A KTE-C19 regimen determined by the SRT to be safe in phase 1 will be carried forward into the phase 2 portion of the study.

Retreatment

Subjects who achieved a PR or CR can receive a second course of conditioning chemotherapy and KTE-C19 if their disease subsequently progresses (and the relapse is not known to be CD19-malignant cells). To be eligible for a second course of treatment, subjects should be re-evaluated and continue to meet the original study eligibility criteria, with the exception of exclusion criteria related to prior CAR therapy, and should not have received subsequent chemotherapy for the treatment of lymphoma. Furthermore, any toxicity related to fludarabine or cyclophosphamide should be stable and resolved to less than grade 1 prior to retreatment with the exception of alopecia. A maximum of 1 retreatment course may occur per subject. Subjects enrolled in phase 2 will receive the same KTE-C19 regimen. Subjects enrolled in phase 1 will receive the KTE-C19 regimen selected for phase 2. If the phase 2 regimen has not yet been selected, subjects will receive the last KTE-C19 regimen that was determined safe by the SRT.

Subjects who experience a DLT in phase 1 or a comparable toxicity in phase 2 will not be eligible for retreatment. Furthermore, if a subject has a known neutralizing antibody, the subject will not be eligible for retreatment. However, if a non-neutralizing HAMA or HABA antibody develops, subjects may be retreated if they meet the eligibility criteria.

Post-Treatment Assessment

After completing KTE-C19 infusion and being discharged from the hospital (typically on Day 8), all subjects will be followed in the post-treatment assessment period. Counting from day 0 (KTE-C19 infusion), subjects will return to the clinic at week 2, week 4 (±3 days), month 2 (±1 week), and month 3 (±1 week). Assessment can include MMSE (mini mental status exam); PET-CT for disease assessment; physical exam and vital signs; labs, including Chemistry Panel, CBC with differential, β-HCG pregnancy test (serum or urine) on all women of child-bearing potential, anti-KTE-C19 antibodies, lymphocyte subsets, cytokine levels, anti-CD19 CAR+ T cells, and replication-competent retrovirus (RCR) analysis; adverse/serious adverse event reporting; concomitant medications documentation; and collection of fresh tumor sample(s) for subjects who signed the optional portion of the consent.

The presence, expansion, persistence, and immunophenotype of transduced anti-CD19 CAR+ T cells will be monitored in the blood primarily by PCR analysis, complemented by flow cytometry. Levels of serum cytokines will also be evaluated in the blood. The following cytokines may be included in the panel: pro-inflammatory and immune modulating cytokines IL-6, TNFα, IL-8, IL-1, IL-2, GM-CSF, IL 15, IL-17a, IFNγ, IL-12p40/p70; immune effector molecules Granzyme A, B, Perforin, sFasL; correlates of acute phase response CRP, SAA and Chemokines MIP-1α, MIP-3α, IP-10, Eotaxin, MCP-4. As KTE-C19 comprises retroviral vector transduced T cells, the presence of replication-competent-retrovirus (RCR) in the blood of treated patients will also be monitored.

If the subject is eligible for retreatment with KTE-C19, the last scan prior to retreatment will be considered the baseline for the purpose of evaluating the response to retreatment.

At any time during the post-treatment assessment period, if a subject did not respond to treatment (i.e., CR or PR) or progresses following a response, the subject will proceed directly to the Month 3 visit and be followed for disease outcomes in the long term follow-up period.

All subjects will be followed in the long-term follow-up period for survival and disease status, if applicable. Subjects will begin the long-term follow-up period after they have completed the Month 3 visit of the post-treatment assessment period (whether they have responded to treatment or gone straight to the month-3 visit due to disease progression). Counting from day 0 (KTE-C19 infusion), subjects will return to the clinic every 3 months (±2 weeks) through Month 18; every 6 months (±1 month) between Month 24-Month 60; and, beginning with year 6, Month 72 (±3 months), subjects will return to the clinic 1 time annually up to 15 years. The following procedure will be completed at this visit: physical exam; PET-CT Scan; disease assessment; labs, including CBC with differential, anti-KTE-C19 antibodies, lymphocyte subsets, anti-CD19 CAR+T cells, and RCR analysis; targeted adverse/serious adverse event reporting (for 24 months or until disease progression whichever occurs first), including neurological, hematological, infections, autoimmune disorders, and secondary malignancies until disease progression; targeted concomitant medication documentation (for two years after disease progression), including gammaglobulin, immunosuppressive drugs, anti-infective, vaccinations, and any therapy for the treatment of progressive diseases.

Evaluation will include baseline PET-CT scans of the neck, chest, abdomen and pelvis, along with the appropriate imaging of all other sites of disease. Subjects will have their first post KTE-C19 infusion planned PET-CT tumor assessment 4 weeks following the KTE-C19 infusion and at regular intervals as described above.

A bone marrow aspirate and biopsy will be performed in subjects who are being assessed for CR. Per the revised IWG Response Criteria for Malignant Lymphoma, a bone marrow aspirate and biopsy should be performed only when the subject had bone marrow involvement with lymphoma prior to therapy or if new abnormalities in the peripheral blood counts or blood smear cause clinical suspicion of bone marrow involvement with lymphoma after treatment. The bone marrow aspirate and biopsy must show no evidence of disease by morphology, or if indeterminate by morphology, it must be negative by immunohistochemistry to assign a CR to treatment.

Study Endpoints

Primary

The primary endpoint for Phase 1 is incidence of adverse events defined as dose-limiting toxicities (DLT). The primary endpoint for Phase 2 is the Objective Response Rate (ORR), defined as the incidence of either a complete response or a partial response by the revised IWG Response Criteria for Malignant Lymphoma as determined by the study investigators. All subjects that do not meet the criteria for an objective response by the analysis cutoff date will be considered non-responders.

Secondary

Objective response rate among subjects in phase 1 will be summarized. Objective response rate among subjects in phase 2 will be determined per IRRC, which is defined as the incidence of either a complete response or a partial response by the revised IWG Response Criteria for Malignant Lymphoma as determined by the IRRC. All subjects that do not meet the criteria for an objective response by the analysis data cutoff date will be considered non-responders. The duration of response (DOR) for subjects who experience an objective response defined as the date of their first objective response which is subsequently confirmed to disease progression per the revised IWG Response Criteria for Malignant Lymphoma or death, regardless of cause. Subjects not meeting the criteria for progression or death by the analysis data cutoff date will be censored at their last evaluable disease assessment date and their response will be noted as ongoing.

Dose-Limiting Toxicity (DLT)

Dose-limiting toxicity is defined as the following KTE-C19-related events with onset within the first 30 days following KTE-C19 infusion:

a) Grade 4 neutropenia lasting longer than 21 days from the day of cell transfer b) Grade 4 thrombocytopenia lasting longer than 35 days from the day of cell transfer c) Any KTE-C19-related adverse event requiring intubation, including grade 4 confusion requiring intubation for airway protection is considered to be a DLT.

d) All other grade 3 toxicities lasting more than 3 days and all grade 4 toxicities, with the exception of the following conditions which are not considered DLT's: i) Aphasia/dysphasia or confusion/cognitive disturbance which resolves to grade 1 or less within 2 weeks and to baseline within 4 weeks; ii) Fever grade 3; iii) Myelosuppression (includes bleeding in the setting of platelet count less than 50×109/L and documented bacterial infections in the setting of neutropenia), defined as lymphopenia, decreased hemoglobin, neutropenia and thrombocytopenia unless neutropenia and thrombocytopenia meet the DLT definition described above; iv) Immediate hypersensitivity reactions occurring within 2 hours of cell infusion (related to cell infusion) that are reversible to a grade 2 or less within 24 hours of cell administration with standard therapy; and v) Hypogammaglobulinemia grade 3 or 4.

CRS will be graded according to a revised grading system (Lee 2014). Adverse events attributed to CRS will be mapped to the overall CRS grading assessment for the determination of DLT.

During phase 1, approximately 6-24 subjects with DLBCL, PMBCL or TFL will be enrolled to evaluate the safety of KTE-C19 regimens. Subjects in each cohort will be evaluated for DLTs within the first 30 days following the completion of their respective KTE-C19 infusion. If the subject incidence of DLT is ≤1 of 6 subjects, cohort B1 may be explored or the study may proceed to phase 2 of the trial. This decision will be based on overall benefit/risk and available biomarker data.

However, if 2 of the 6 enrolled subjects present with a protocol defined DLT during phase 1, the SRT may recommend enrolling 2 additional sets of 3 subjects (up to 12 subjects in total) at the same dose that was administered in the first 6 subjects. In this scenario, progression to an additional cohort or to phase 2 of the study will proceed if ≤2 of the first 9 or if ≤3 of the 12 subjects present with a DLT.

If the subject incidence of DLT is >2/6, >3/9, or >4/12 subjects, other KTE-C19 regimens may be explored in an additional 6-12 subjects (FIG. 3). The same DLT rules apply as above.

Example 4

T cell products were generated by transduction of autologous lymphocytes with a g-murine retrovirus carrying an anti-CD19 CAR construct gene, followed by expansion to achieve desired cell dose. Anti-CD19 CAR+ T cell product characteristics were evaluated at time of harvest, or after co-culture with CD19+ cells, by flow cytometry and multiplex cytokine analysis of co-culture supernatants. CAR+ T cell co-culture for product characterization was performed with K562-CD19 cells or K562-NGFR control cells, at an effector to target ratio of 1:1. Standard incubation time was 18 hours. Patients with relapsed/refractory B cell malignancies were conditioned with cyclophosphamide and fludarabine, then dosed with anti-CD19 CAR+ T cells.

Cytokine and chemokine levels were measured using EMDmillipore Luminex® xMAP® multiplex assays. Data acquisition and analysis were performed using a Luminex 200™ instrument and xPONENT® 3.1 data analysis software. For IL-7, a human IL-7 Quantikine HS ELISA Kit (HS750) was used with samples run neat per manufacturer's guidelines. The frequency of CAR T cells in circulation was measured by a quantitative PCR analysis. Patients were administered a preconditioning regimen comprising of 300 mg/m$^2$ cyclophosphamide on days −5 and −4, and 30 mg/m$^2$ fludarabine on days −5, −4, and −3. Patient sera was collected prior to administration of cyclophosphamide and fludarabine between days −12 and −5 ("pre"), immediately before administration of CAR+ T cells on day 0 ("post") and on select days following CAR+ T cell administration up to day 18. The serum concentrations of GF-CSF, IL-2, MCP-1, IL-6, IL-10, MCP-4, CRP, IFN gamma, Granzyme A, IL-15, IL-5, Granzyme B, IL-8, IP-10, MIP-1b, PLGF, IL-16, TARC, Eotaxin-3, sICAM-1, sVCAM-1, and SAA were measured pre- and post-conditioning and on select days after administration of CAR+ T cells, as shown in FIG. 6. The concentration of certain cytokines were found to increase in patient sera post-conditioning with 300 mg/m$^2$ cyclophosphamide and 30 mg/m$^2$ fludarabine (FIGS. 7A-7I and 18A-18E). In particular, the concentrations of IL-15, IL-7, PLGF, CRP, and MCP-1 significantly increased following conditioning with cyclophosphamide and fludarabine (FIGS. 7A-7D, 7G, 18A, and 18C-18E). Increases were also observed in the concentrations of IL-5, IL-10, IP-10, and s-ICAM1 (FIGS. 7E-7F, 7H-7I, and 18B). Conversely, perforin was found to decrease after conditioning with cyclophosphamide and fludarabine (FIG. 18F). The serum concentrations of various other analytes were observed to increase or decrease following preconditioning, as shown in FIG. 18G. Additional patients were treated, and the results set forth in FIGS. 11-17. In addition, increased serum levels of IL-15 (FIG. 19A) and IP-10 (FIG. 19B) and decreased serum levels of Perforin (FIG. 19C) following preconditioning were found to significantly correlate with a positive objective response in patients treated with CAR T cells.

Post-CAR+ T cell infusion peripheral blood lymphocytes (PBLs) and sera were evaluated by flow cytometry and multiplex cytokine analysis, respectively. Pre-infusion anti-CD19 CAR+ T cell cytokine production was compared to a K562-NGFR negative control (FIG. 8). The concentration of T1, T2, and immune homeostatic cytokines GM-CSF, IL-2, IFN gamma, IL-5, IL-4, and IL-13, and pro-inflammatory cytokines and chemokines TNF alpha, IL-6, Granzyme B, MIP-1b (beta), MIP-1a (alpha), and sCD137 were higher in anti-CD19 CAR+ T cell samples relative to negative controls (FIGS. 8A-8L). In addition, engagement of the target antigen by pre-infusion product T cells lead to upregulation of receptors that can modulate their activity, such as CD107a (alpha), 401BB, and PD-1 (FIGS. 9A-9C).

Multicolor flow cytometry was carried out on a BD FACSCanto II utilizing FlowJo software for data acquisition and analysis. A shorter manufacturing process yielded CAR+ T cell products with a higher representation of CD4+, naïve, and central memory T cells (FIG. 10). Post-infusion, CAR+ T cells show a diversified subset composition comprising mainly differentiated T cells, and some central memory or naïve T cells (FIG. 10).

Anti-CD19 CD28zeta CAR+ T cells are clinically effective and induce durable responses in both lymphoma and leukemia. Durable clinical responses can occur without long lasting CAR+ T cells in circulation, allowing normal B cell recovery. Conditioning with cyclophosphamide and fludarabine modifies the immune environment through induction of molecules that can favor the homeostatic expansion, activation and trafficking of T cells. CAR+ T cell treatment results in rapid elevation and subsequent resolution of circulating cytokines and chemokines within three weeks after treatment.

Example 5

A study will be performed to test the safety and efficacy of treating subjects with a non-myeloablative conditioning regimen consisting of doses of cyclophosphamide greater than or equal to 300 mg/m$^2$ and fludarabine greater than or equal to 30 mg/m$^2$. The doses of these conditioning chemotherapy agents will be used to further induce lymphocyte depletion and create a more optimal environment for expansion of KTE-C19 in vivo.

Enrolled subjects will undergo leukopheresis to obtain PBMCs for the production of anti-CD19 CAR+ T cells. The subjects will then receive a conditioning chemotherapy comprising 500 mg/m$^2$/day cyclophosphamide and 60 mg/m$^2$/day fludarabine administered on day −5 to day −3. The subjects will then receive a dose of anti-CD19 CAR+ T cells/kg by IV on day 0. As a starting dose, subjects may receive 2×10$^6$ anti-CD19 CAR+ T cells/kg (±20%), which can then be increased or decrease depending on subject responsiveness.

Following conditioning chemotherapy and administration of anti-CD19 CAR+ T cells, the subjects will be monitored for adverse effects, serum cytokine levels, T cell counts, and disease response. The serum levels of various cytokines, chemokines, effectors, markers of inflammation, and adhesion molecules, including, but not limited to, IL-2, IL-4, IL-5, IL-6, IL-7, IL-8, IL-10, IL-15, IL-16, IL-21, MCP-1, IP-10, PLGF, sICAM-1, CRP, VEGF, VEGF-C, VEGF-D, sVCAM-1, MIP-1β, FGF2, IL-1b, Eotaxin, GM-CSF, IFN gamma, IL-12p40, MDC, IL-12p70, IL-13, IL-17A, MIP-1a, TNFa, TNFb, granzyme A, granzyme B, perforin, SAA, MCP-4, and TARC, will be measured before and after conditioning to determine the effect of the conditioning chemotherapy. Serum will be collected before or after administration of each of cyclophosphamide, fludarabine, and anti-CD19 CAR+ T cells, and all levels will be compared to the levels prior to conditioning chemotherapy. Disease responsiveness will be compared to each patient's the cytokine profile following conditioning to identify any correlations between disease responsiveness and the levels of one or more cytokine following conditioning.

The occurrence of adverse effects will be closely monitored to determine the maximum tolerable dose of cyclophosphamide and fludarabine. Adverse effects may be medically controlled as necessary. The doses of one or both of cyclophosphamide and fludarabine may be increased or decreased to improve clinical efficacy and limit adverse effects. Any subjects that show initial partial response followed by disease progression may receive a second treatment at the same or a different level of cyclophosphamide and/or fludarabine. Throughout this application, various publications are referenced in parentheses by author name and date, or by Patent No. or Patent Publication No. Full citations for these publications may be found at the end of the specification immediately preceding the claims. The disclosures of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention. All of the various aspects, embodiments, and options described herein can be combined in any and all variations.

Example 6

A study will be performed to predict the likelihood of a patient's response to T cell therapy based on cytokine responsiveness to preconditioning with one or more preconditioning agents. Patients suffering from a cancer that is suitable for T cell therapy will be selected for this study.

Patient blood will be collected prior to any interventions. Patients will then be preconditioned by administering to the patient one or more preconditioning agents according to the present invention. For example, patients may be treated with 300 or 500 mg/m$^2$/day of cyclophosphamide for two or three days and 30 or 60 mg/m$^2$/day of fludarabine for three, four, or five days prior to a T cell therapy. Patient blood will then be collected again following preconditioning and immediately prior to, e.g., on the same day as, administering the T cell therapy. Patients will then be administered a T cell therapy and monitored for disease responsiveness, e.g., progressive disease, partial response, or complete response.

Blood collected before and after preconditioning will be analyzed for sera levels of various cytokines, including, but not limited to, IL-15, IL-7, and at least one additional cytokine selected from the group consisting of MCP-1, CRP, PLGF, IP-10, and any combination thereof. The fold change in each cytokine will be recorded for each patient and compared with the overall disease responsiveness. Correlative studies will be conducted to determine if the increase or decrease of any one or more cytokines is predictive of overall disease responsiveness.

All publications, patents, and patent applications mentioned in this specification are herein incorporated by reference to the same extent as if each individual publication, patent, or patent application was specifically and individually indicated to be incorporated by reference. However, the citation of a reference herein should not be construed as an acknowledgement that such reference is prior art to the present invention.

Having generally described this invention, a further understanding can be obtained by reference to the examples provided herein. These examples are for purposes of illustration only and are not intended to be limiting.

What is claimed is:

1. A method for treating a lymphoma in a patient suitable for chimeric antigen receptor (CAR) T cell therapy comprising:
   (i) administering to the patient one or more preconditioning agents that are capable of decreasing the serum level of Perforin and increasing a serum level of interleukin-15 ("IL-15"), interleukin-7 ("IL-7"), and of at least one additional cytokine selected from the group consisting of monocyte chemotactic protein 1 ("MCP-1"), C-reactive protein ("CRP"), placental growth factor ("PLGF"), interferon gamma-induced protein 10 ("IP-10"), and any combination thereof, wherein the preconditioning agents comprise cyclophosphamide and fludarabine;
   and (ii) administering a therapeutically effective amount of anti-CD19 CAR T cell therapy on day zero, wherein the patient has been determined to exhibit a decrease in the serum level of Perforin and an increased serum level of IL-15, IL-7, and the at least one additional cytokine, at day zero, prior to the administration of CAR T cell therapy and relative to their baseline serum levels, wherein the cytokine serum levels have been measured by an enzyme-linked immunosorbent assay (ELISA) or any method that detects the amount of protein in the serum for each cytokine and allows for their quantification, prior to the administration of the preconditioning agents.

2. The method for identifying a patient suitable for anti-CD19 CAR T cell therapy comprising (i) administering to the patient one or more preconditioning agents that are capable of decreasing the serum level of Perforin and increasing a serum level of IL-15, IL-7, and of at least one additional cytokine selected from the group consisting of MCP-1, CRP, PLGF, IP-10, and any combination thereof, wherein the preconditioning agents comprise cyclophosphamide and fludarabine; (ii) measuring the serum levels of Perforin, IL-15, IL-7, and of at least one additional cytokine selected from the group consisting of MCP-1, CRP, PLGF, IP-10, and any combination thereof, at baseline, which is prior to the administration of the preconditioning agent(s), and at day zero, which is after administration of the preconditioning agent(s) and prior to, but on the day of, administration of CAR T cell therapy; wherein the cytokine serum levels have been measured by an enzyme-linked immunosorbent assay (ELISA) or any method that detects the amount of protein in the serum for each cytokine and allows for their quantification; and wherein the patient is selected as suitable for anti-CD19 CAR T cell therapy when there is a decrease in the serum level of Perforin and an increase in the levels of the cytokines measured from the baseline to the day zero measurements; administering to the selected patient anti-CD19 CAR T cell therapy.

3. A method for decreasing the serum level of Perforin and increasing a serum level of IL-15, IL-7, and of at least one additional cytokine selected from the group consisting of MCP-1, CRP, PLGF, IP-10, and any combination thereof to pre-condition a patient in need of anti-CD19 CAR T cell therapy comprising administering to the patient one or more preconditioning agents, wherein the patient is treated with anti-CD19 CAR T cell therapy when exhibiting a decreased serum level of Perforin and an increased serum level of IL-15, IL-7, and of the at least one additional cytokine prior to, but on the day of administration of the therapy, relative to baseline levels prior to pre-conditioning, wherein the cytokine serum levels have been measured by an enzyme-linked immunosorbent assay (ELISA) or any method that detects the amount of protein in the serum for each cytokine and allows for their quantification; and wherein the preconditioning agents comprise cyclophosphamide and fludarabine.

4. The method of any one of claims 1, 2, and 3, wherein:
   a. the serum level of IL-7 in the patient is increased at least 6-fold, after the administration compared to the IL-7 serum level prior to the administration of the one or more preconditioning agents;
   b. the serum level of IL-15 in the patient is increased at least 18-fold after the administration compared to the IL-15 serum level prior to the administration of the one or more preconditioning agents;
   c. the serum level of MCP-1 in the patient is increased at least 2-fold after the administration compared to the MCP-1 serum level prior to the administration of the one or more preconditioning agents;
   d. the serum level of PLGF in the patient is increased at least 1.5-fold after the administration compared to the PLGF serum level prior to the administration of the one or more preconditioning agents;
   e. the serum level of CRP in the patient is increased at least 1.5-fold after the administration compared to the CRP serum level prior to the administration of the one or more preconditioning agents;
   f. the serum level of IP-10 in the patient is increased at least 2-fold after the administration compared to the IP-10 serum level prior to the administration of the one or more preconditioning agents; or
   g. any combination thereof.

5. The method of any one of claims 1, 2, and 3, wherein:
   (i) a dose of cyclophosphamide administered to the subject is about 300 mg/m$^2$/day to about 2000 mg/m$^2$/day;
   (ii) a dose of fludarabine administered to the subject is about 20 mg/m$^2$/day to about 900 mg/m$^2$/day; or
   (iii) both (i) and (ii).

6. The method of claim 5, wherein:
   (i) a dose of cyclophosphamide administered to the subject is about 350 mg/m$^2$/day, about 400 mg/m$^2$/day, about 450 mg/m$^2$/day, about 500 mg/m$^2$/day, about 550 mg/m$^2$/day, about 600 mg/m$^2$/day, about 650 mg/m$^2$/day, about 700 mg/m$^2$/day, about 800 mg/m$^2$/day, about 900 mg/m$^2$/day, or about 1000 mg/m$^2$/day;
   (ii) a dose of fludarabine administered to the subject is about 25 mg/m$^2$/day, about 30 mg/m$^2$/day, about 35 mg/m$^2$/day, about 40 mg/m$^2$/day, about 45 mg/m$^2$/day, about 50 mg/m$^2$/day, about 55 mg/m$^2$/day, about 60 mg/m$^2$/day, about 65 mg/m$^2$/day, about 70 mg/m$^2$/day, about 75 mg/m$^2$/day, about 80 mg/m$^2$/day, about 85 mg/m$^2$/day, about 90 mg/m$^2$/day, about 95 mg/m$^2$/day, about 100 mg/m$^2$/day, about 200 mg/m$^2$/day, or about 300 mg/m$^2$/day; or
   (iii) any combination thereof.

7. The method of claim 5, wherein:
(i) a dose of cyclophosphamide administered to the subject is about 400 mg/m²/day to about 600 mg/m²/day and a dose of fludarabine administered to the subject is about 20 to about 40 mg/m²/day; or
(ii) a dose of cyclophosphamide administered to the subject is about 900 mg/m²/day to about 1000 mg/m²/day and a dose of fludarabine administered to the subject is about 25 mg/m²/day.

8. The method of claim 5, wherein a dose of cyclophosphamide is administered daily for about three days.

9. The method of claim 5, wherein a dose of fludarabine is administered daily for at least two days.

10. The method of claim 1, further comprising administering one or more doses of IL-2.

11. The method of claim 1, wherein the anti-CD19 CAR T cell therapy comprises administering engineered anti-CD19 CAR T cells at a dose of about $1 \times 10^6$ to about $5 \times 10^6$ engineered CAR T cells/kg.

12. The method of claim 1, wherein the lymphoma is selected diffuse large B-cell lymphoma (DLBCL) not otherwise specified, primary mediastinal (thymic) large B cell lymphoma, DLBCL arising from follicular lymphoma, follicular lymphoma, non-Hodgkin's lymphoma (NHL), B-cell lymphoma, and mantle cell lymphoma.

13. The method of claim 5, wherein a dose of cyclophosphamide administered to the subject is about 500 mg/m²/day and a dose of fludarabine administered to the subject is about 30 mg/m²/day.

* * * * *